United States Patent
Jung et al.

(10) Patent No.: US 11,925,113 B2
(45) Date of Patent: *Mar. 5, 2024

(54) HETEROCYCLIC COMPOUND AND ORGANIC LIGHT EMITTING DEVICE COMPRISING THE SAME

(71) Applicant: LG CHEM, LTD., Seoul (KR)

(72) Inventors: Min Woo Jung, Daejeon (KR); Dong Hoon Lee, Daejeon (KR); Boonjae Jang, Daejeon (KR); Jungha Lee, Daejeon (KR); Su Jin Han, Daejeon (KR); Seulchan Park, Daejeon (KR)

(73) Assignee: LG Chem, Ltd., Seoul (KR)

( * ) Notice: Subject to any disclaimer, the term of this patent is extended or adjusted under 35 U.S.C. 154(b) by 760 days.

This patent is subject to a terminal disclaimer.

(21) Appl. No.: 16/963,189

(22) PCT Filed: Apr. 24, 2019

(86) PCT No.: PCT/KR2019/004969
§ 371 (c)(1),
(2) Date: Jul. 17, 2020

(87) PCT Pub. No.: WO2019/209031
PCT Pub. Date: Oct. 31, 2019

(65) Prior Publication Data
US 2021/0119139 A1    Apr. 22, 2021

(30) Foreign Application Priority Data

Apr. 24, 2018 (KR) .................. 10-2018-0047306
Apr. 23, 2019 (KR) .................. 10-2019-0047557

(51) Int. Cl.
*H10K 85/60* (2023.01)
*C07D 405/04* (2006.01)
(Continued)

(52) U.S. Cl.
CPC ......... *H10K 85/654* (2023.02); *C07D 405/04* (2013.01); *C07D 405/10* (2013.01);
(Continued)

(58) Field of Classification Search
CPC .................. H10K 85/6574; H10K 85/6576
See application file for complete search history.

(56) References Cited

U.S. PATENT DOCUMENTS 9,543,530 B2    1/2017   Kim et al.
9,911,925 B2    3/2018   Lee et al.
(Continued)

FOREIGN PATENT DOCUMENTS

CN    107033128 A    8/2017
CN    109071513 A    12/2018
(Continued)

*Primary Examiner* — Sean M DeGuire
(74) *Attorney, Agent, or Firm* — Bryan Cave Leighton Paisner LLP

(57) ABSTRACT

Provided is a heterocyclic compound of Chemical Formula 1:

(Continued)

wherein:

$Y_1$ is O or S;

$Ar_1$ is a substituted $C_{6-60}$ aryl; or a substituted or unsubstituted $C_{1-60}$ heteroaryl containing one or more heteroatoms selected from among O, N, Si, and S;

L is a single bond; a substituted or unsubstituted $C_{6-60}$ arylene; or a substituted or unsubstituted $C_{1-60}$ heteroarylene containing one or more heteroatoms selected from among O, N, Si, and S;

$R_1$ to $R_3$ are each independently hydrogen; deuterium; a halogen; cyano; nitro; amino; a substituted or unsubstituted $C_{1-60}$ alkyl; a substituted or unsubstituted $C_{1-60}$ haloalkyl; or a substituted or unsubstituted: $C_{1-60}$ alkoxy, $C_{1-60}$ haloalkoxy, $C_{3-60}$ cycloalkyl, $C_{2-60}$ alkenyl, $C_{6-60}$ aryl, $C_{6-60}$ aryloxy, or $C_{1-60}$ heteroaryl containing one or more heteroatoms selected from among N, O, and S, and n1 to n3 are each independently 1 to 5, and an organic light emitting device including the same.

11 Claims, 1 Drawing Sheet

(51) Int. Cl.
| | | |
|---|---|---|
| *C07D 405/10* | (2006.01) | |
| *C07D 405/14* | (2006.01) | |
| *C07D 409/14* | (2006.01) | |
| *H10K 50/11* | (2023.01) | |
| *H10K 101/00* | (2023.01) | |

(52) U.S. Cl.
CPC .......... *C07D 405/14* (2013.01); *C07D 409/14* (2013.01); *H10K 85/6572* (2023.02); *H10K 85/6574* (2023.02); *H10K 85/6576* (2023.02); *H10K 50/11* (2023.02); *H10K 2101/90* (2023.02)

(56) References Cited

U.S. PATENT DOCUMENTS

| | | |
|---|---|---|
| 10,622,565 B2 | 4/2020 | Parham et al. |
| 2004/0251816 A1 | 12/2004 | Leo et al. |
| 2016/0072078 A1 | 3/2016 | Lee et al. |
| 2016/0087224 A1 | 3/2016 | Kim et al. |
| 2016/0087227 A1 | 3/2016 | Kim et al. |
| 2016/0197285 A1 | 7/2016 | Zeng et al. |
| 2016/0226001 A1 | 8/2016 | Parham et al. |
| 2017/0186965 A1 | 6/2017 | Parham et al. |
| 2017/0222160 A1 | 8/2017 | Lee et al. |
| 2018/0141957 A1 | 5/2018 | Park et al. |
| 2018/0269407 A1 | 9/2018 | Schaefer et al. |
| 2018/0337348 A1 | 11/2018 | Jung et al. |
| 2019/0372012 A1 | 12/2019 | Cho et al. |
| 2020/0058877 A1 | 2/2020 | Cha et al. |
| 2020/0231581 A1* | 7/2020 | Chae ................. H10K 85/6576 |
| 2022/0064153 A1 | 3/2022 | Jung et al. |
| 2022/0336757 A1 | 10/2022 | Jung et al. |

FOREIGN PATENT DOCUMENTS

| | | |
|---|---|---|
| CN | 109661450 A | 4/2019 |
| EP | 2991128 A1 | 3/2016 |
| EP | 3415512 A2 | 12/2018 |
| KR | 10-2000-0051826 | 8/2000 |
| KR | 10-2012-0116272 | 10/2012 |
| KR | 10-2014-0020208 | 2/2014 |
| KR | 10-2014-0049227 | 4/2014 |
| KR | 10-2015-0094398 | 8/2015 |
| KR | 10-2016-0026744 | 3/2016 |
| KR | 10-2016-0028524 | 3/2016 |
| KR | 10-2016-0085206 | 7/2016 |
| KR | 10-2016-0107083 | 9/2016 |
| KR | 10-2016-0112111 | 9/2016 |
| KR | 10-2017-0089599 | 8/2017 |
| KR | 10-2017-0093061 | 8/2017 |
| KR | 10-2018-0010130 | 1/2018 |
| KR | 10-2018-0010167 | 1/2018 |
| KR | 10-2018-0029429 | 3/2018 |
| KR | 10-2019-0008035 | 1/2019 |
| KR | 10-2019-0038246 | 4/2019 |
| TW | 201811773 A | 4/2018 |
| WO | 2003-012890 | 2/2003 |
| WO | 2011-139055 | 11/2011 |
| WO | 2012-141499 | 10/2012 |
| WO | 2012-169821 | 12/2012 |
| WO | 2013-032278 | 3/2013 |
| WO | 2014-017844 | 1/2014 |
| WO | 2014-042420 | 3/2014 |
| WO | 2014-061991 | 4/2014 |
| WO | 2014-088347 | 6/2014 |
| WO | 2015-036080 | 3/2015 |
| WO | 2015-093878 | 6/2015 |
| WO | 2015-169412 | 11/2015 |
| WO | 2017-056055 | 4/2017 |

* cited by examiner

【FIG. 1】
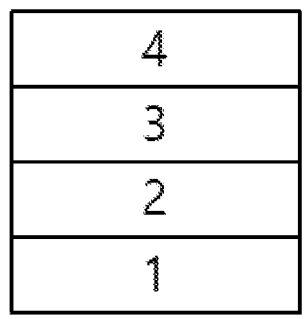
【FIG. 2】
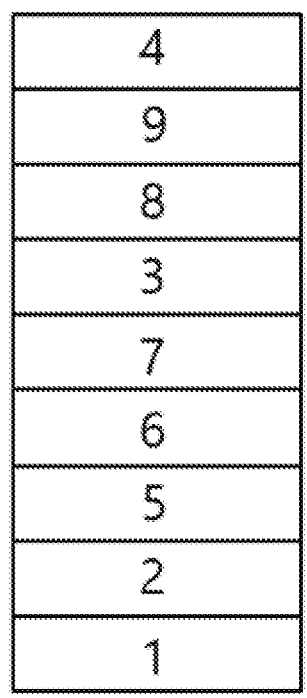

HETEROCYCLIC COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2019/004969 filed on Apr. 24, 2019, which claims the benefits of the filing dates of Korean Patent Application No. 10-2018-0047306 filed with Korean Intellectual Property Office on Apr. 24, 2018, and Korean Patent Application No. 10-2019-0047557 filed with Korean Intellectual Property Office on Apr. 23, 2019, the entire contents of which are incorporated herein by reference.

FIELD OF THE INVENTION

The present invention relates to a novel heterocyclic compound and to an organic light emitting device including the same.

BACKGROUND OF THE INVENTION

In general, an organic light emitting phenomenon refers to one where electrical energy is converted into light energy by using an organic material. The organic light emitting device using the organic light emitting phenomenon has characteristics such as a wide viewing angle, excellent contrast, a fast response time, and excellent luminance, driving voltage, and response speed, and thus many studies have proceeded thereon.

The organic light emitting device generally has a structure which includes an anode, a cathode, and an organic material layer interposed between the anode and the cathode. The organic material layer frequently has a multilayered structure that includes different materials in order to enhance efficiency and stability of the organic light emitting device, and for example, the organic material layer can be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state.

There is a continuing need for the development of new materials for the organic materials used in these organic light emitting devices.

PRIOR ART LITERATURE

Patent Document

Korean Patent Laid-open Publication No. 10-2000-0051826

BRIEF DESCRIPTION

Technical Problem

It is an object of the present invention to provide a novel heterocyclic compound and an organic light emitting device including the same.

Technical Solution

In one aspect of the invention, a compound of the following Chemical Formula 1 is provided:

Chemical Formula 1

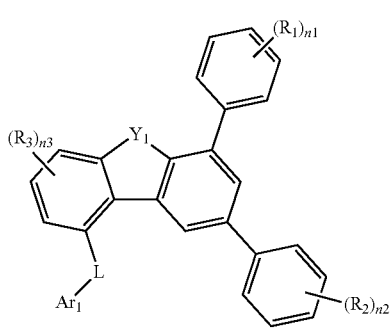

wherein, in Chemical Formula 1:
$Y_1$ is O or S,
$Ar_1$ is a substituted $C_{6-60}$ aryl or a substituted or unsubstituted $C_{1-60}$ heteroaryl containing one or more heteroatoms selected from the group consisting of O, N, Si, and S,
L is a single bond, a substituted or unsubstituted $C_{6-60}$ arylene, or a substituted or unsubstituted $C_{1-60}$ heteroarylene containing one or more heteroatoms selected from the group consisting of O, N, Si, and S,
$R_1$ to $R_3$ are each independently hydrogen, deuterium, a halogen, cyano, nitro, amino, a substituted or unsubstituted $C_{1-60}$ alkyl, a substituted or unsubstituted $C_{1-60}$ haloalkyl, a substituted or unsubstituted $C_{1-60}$ alkoxy, a substituted or unsubstituted $C_{1-60}$ haloalkoxy, a substituted or unsubstituted $C_{3-60}$ cycloalkyl, a substituted or unsubstituted $C_{2-60}$ alkenyl, a substituted or unsubstituted $C_{6-60}$ aryl, a substituted or unsubstituted $C_{6-60}$ aryloxy, or a substituted or unsubstituted $C_{1-60}$ heteroaryl containing one or more heteroatoms selected from the group consisting of N, O, and S, and
n1 to n3 are each independently an integer of 1 to 5.

In another aspect of the invention, an organic light emitting device including a first electrode; a second electrode provided opposite to the first electrode; and one or more organic material layers provided between the first electrode and the second electrode, wherein one or more layers of the organic material layers includes the compound of Chemical Formula 1, is provided.

Advantageous Effects

The compound of Chemical Formula 1 described above can be used as a material of an organic material layer of an organic light emitting device, and can improve efficiency, achieve a low driving voltage, and/or improve lifetime characteristics in the organic light emitting device.

BRIEF DESCRIPTION OF THE DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, an electron blocking layer 7, a light emitting layer 3, an electron transport layer 8, an electron injection layer 9, and a cathode 4.

DETAILED DESCRIPTION OF THE EMBODIMENTS

Hereinafter, the present invention will be described in more detail to help understanding of the present invention.

In one embodiment of the invention, a compound of Chemical Formula 1 is provided.

As used herein, the notation

means a bond linked to another substituent group.

As used herein, the term "substituted or unsubstituted" means being unsubstituted or substituted with one or more substituents selected from the group consisting of deuterium, a halogen group, a cyano group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heteroaryl containing at least one of N, O, and S atoms, or being unsubstituted or substituted with a substituent to which two or more substituents are linked among the substituents exemplified above. For example, when "the substituent to which two or more substituents are linked" is a biphenyl group, the biphenyl group can be interpreted as an aryl group substituted with one phenyl group, or a substituent to which two phenyl groups are linked.

In the present specification, the number of carbon atoms of a carbonyl group is not particularly limited, but is preferably 1 to 40. Specifically, the carbonyl group can be a compound having the following structural formulae, but is not limited thereto:

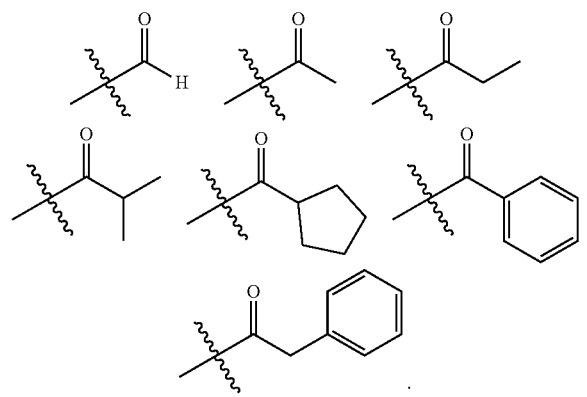

In the present specification, an ester group can have a structure in which oxygen of the ester group can be substituted by a straight-chain, branched-chain, or cyclic alkyl group having 1 to 25 carbon atoms, or an aryl group having 6 to 25 carbon atoms. Specifically, the ester group can be a compound having the following structural formulae, but is not limited thereto:

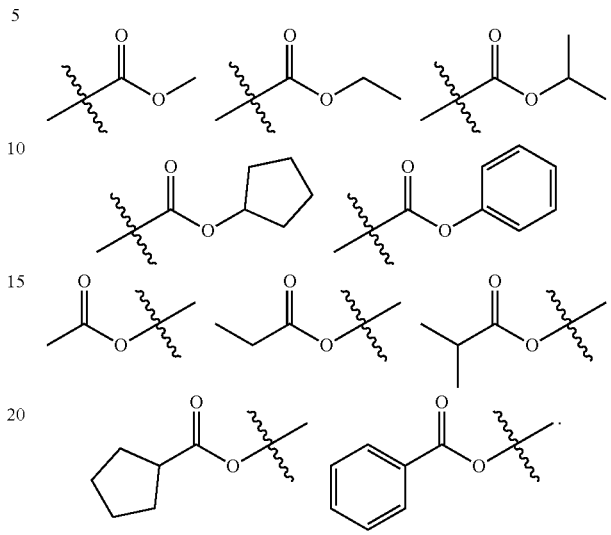

In the present specification, the number of carbon atoms of an imide group is not particularly limited, but is preferably 1 to 25. Specifically, the imide group can be a compound having the following structural formulae, but is not limited thereto:

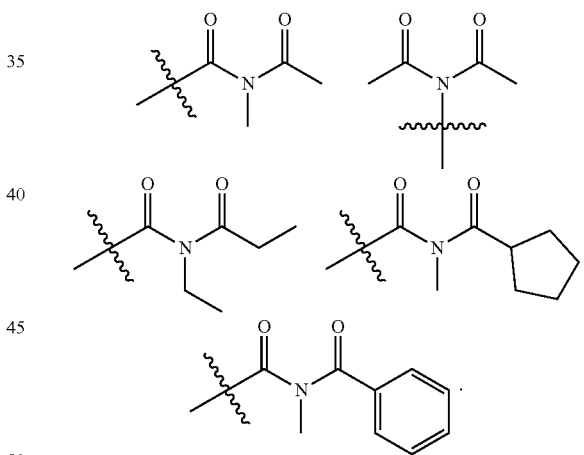

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, a boron group specifically includes a trimethylboron group, a triethylboron group, a t-butyl dimethylboron group, a triphenylboron group, and a phenylboron group, but is not limited thereto.

In the present specification, examples of a halogen group include fluorine, chlorine, bromine, and iodine.

In the present specification, the alkyl group can be a straight chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohectylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, iso-hexyl, 2-methylpentyl, 4-methylhexyl, 5-methylhexyl, and the like, but are not limited thereto.

In the present specification, the alkenyl group can be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and can be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group can be a phenyl group, a biphenyl group, a terphenyl group, or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, or the like, but are not limited thereto.

In the present specification, a heteroaryl group is a heteroaryl including one or more of O, N, Si, and S as a heteroatom, and the number of carbon atoms thereof is not particularly limited, but is preferably 2 to 60. Examples of the heteroaryl include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group, and the alkylamine group is the same as the aforementioned examples of the alkyl group. In the present specification, the heteroaryl in the heteroarylamine can be applied to the aforementioned description of the heteroaryl. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heteroaryl can be applied except that the heteroarylene is a divalent group. In the present specification, the aforementioned description of the aryl group or cycloalkyl group can be applied except that the hydrocarbon ring is not a monovalent group but is formed by combining two substituent groups. In the present specification, the aforementioned description of the heteroaryl can be applied, except that the heterocycle is not a monovalent group but is formed by combining two substituent groups.

Meanwhile, in Chemical Formula 1, $Ar_1$ can be any one selected from the group consisting of the following:

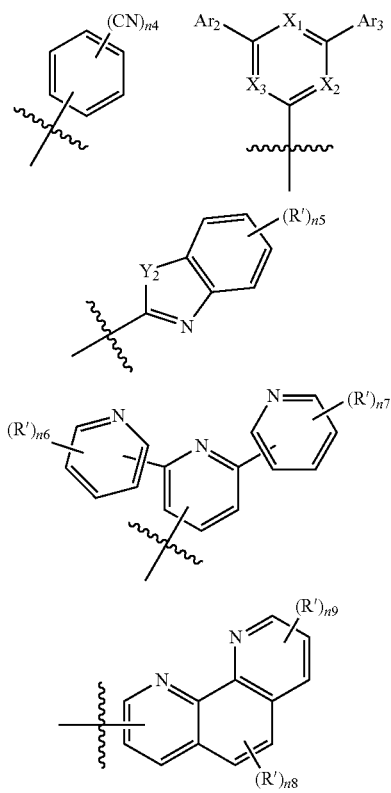

-continued

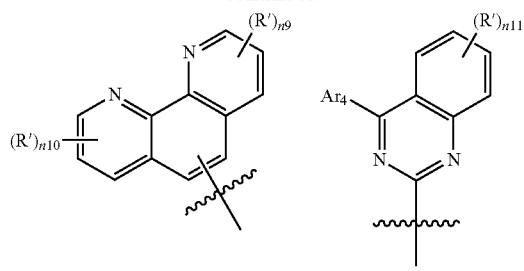

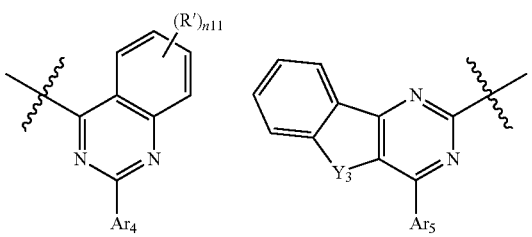

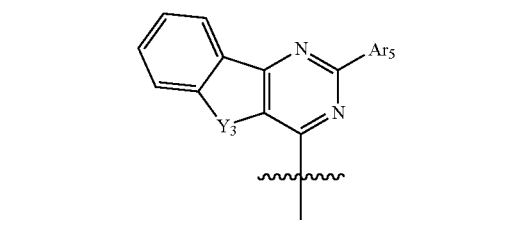

wherein:

$X_1$ to $X_3$ are each independently N or CR'3, provided that at least two of $X_1$ to $X_3$ are NI;

$Y_2$ and $Y_3$ are each independently O, S, or NR';

$Ar_2$ to $Ar_5$ are each independently a substituted or unsubstituted $C_{6-60}$ aryl or a substituted or unsubstituted $C_{1-60}$ heteroaryl containing one or more heteroatoms selected from the group consisting of O, N, Si, and S, each R' is independently hydrogen, deuterium, a halogen, cyano, nitro, amino, a substituted or unsubstituted $C_{1-60}$ alkyl, a substituted or unsubstituted $C_{1-60}$ haloalkyl, a substituted or unsubstituted $C_{1-60}$ alkoxy, a substituted or unsubstituted $C_{1-60}$ haloalkoxy, a substituted or unsubstituted $C_{3-60}$ cycloalkyl, a substituted or unsubstituted $C_{2-60}$ alkenyl, a substituted or unsubstituted $C_{6-60}$ aryl, a substituted or unsubstituted $C_{6-60}$ aryloxy, or a substituted or unsubstituted $C_{1-60}$ heteroaryl containing one or more heteroatoms selected from the group consisting of N, O, and S, and n4 to n11 can each independently be an integer of 1 to 5.

Preferably, $Ar_1$ can be any one selected from the group consisting of the following:

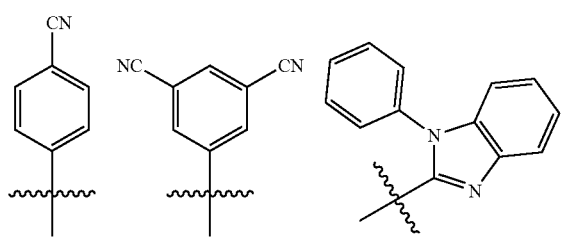

-continued

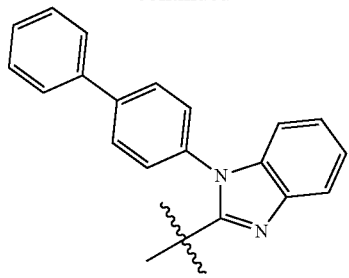

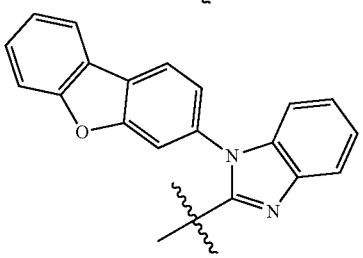

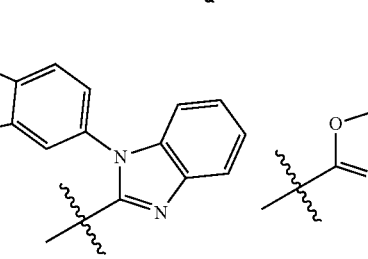

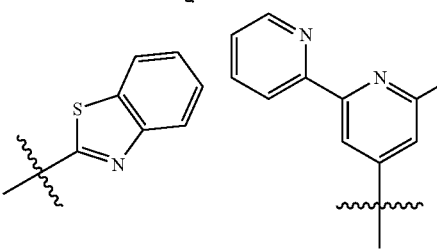

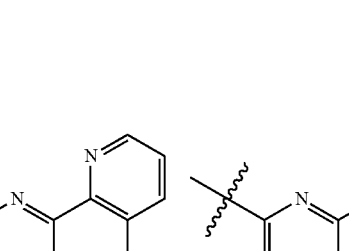

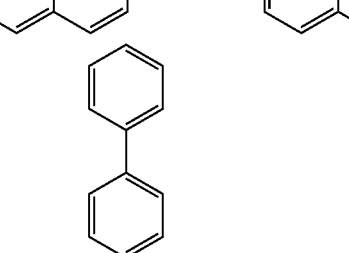

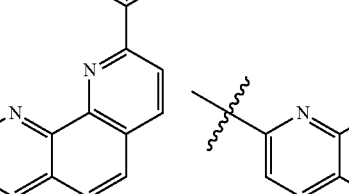

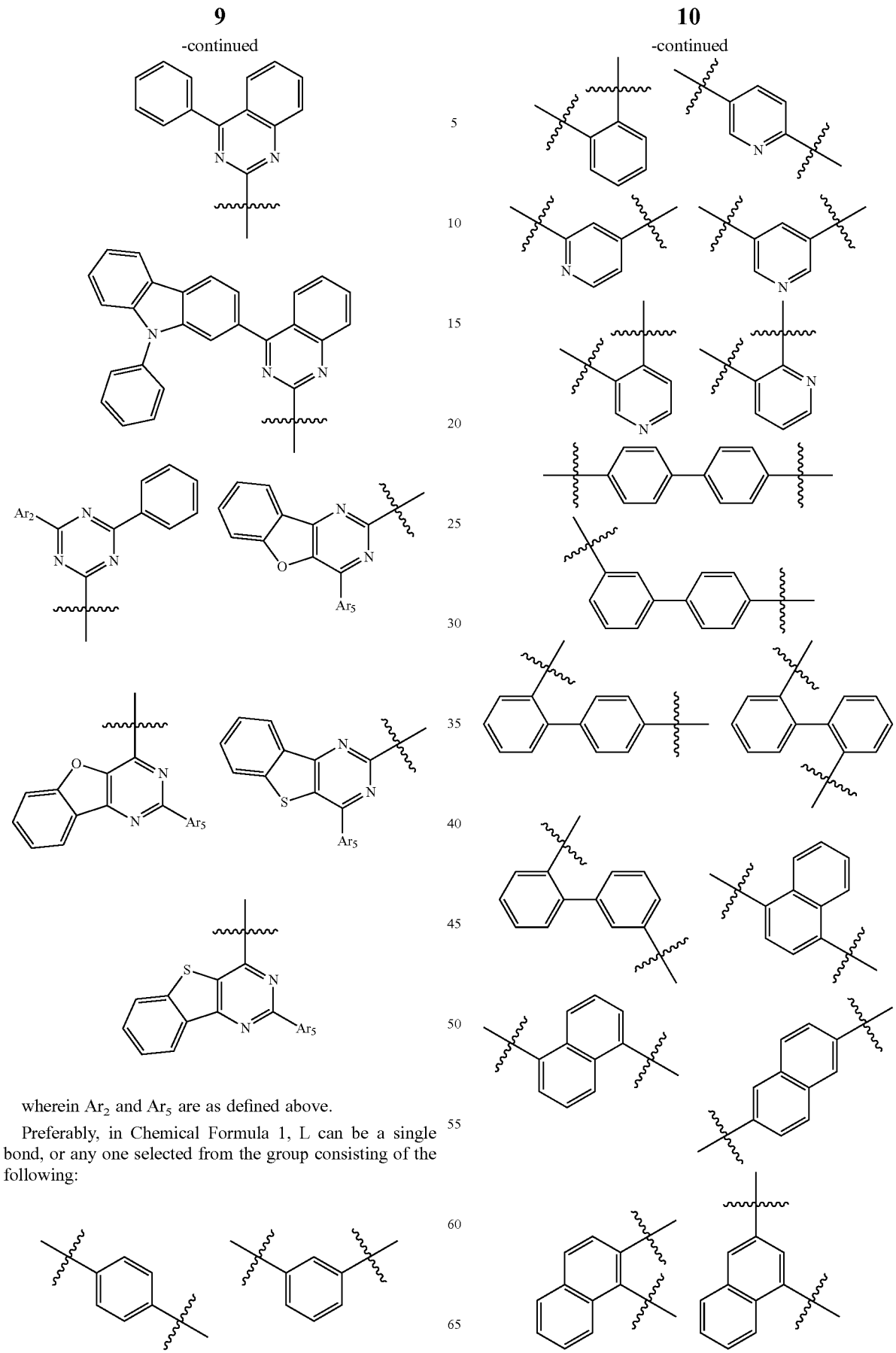
wherein Ar₂ and Ar₅ are as defined above.
Preferably, in Chemical Formula 1, L can be a single bond, or any one selected from the group consisting of the following:

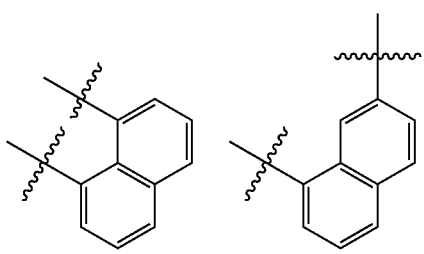
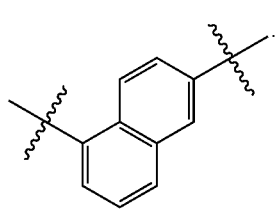
Preferably, in Chemical Formula 1, $R_1$ to $R_3$ can each independently be hydrogen; deuterium; cyano; or a substituted or unsubstituted $C_{1-10}$ alkyl.
For example, $R_1$ to $R_3$ can be hydrogen.
For example, the above-mentioned compound can be selected from the group consisting of the following compounds:
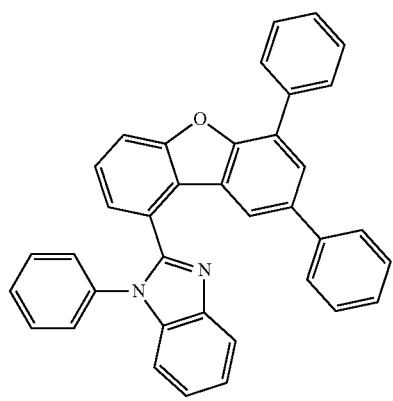
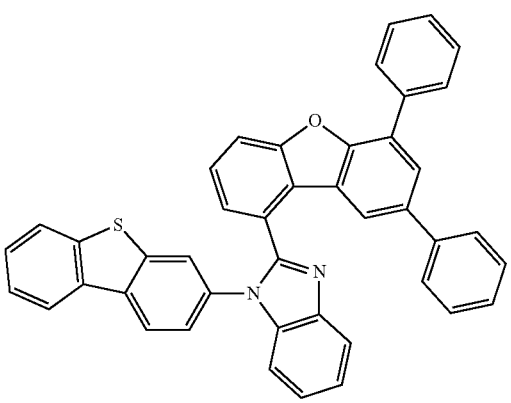
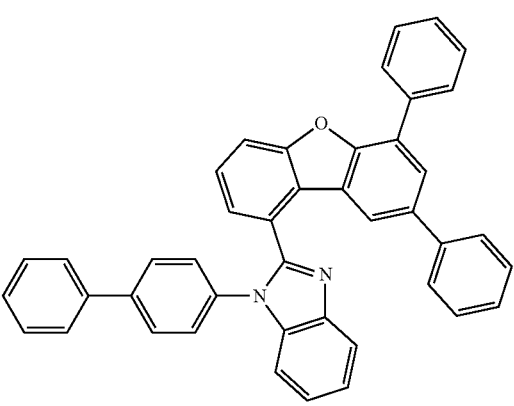
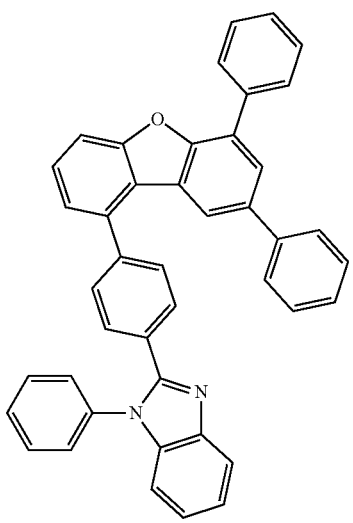

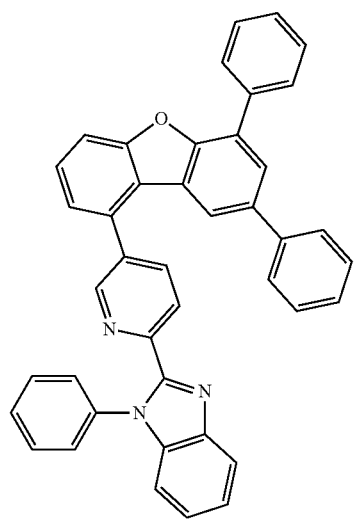
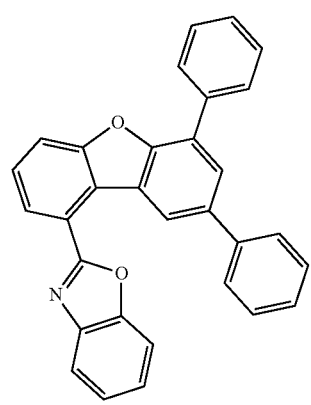
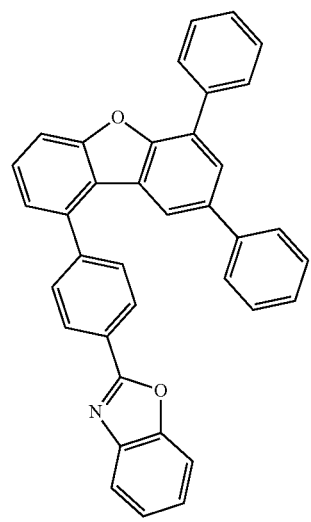
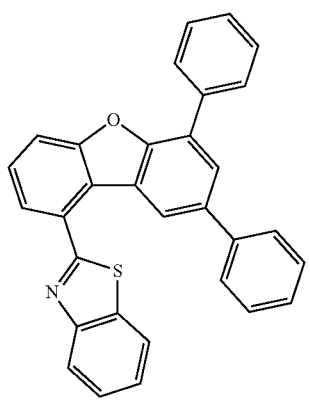
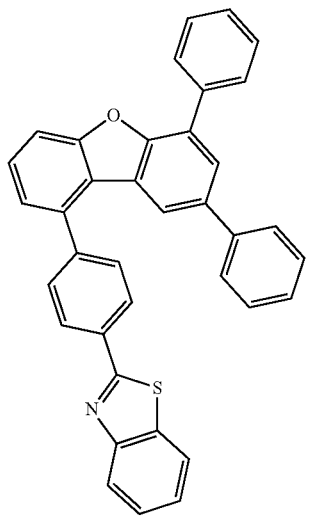
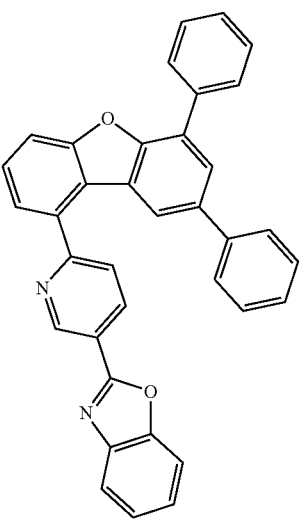

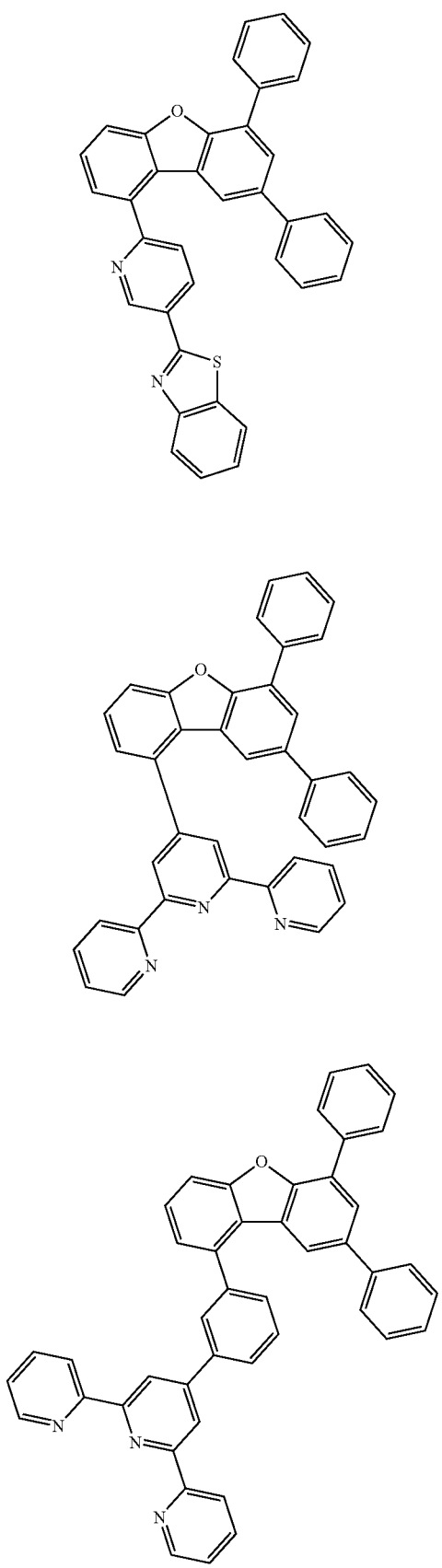
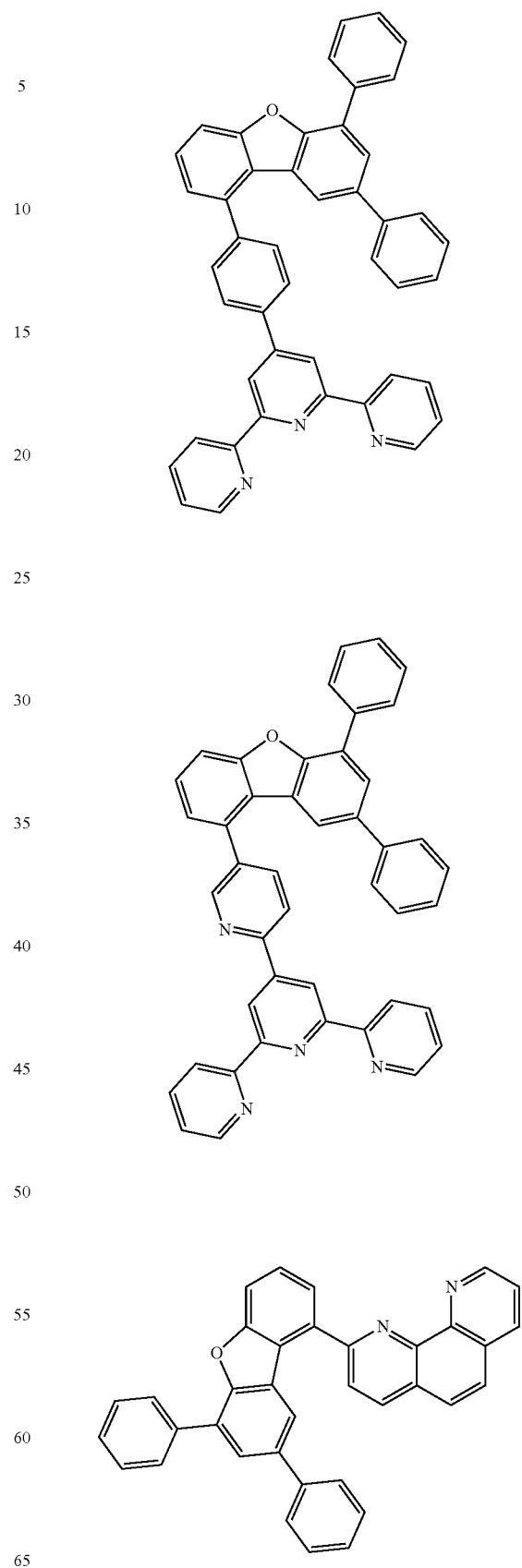

17
-continued
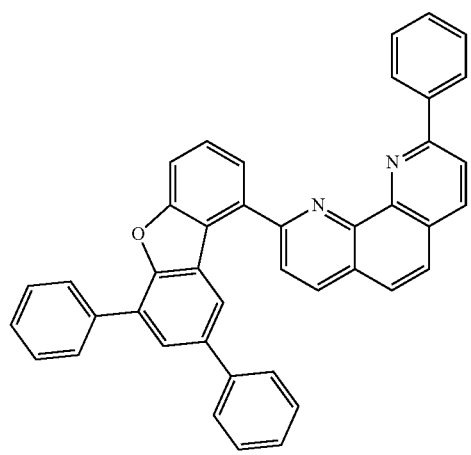
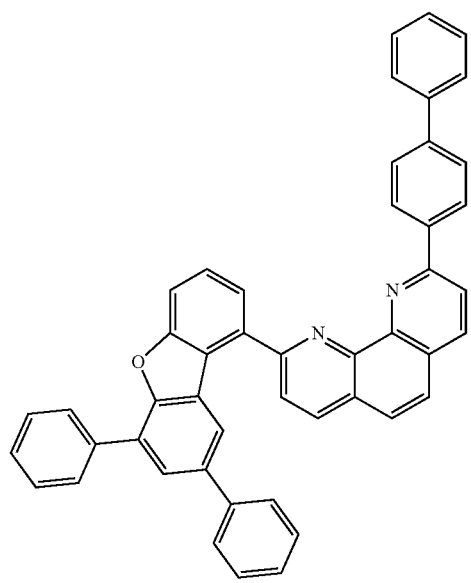
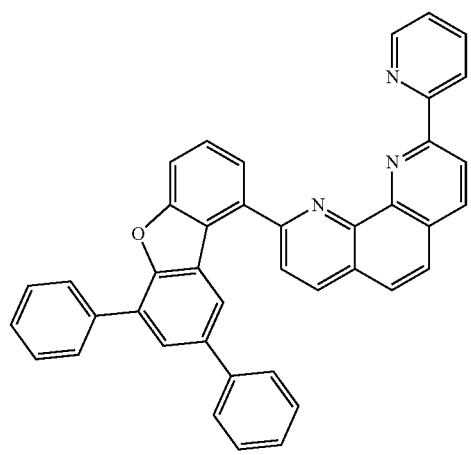
18
-continued
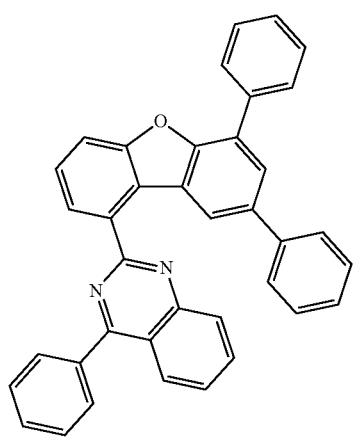
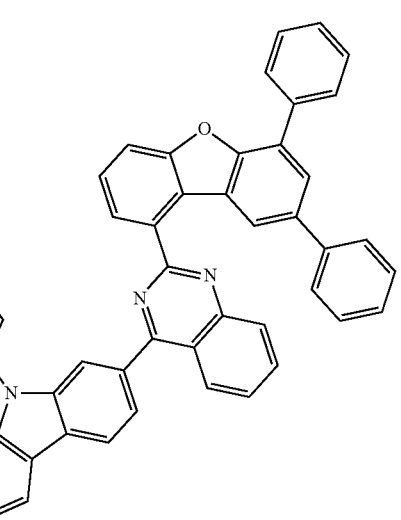
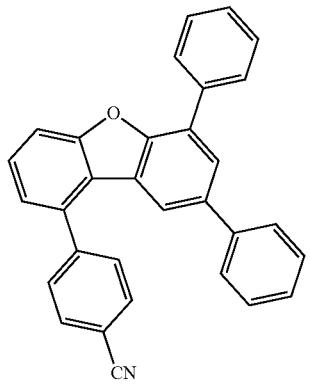

-continued
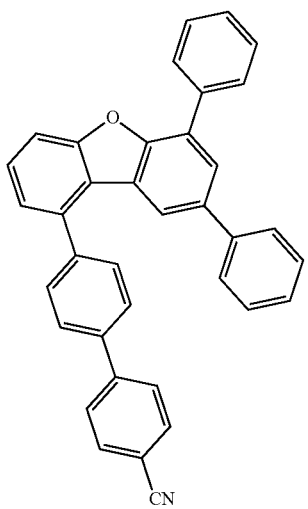
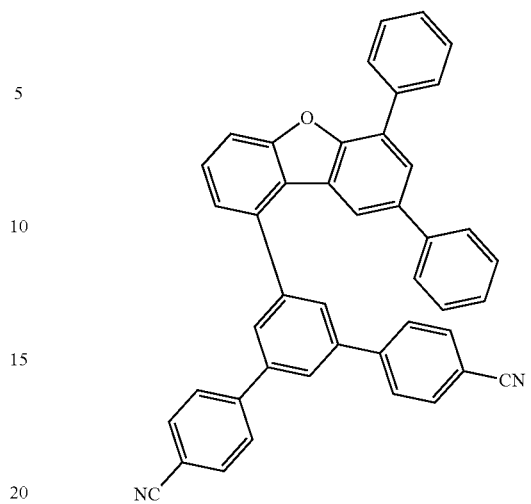
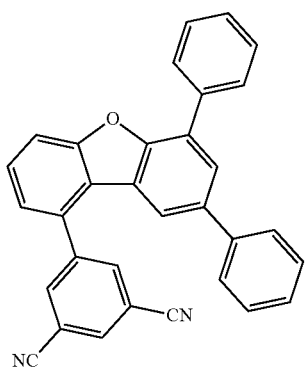
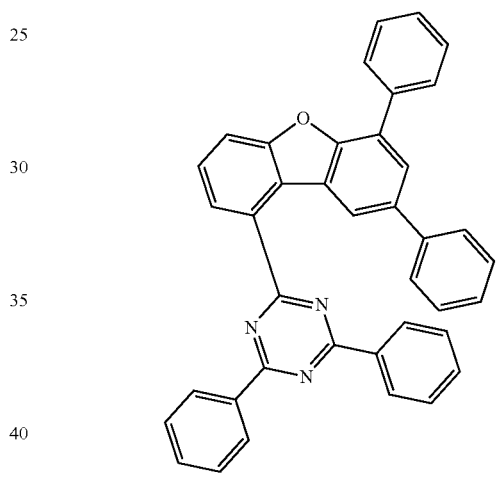
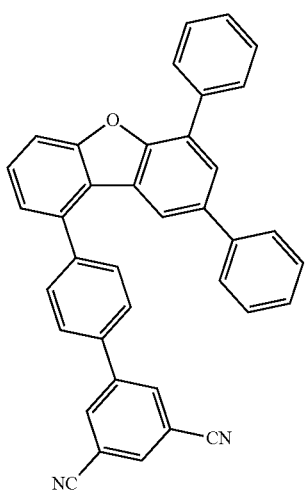
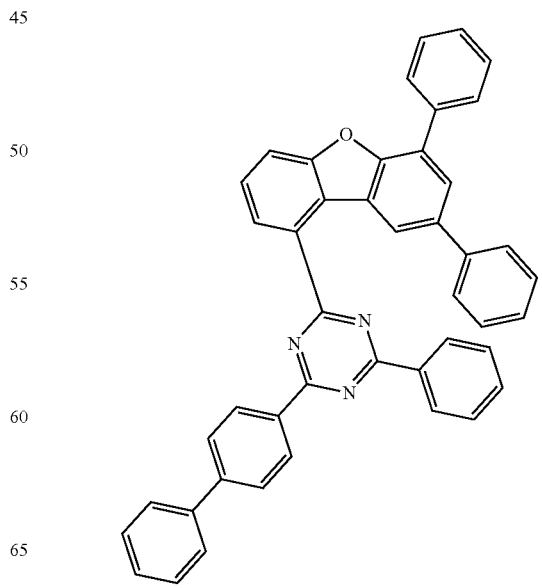

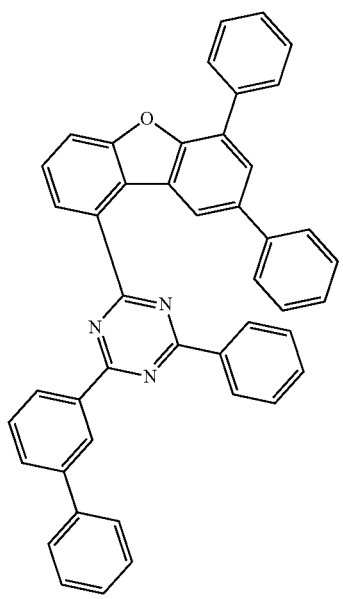
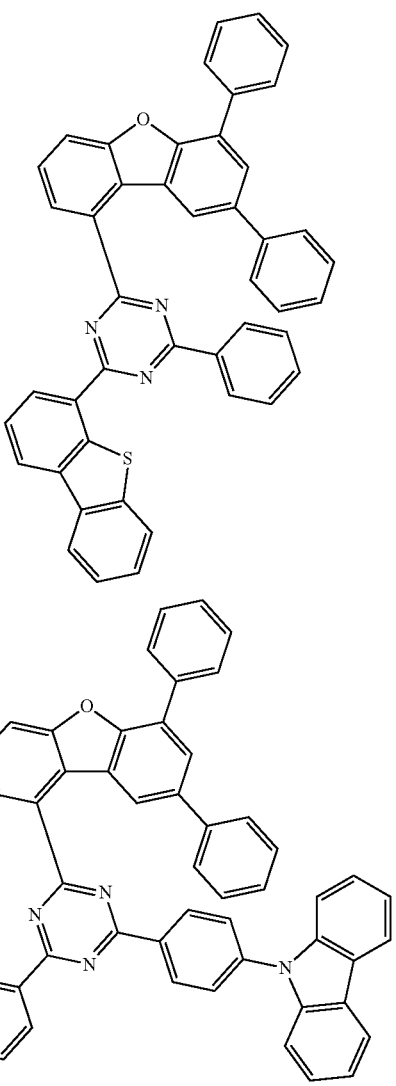
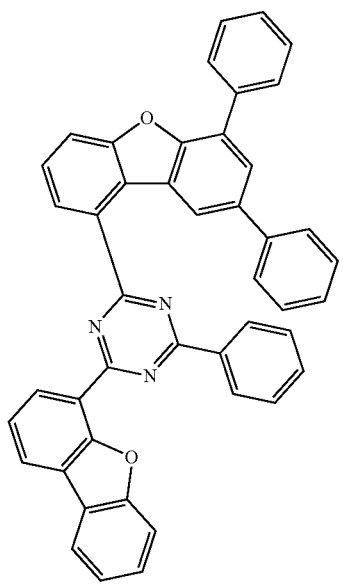
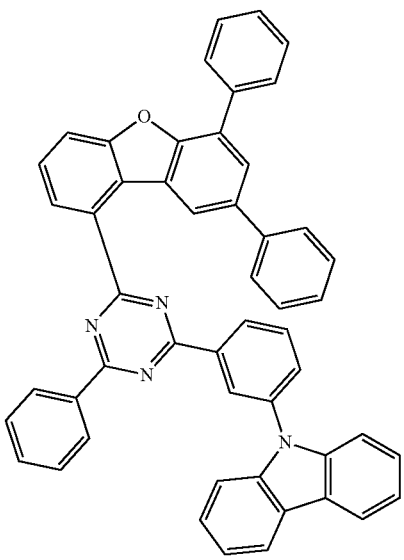

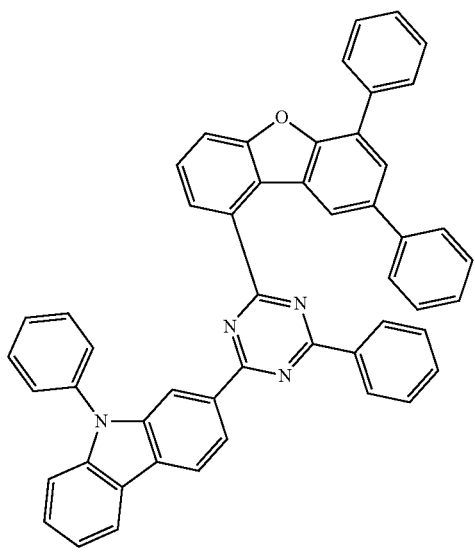
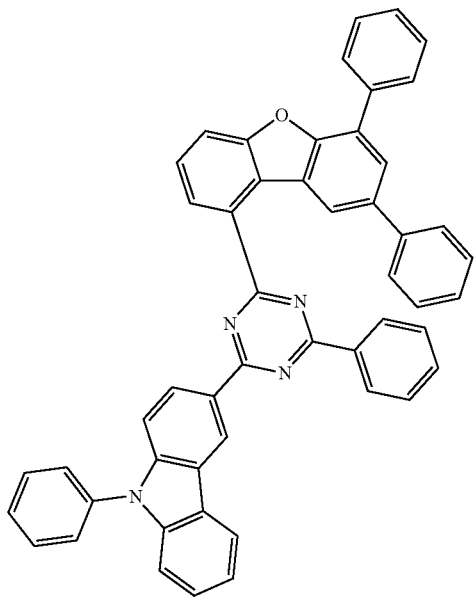
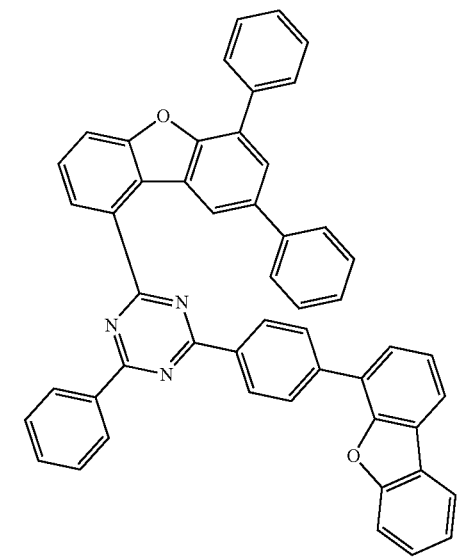
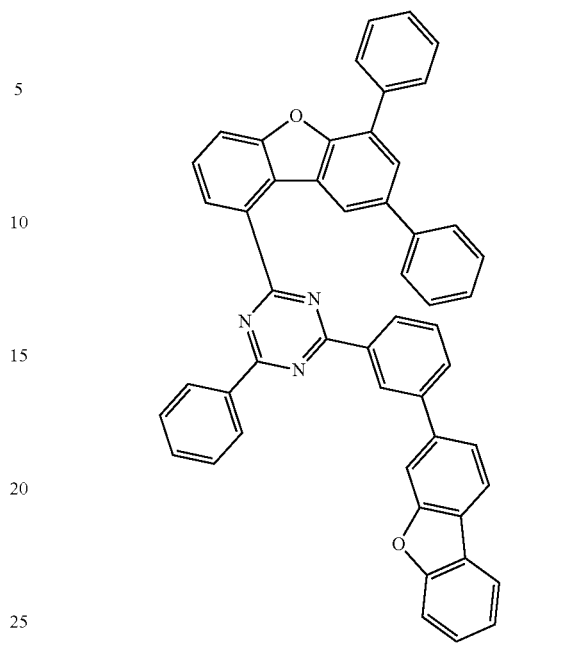
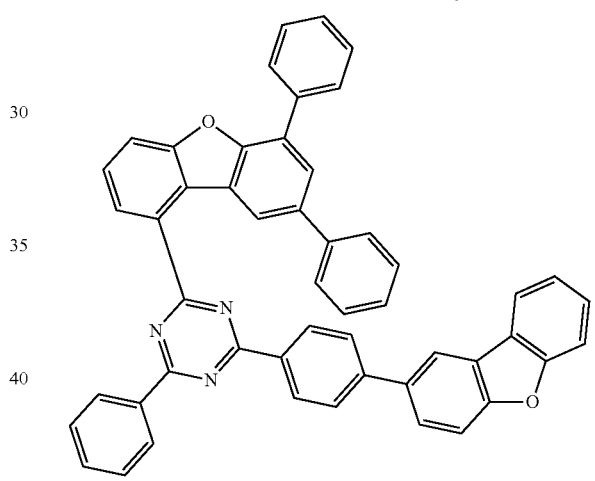
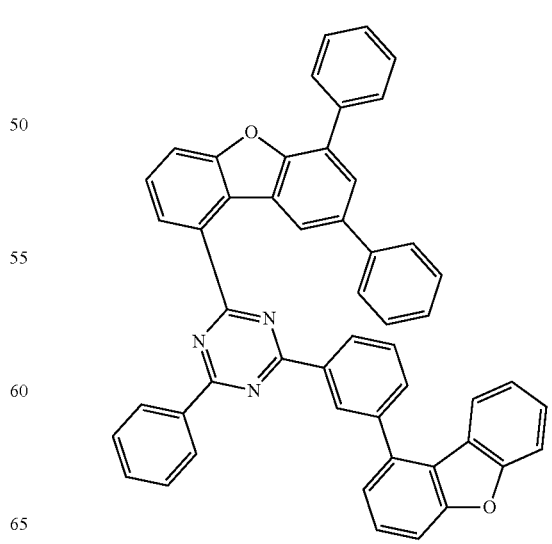

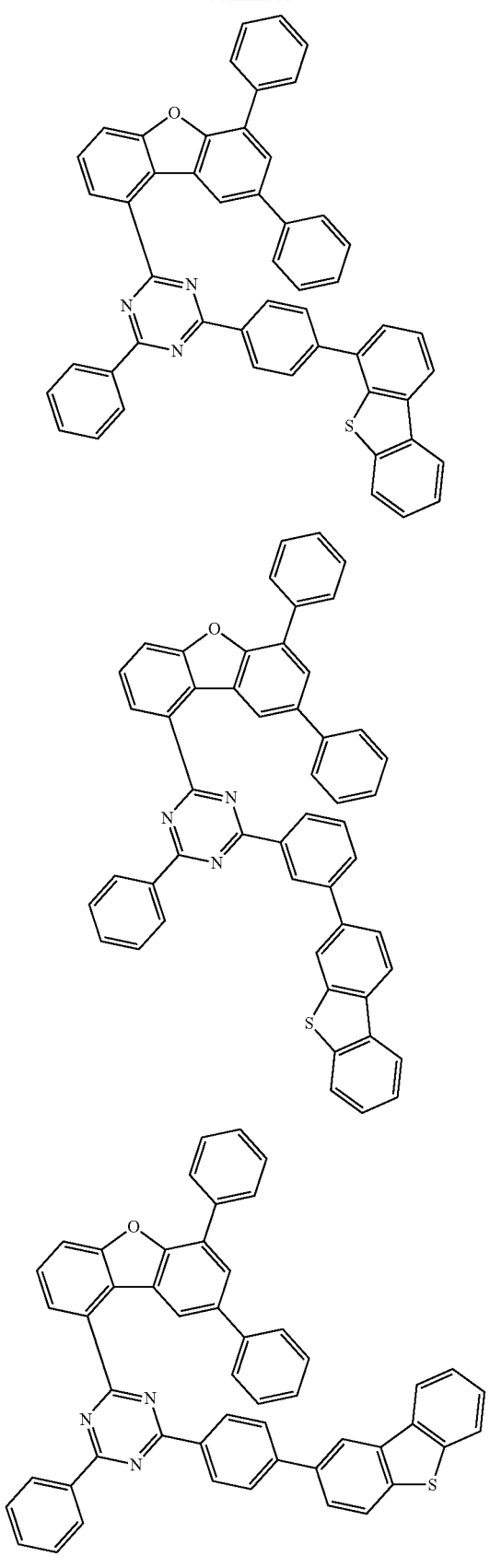
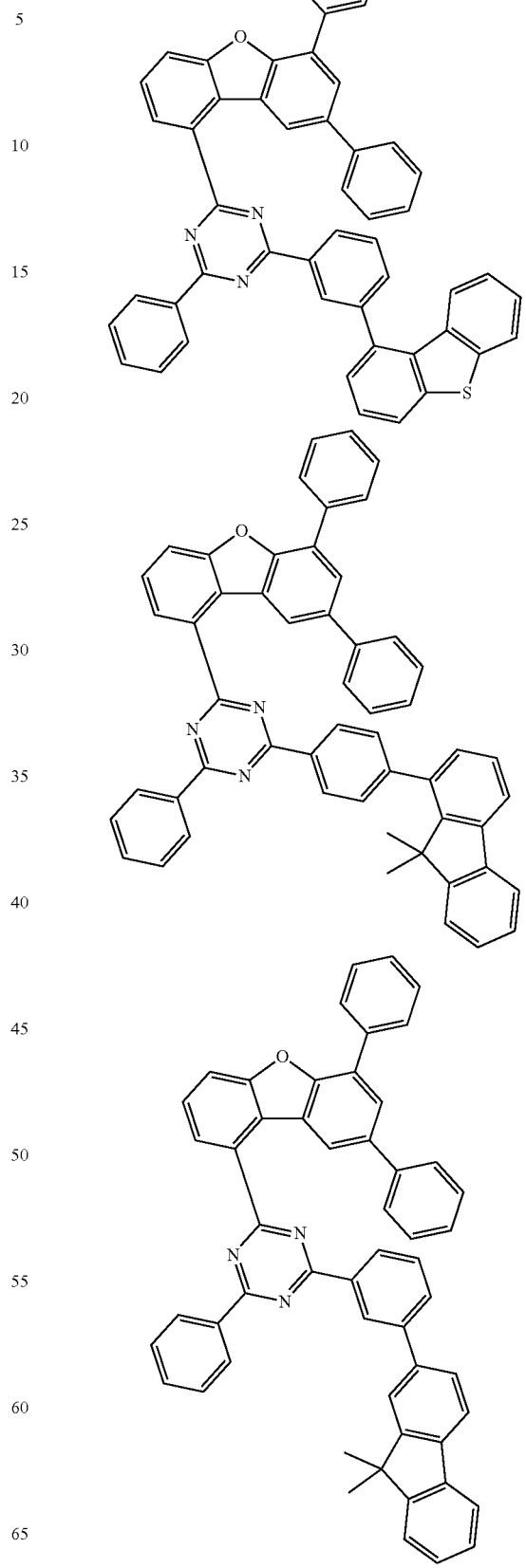

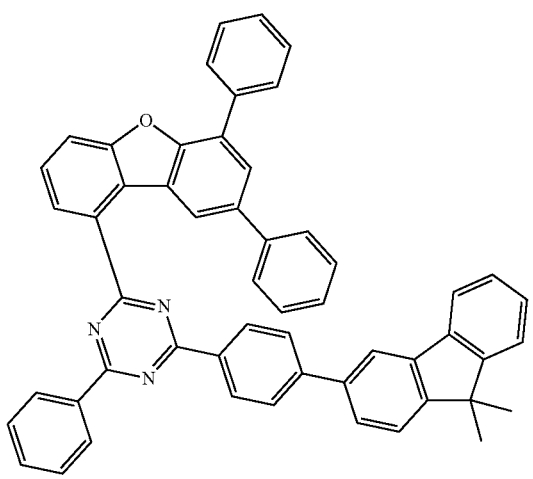
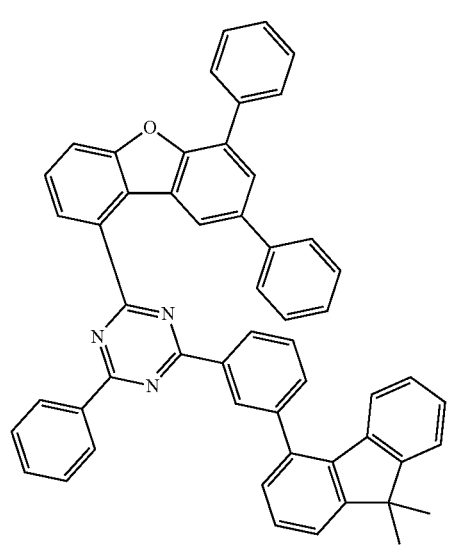
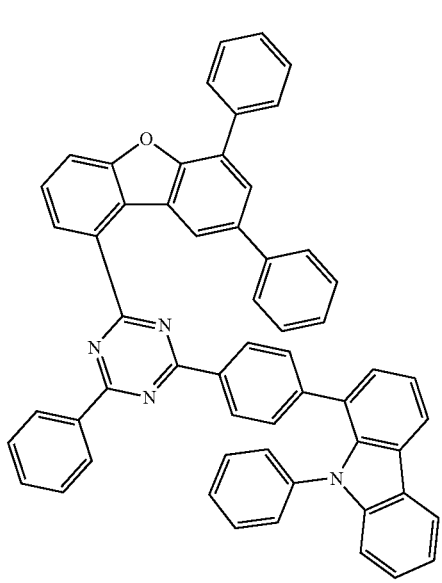
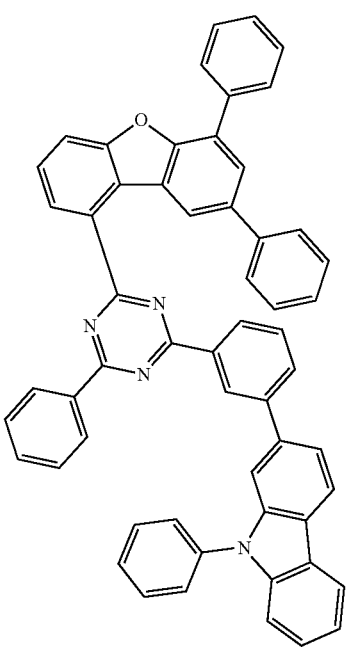
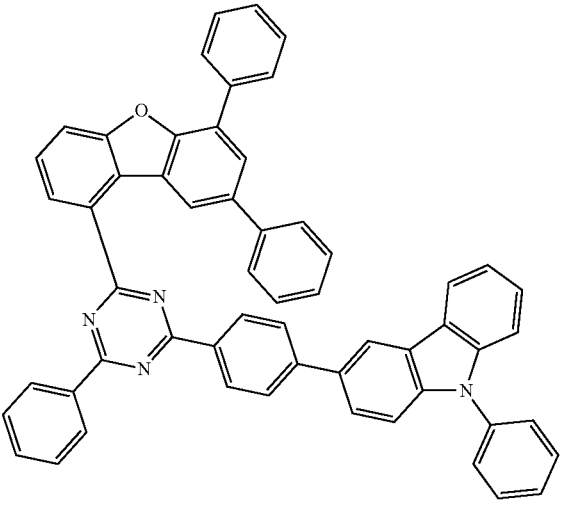

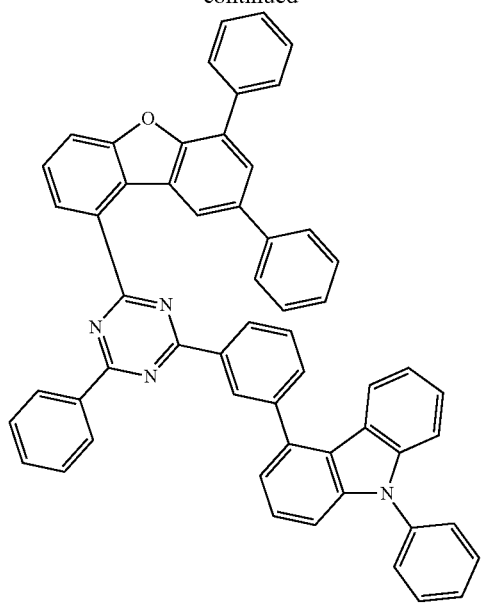
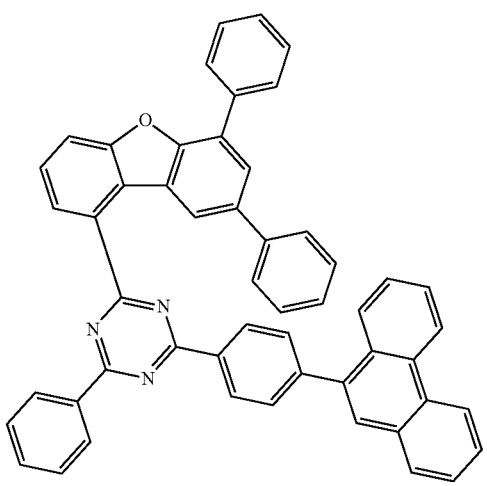
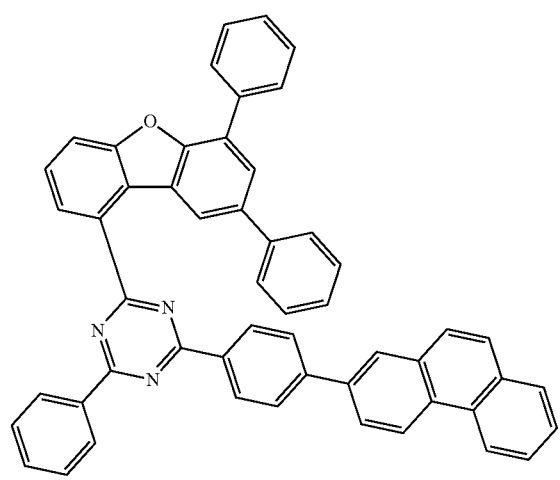
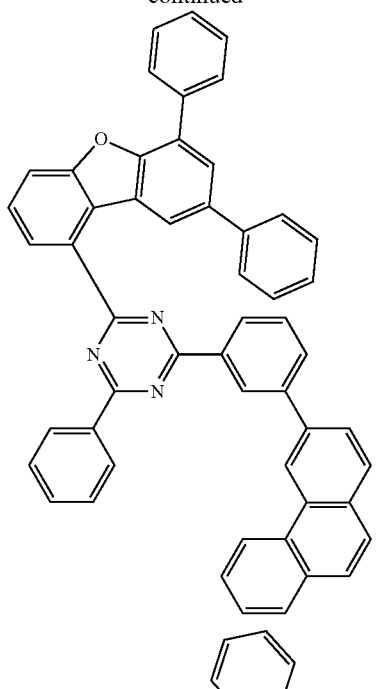
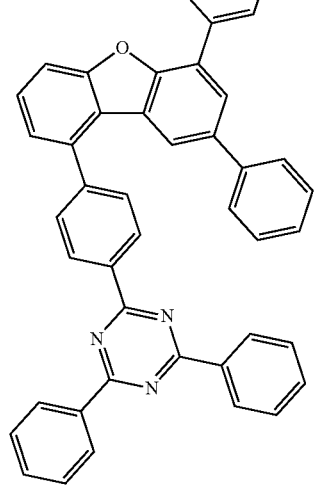
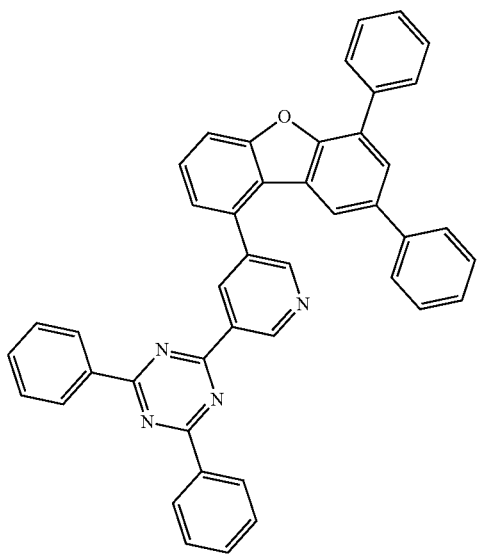

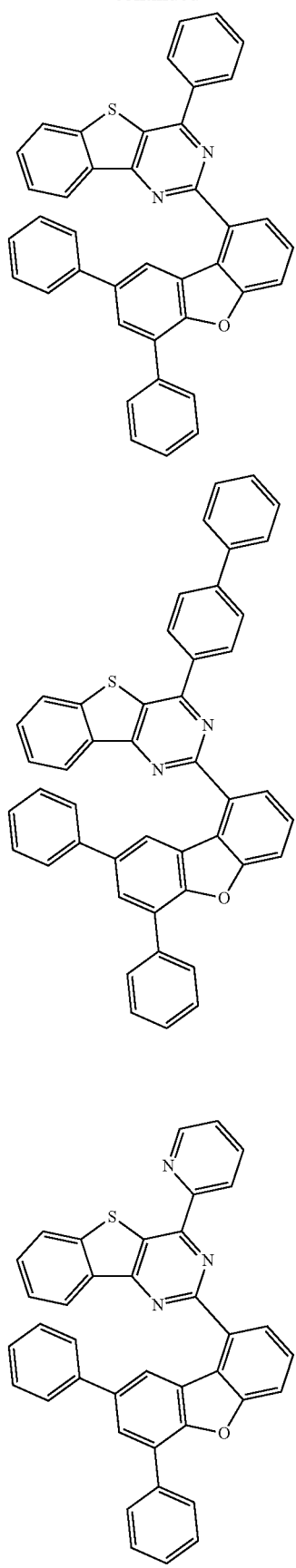

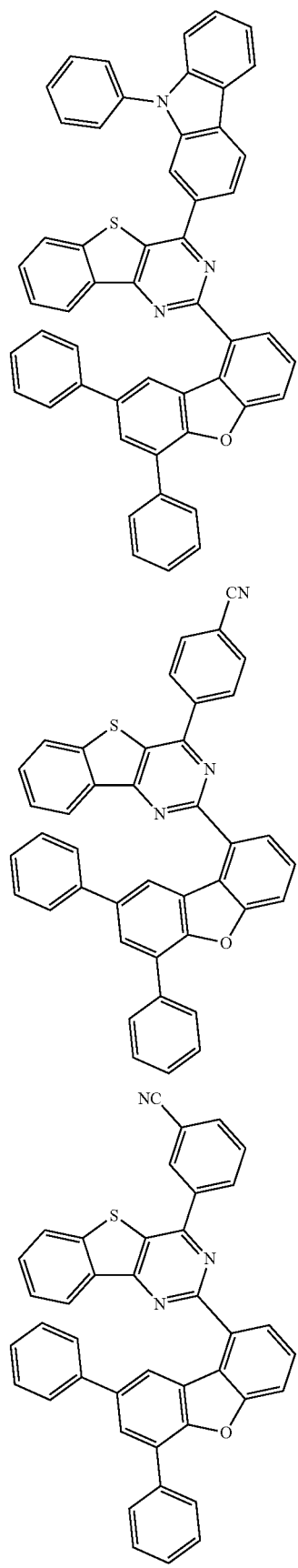
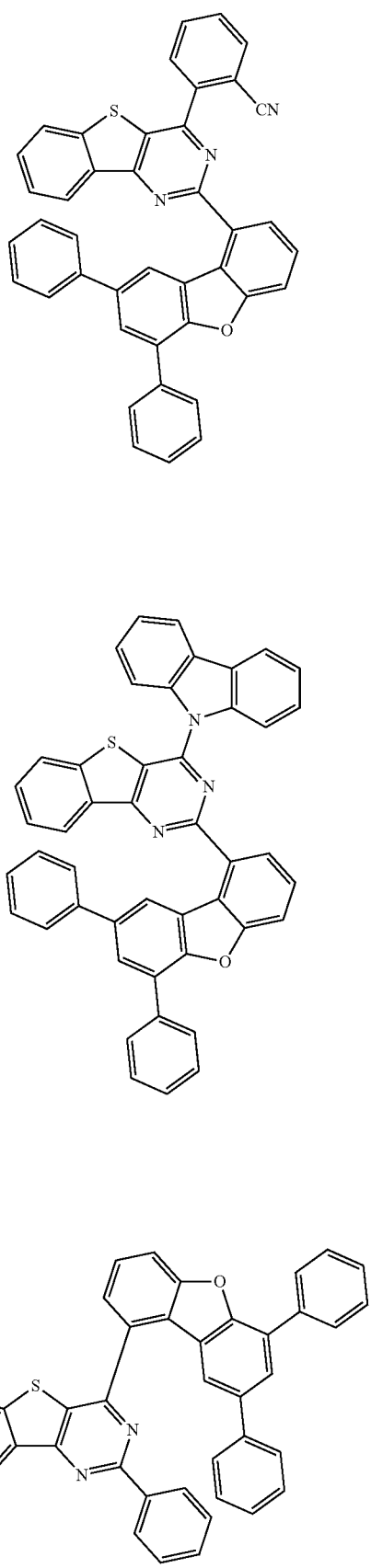

-continued
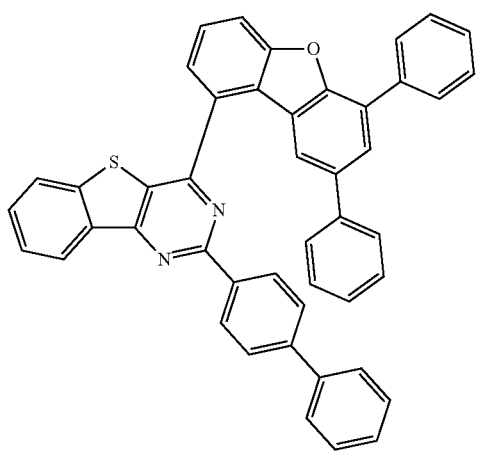
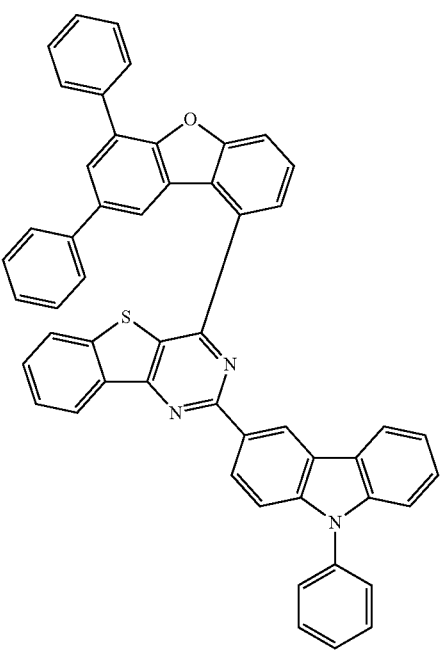
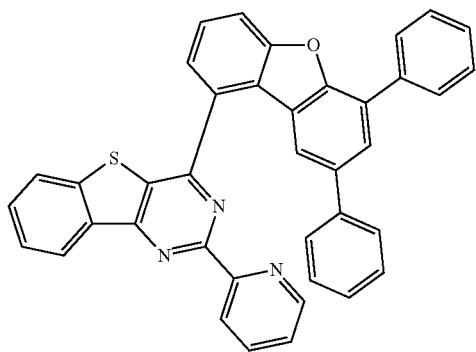
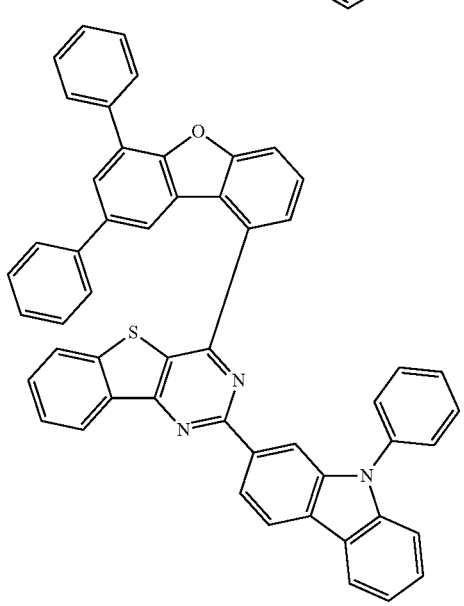
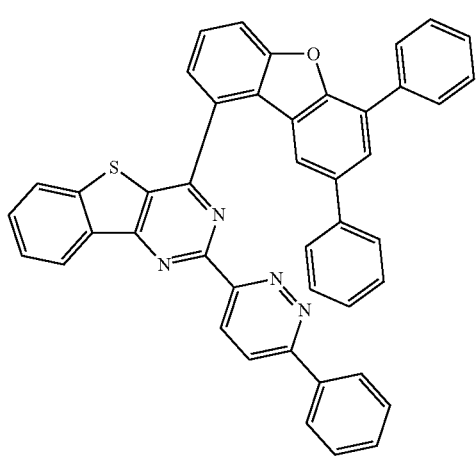
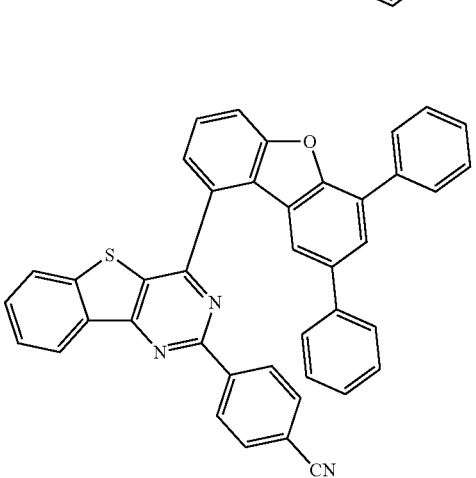

-continued
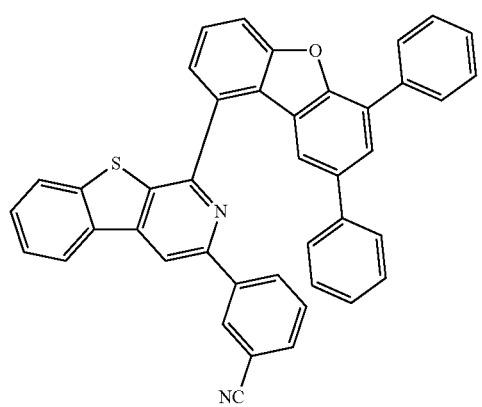
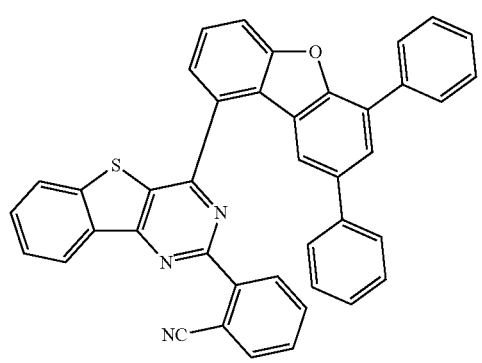
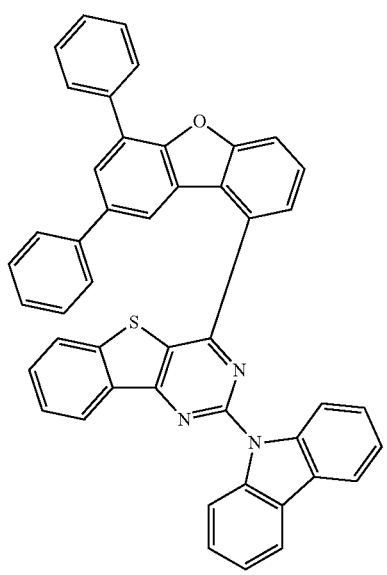
-continued
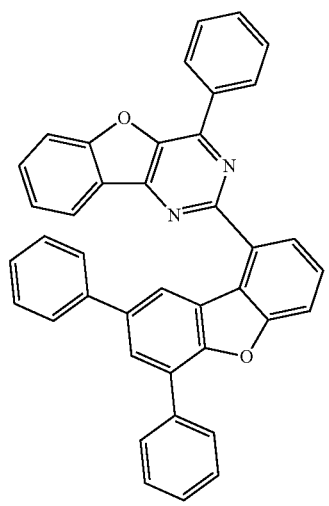
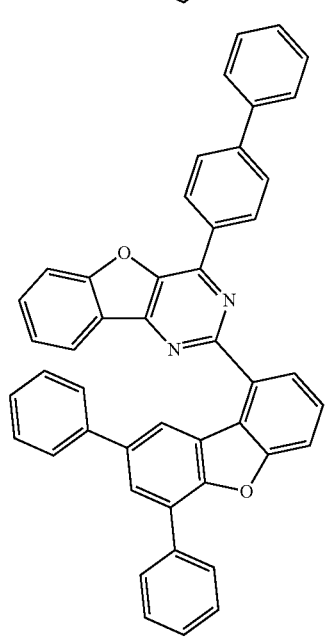
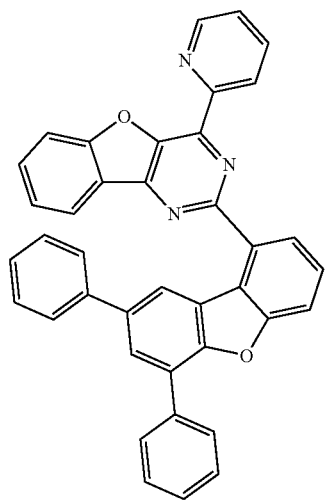

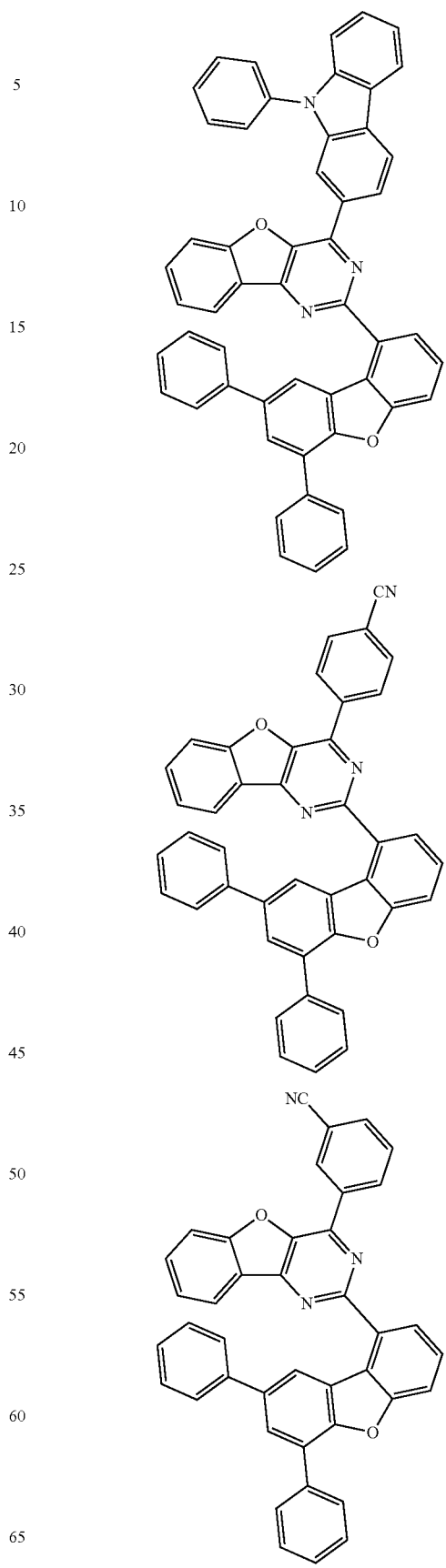

41
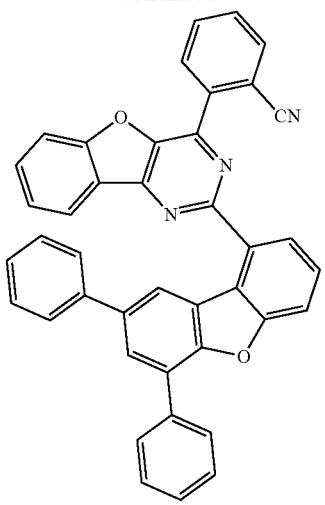
42
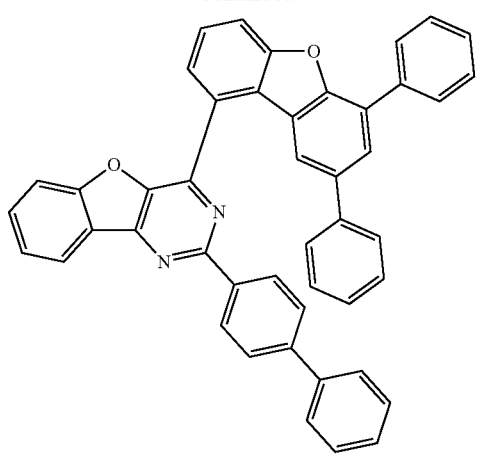
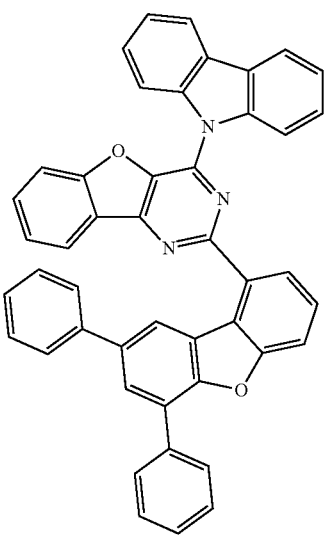
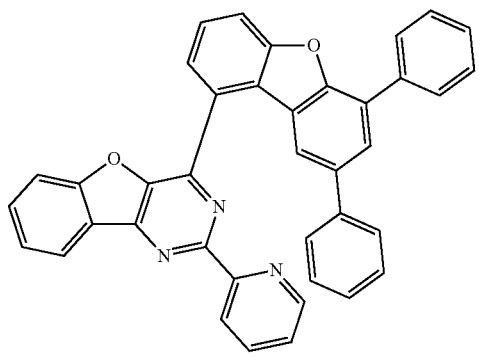
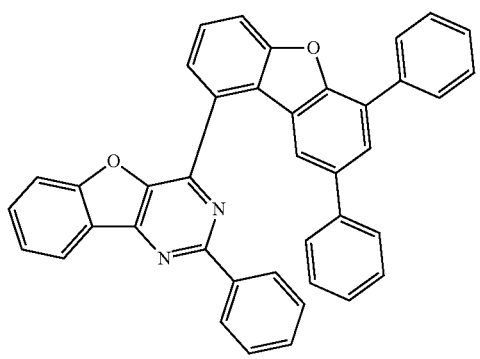
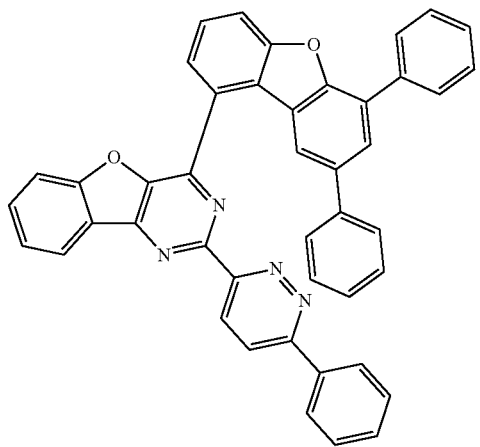

43
-continued
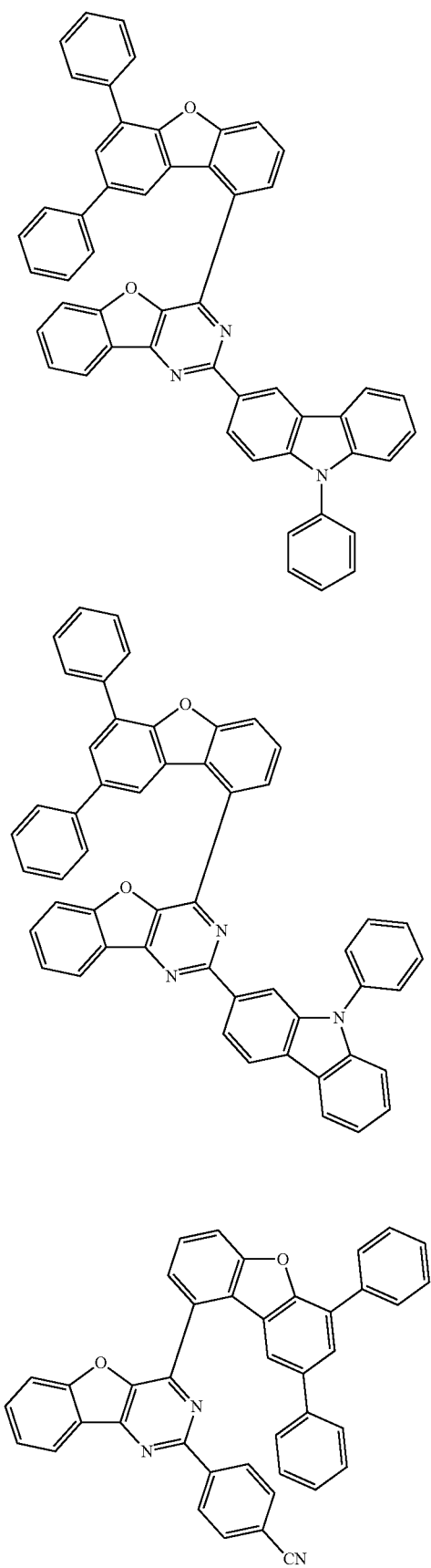
44
-continued
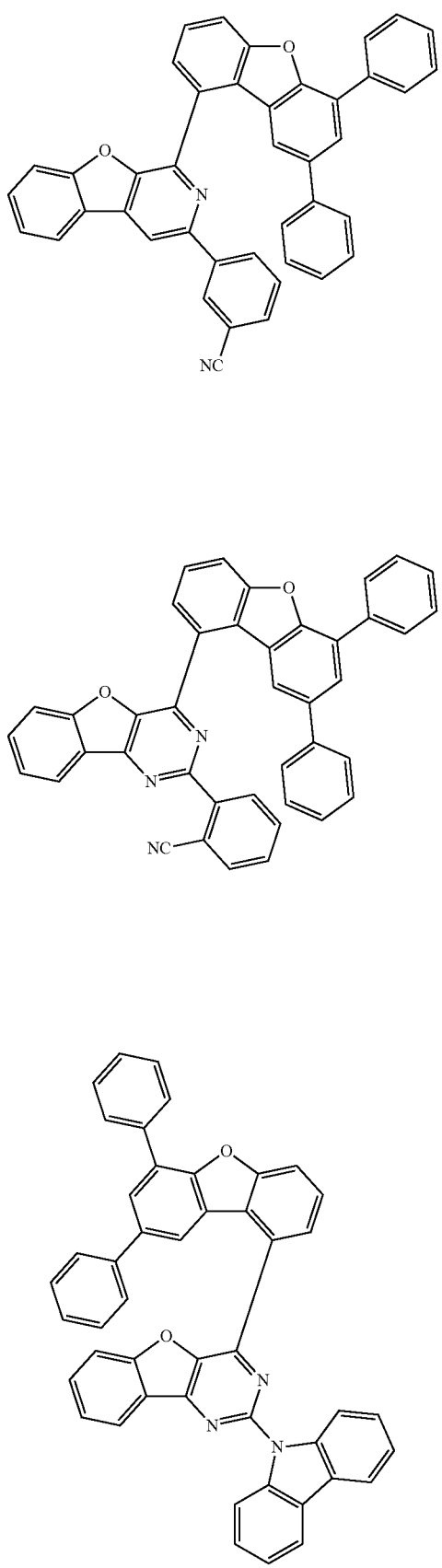

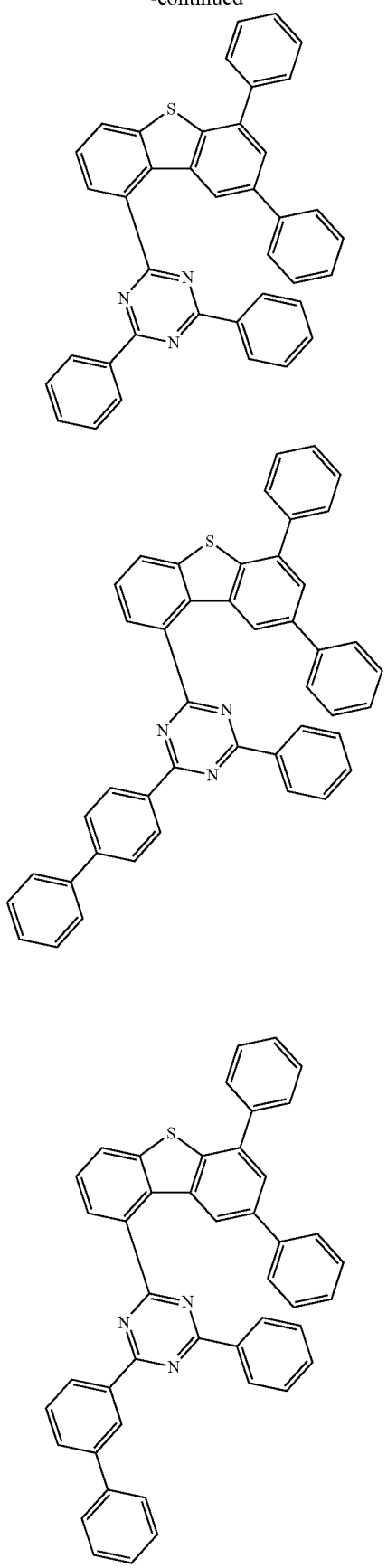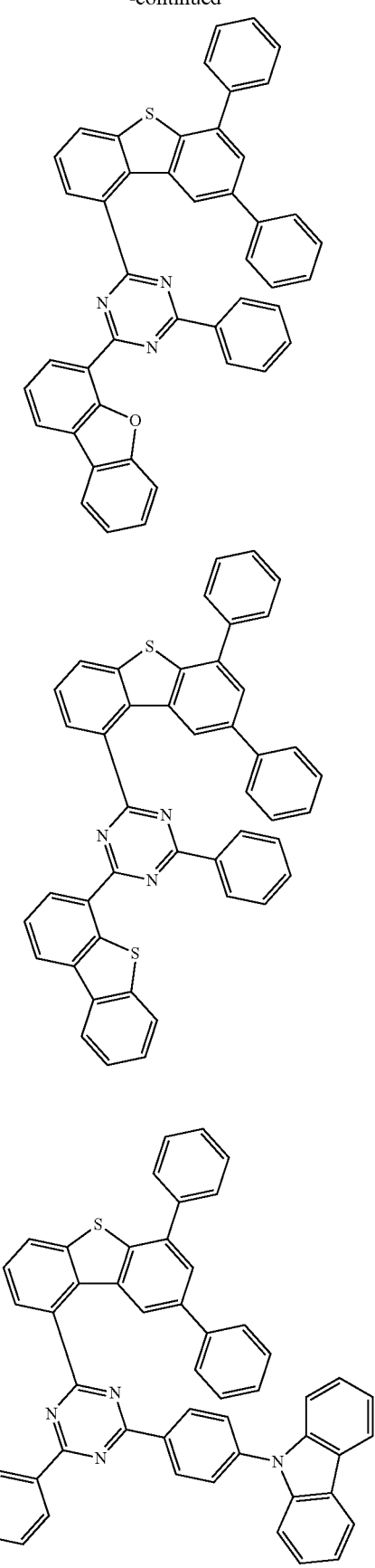

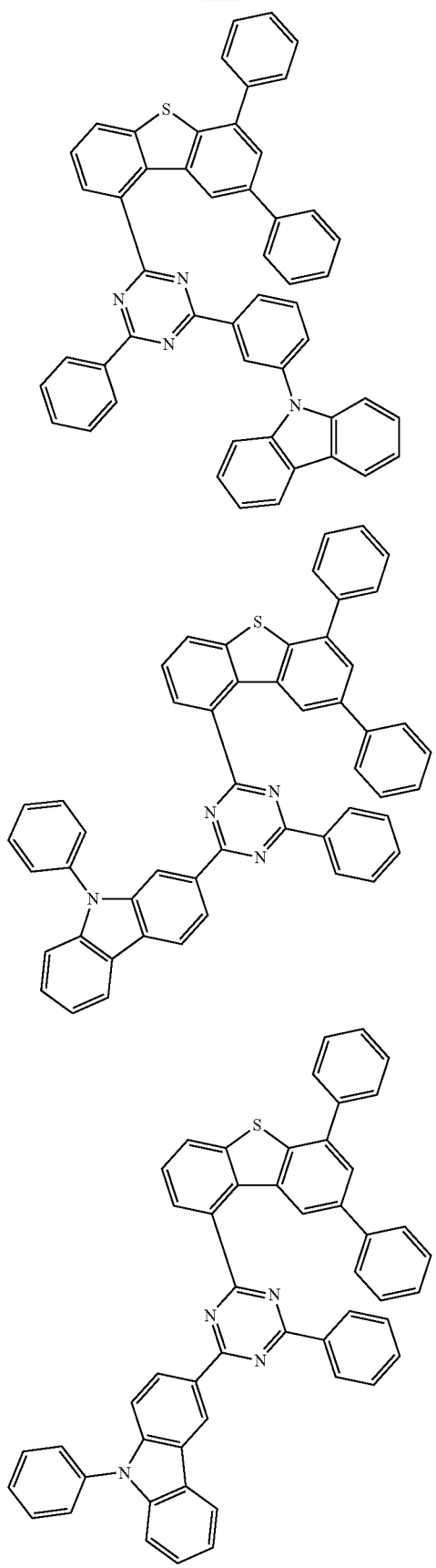
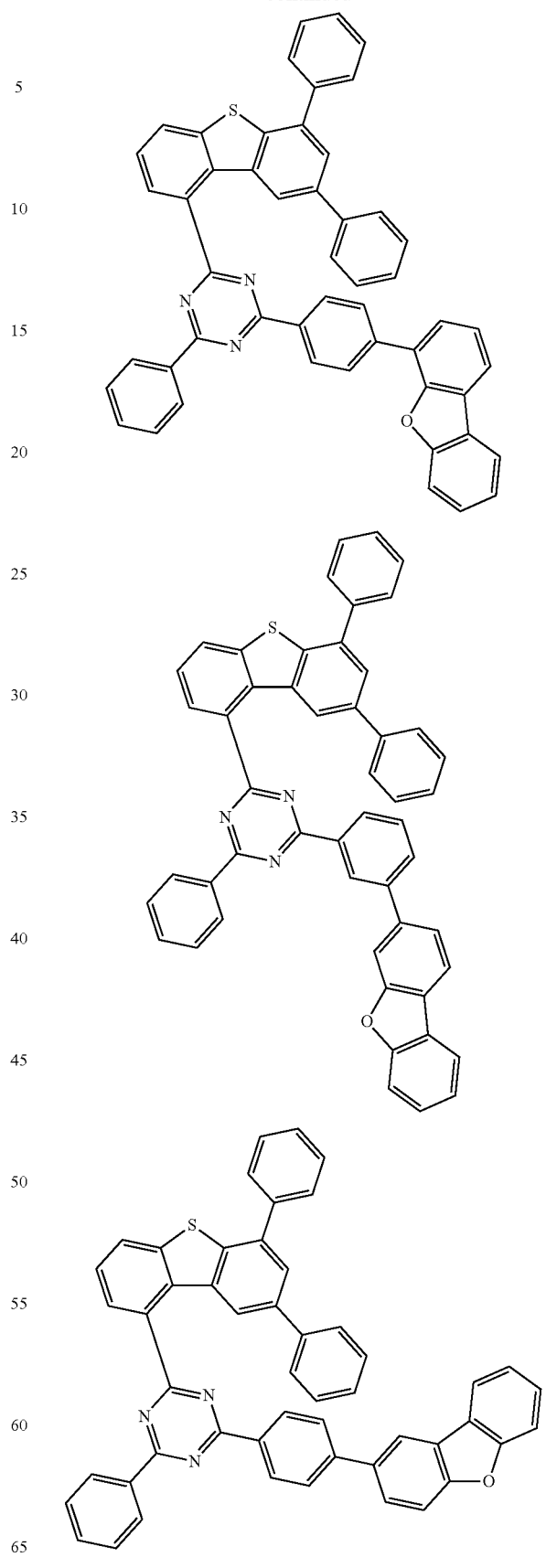

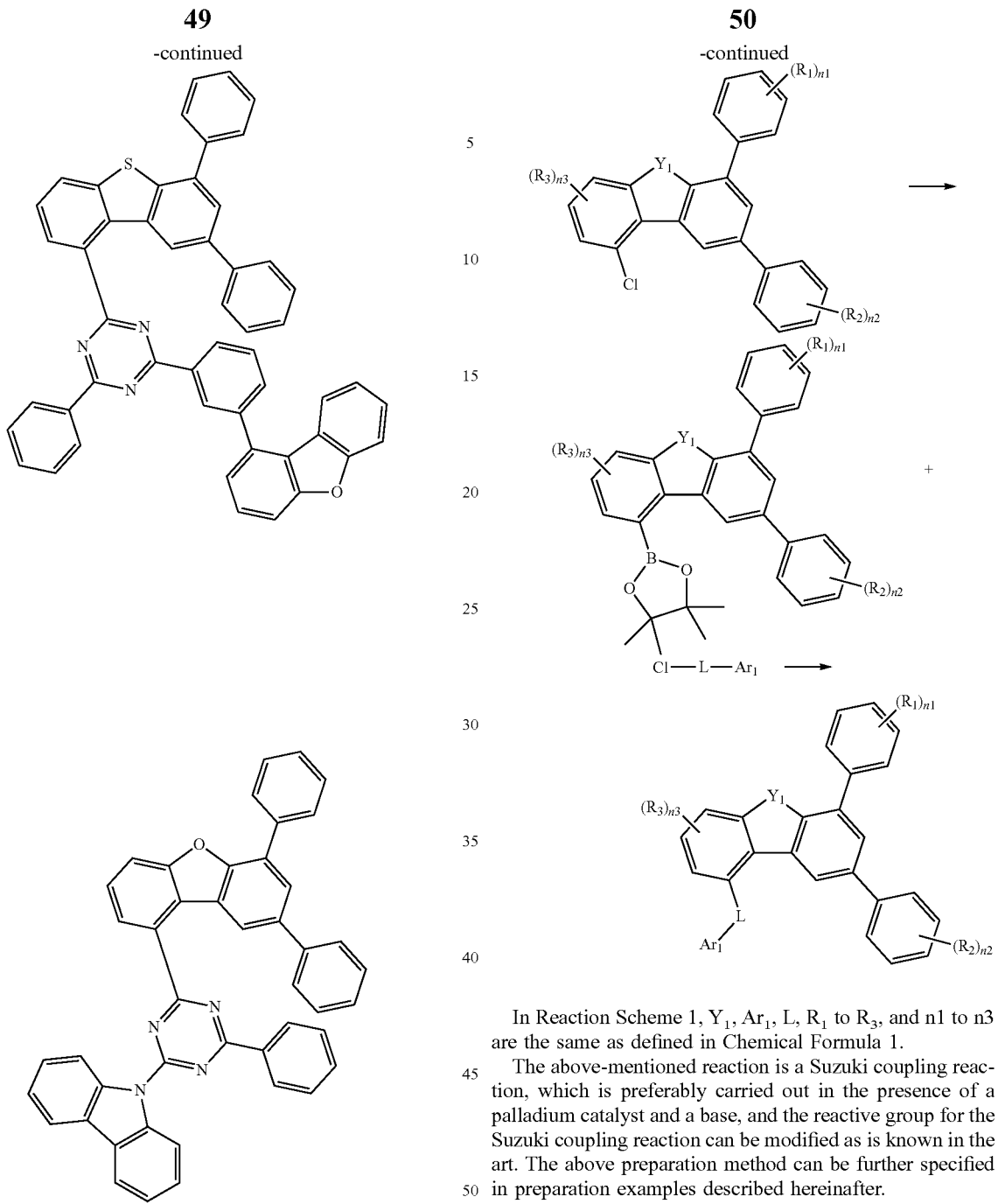

The compound of Chemical Formula 1 can be prepared, for example, according to the preparation method as shown in the following Reaction Scheme 1.

Reaction Scheme 1

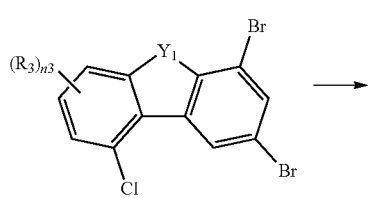

In Reaction Scheme 1, $Y_1$, $Ar_1$, L, $R_1$ to $R_3$, and n1 to n3 are the same as defined in Chemical Formula 1.

The above-mentioned reaction is a Suzuki coupling reaction, which is preferably carried out in the presence of a palladium catalyst and a base, and the reactive group for the Suzuki coupling reaction can be modified as is known in the art. The above preparation method can be further specified in preparation examples described hereinafter.

In another embodiment of the invention, an organic light emitting device including a compound of Chemical Formula 1 described above is provided. As an example, an organic light emitting device including: a first electrode; a second electrode provided opposite to the first electrode; and one or more organic material layers provided between the first electrode and the second electrode, wherein one or more layers of the organic material layers includes the compound of Chemical Formula 1, is provided.

The organic material layer of the organic light emitting device of the present invention can have a single layer structure, or it can have a multilayered structure in which two or more organic material layers are stacked. For example, the organic light emitting device of the present disclosure can have a structure including a hole injection layer, a hole transport layer, an electron blocking layer, a light emitting layer, an electron transport layer, an electron injection layer, and the like as the organic material layer. However, the structure of the organic light emitting device is not limited thereto, and it can include a smaller number of organic layers.

Specifically, the organic material layer can include a light emitting layer, wherein the light emitting layer can include a compound of Chemical Formula 1.

In this case, the compound of Chemical Formula 1 can be used as a host in a light emitting layer.

In addition, the light emitting layer can include two or more kinds of hosts. Further, one of the above hosts can be a compound of Chemical Formula 1.

Further, the organic light emitting device according to the present invention can be a normal type of organic light emitting device in which an anode, one or more organic material layers, and a cathode are sequentially stacked on a substrate. Further, the organic light emitting device according to the present disclosure can be an inverted type of organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 shows an example of an organic light emitting device including a substrate 1, an anode 2, a light emitting layer 3, and a cathode 4. In such a structure, the compound of Chemical Formula 1 can be included in the light emitting layer.

FIG. 2 shows an example of an organic light emitting device including a substrate 1, an anode 2, a hole injection layer 5, a hole transport layer 6, an electron blocking layer 7, a light emitting layer 3, an electron transport layer 8, an electron injection layer 9, and a cathode 4. In such a structure, the compound of Chemical Formula 1 can be included in one or more layers of the hole injection layer, the hole transport layer, the light emitting layer, and the electron transport layer.

The organic light emitting device according to the present invention can be manufactured by materials and methods known in the art, except that one or more layers of the organic material layers includes the compound of Chemical Formula 1. In addition, when the organic light emitting device includes a plurality of organic material layers, the organic material layers can be formed of the same material or different materials.

For example, the organic light emitting device according to the present invention can be manufactured by sequentially stacking a first electrode, an organic material layer, and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device can be manufactured by sequentially depositing a cathode material, an organic material layer, and an anode material on a substrate.

In addition, the compound of Chemical Formula 1 can be formed into an organic layer by a solution coating method as well as a vacuum deposition method at the time of manufacturing an organic light emitting device. Herein, the solution coating method means spin coating, dip coating, doctor blading, inkjet printing, screen printing, spraying, roll coating, or the like, but is not limited thereto.

In addition to such a method, the organic light emitting device can be manufactured by sequentially depositing a cathode material, an organic material layer, and an anode material on a substrate (International Publication WO2003/012890). However, the manufacturing method is not limited thereto.

As an example, the first electrode is an anode and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chromium, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb, conductive polymers such as poly(3-methylthiophene), poly[3,4-(ethylene-1,2-dioxy)thiophene] (PEDOT), polypyrrole, polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or alloys thereof, a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a hole injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrin, oligothiophene, an arylamine-based organic material, a hexanitrilehexaazatriphenylene-based organic material, a quinacridone-based organic material, a perylene-based organic material, an anthraquinone, polyaniline, and polythiophene-based conductive polymer, and the like, but are not limited thereto.

The hole transport layer is a layer that receives holes from a hole injection layer and transports the holes to the light emitting layer, and it is suitably a material having large mobility to the holes, and can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex (Alq₃), a carbazole-based compound; a dimerized styryl compound; BAlq; a 10-hydroxybenzoquinoline-metal compound; a benzoxazole, benzothiazole, and benzimidazole-based compound; a poly(p-phenylene vinylene) (PPV)-based polymer; a spiro compound; polyfluorene, rubrene, and the like, but are not limited thereto. The light emitting layer can include a host material and a dopant material.

The host material can be a fused aromatic ring derivative, a heterocycle-containing compound, or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styryl amine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene, and the like, which have an arylamino group. The styryl amine compound is a compound where at least one arylvinyl group is substituted in a substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styryl amine, styryl diamine, styryl triamine, styryl tetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which can receive electrons well from a cathode and transfer the electrons to a light emitting layer, and has large mobility for electrons. Specific examples of the electron transport material include: an Al complex of 8-hydroxyquinoline, a complex including Alq₃, an organic radical compound, a hydroxyflavone-metal complex, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present invention can be a front emission type, a back emission type, or a double side emission type according to the used material.

In addition, the compound of Chemical Formula 1 can be included in an organic solar cell or an organic transistor in addition to an organic light emitting device.

The preparation of the compound of Chemical Formula 1 and the organic light emitting device containing the same will be described in detail in the following examples. However, these examples are presented for illustrative purposes only, and are not intended to limit the scope of the present invention.

Preparation Example 1: Preparation of Intermediate A-5

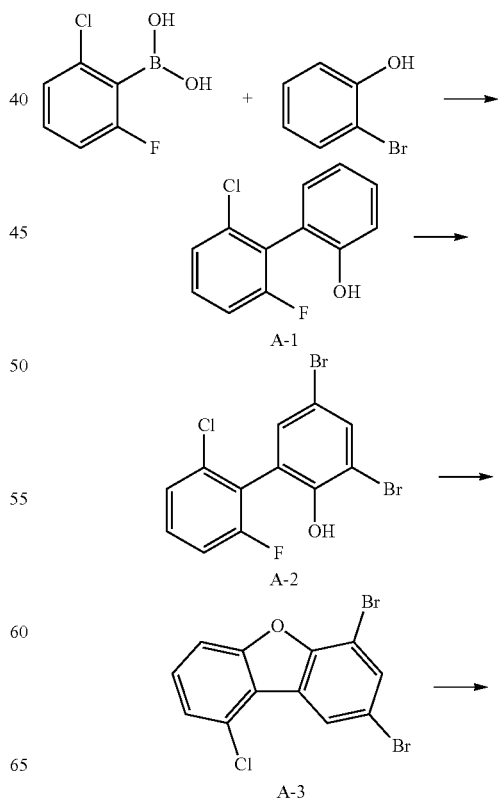

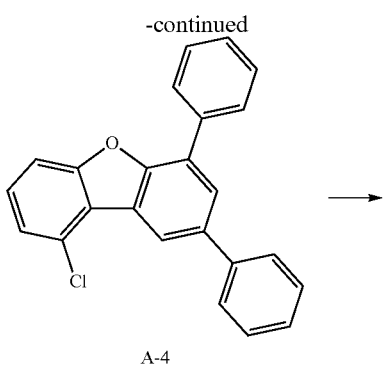

A-4

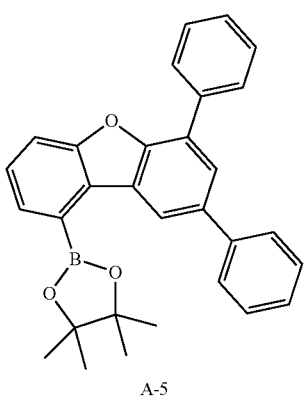

A-5

1) Synthesis of Compound A-1

2-bromophenol (49.4 g, 287.3 mmol) and 2-chloro-6-fluorophenylboronic acid (50.0 g, 287.3 mmol) were dissolved in 500 ml of tetrahydrofuran (THF). A 2M aqueous sodium carbonate solution ($Na_2CO_3$) (430 mL) and tetrakis(triphenyl-phosphine)palladium(0) [$Pd(PPh_3)_4$] (10.0 g, 8.6 mmol) were added thereto and refluxed for 12 hours. After the reaction was completed, the reaction mixture was cooled to room temperature, and the resulting mixture was extracted three times with water and toluene. The toluene layer was separated, dried over magnesium sulfate, and filtered, and the filtrate was distilled under reduced pressure. The resulting mixture was purified by column chromatography using chloroform and hexane to obtain Compound A-1 (34.4 g, yield: 54%).

MS: $[M+H]^+=223$

2) Synthesis of Compound A-2

Compound A-1 (30 g, 135.1 mmol) was dissolved in 300 ml of chloroform. N-bromosuccinimide (160.3 g, 270.25 mmol) was added thereto and stirred at room temperature for 4 hours. After the reaction was completed, water was added. After layer separation, the mixture was stirred twice with a sodium thiosulfate solution and the layer was separated. Then, distillation was carried out to obtain Compound A-2 (51.1 g, yield: 100%).

MS: $[M+H]^+=379$

3) Synthesis of Compound A-3

Compound A-2 (51.1 g, 135.1 mmol) was dissolved in distilled dimethylformamide (DMF) (400 ml). This was cooled to 0° C., and sodium hydride (3.5 g, 145.9 mmol) was slowly added dropwise thereto. The mixture was stirred for 20 minutes and then stirred at 100° C. for 1 hour. After the reaction was completed, the reaction mixture was cooled to room temperature, and 100 ml of ethanol was slowly added. The mixture was distilled under reduced pressure, and the resulting mixture was recrystallized from chloroform and ethyl acetate to obtain Compound A-3 (32.9 g, yield: 68%).

MS: $[M+H]^+=359$

4) Synthesis of Compound A-4

Compound A-3 (32.9 g, 91.9 mmol) and phenylboronic acid (24.7 g, 202.3 mmol) were dissolved in 300 ml of tetrahydrofuran (THF). A 2M aqueous potassium carbonate solution ($K_2CO_3$) (140 mL) and tetrakis(triphenylphosphine)palladium(0) [$Pd(PPh_3)_4$](2.1 g, 2 mmol) were added thereto and refluxed for 6 hours. After the reaction was completed, the reaction mixture was cooled to room temperature, and the resulting mixture was extracted three times with water and toluene. The toluene layer was separated, dried over magnesium sulfate, and filtered, and the filtrate was distilled under reduced pressure. The resulting mixture was purified by column chromatography using chloroform and ethyl acetate to obtain Compound A-4 (20.8 g, yield: 64%).

MS: $[M+H]^+=355$

5) Synthesis of Compound A-5

Compound A-4 (20.8 g, 58.7 mmol), bis(pinacolato)diboron (25.0 g, 70.6 mmol), potassium acetate (16.9 g, 176.2 mmol), bis(dibenzylideneacetone)palladium (1.0 g, 1.8 mmol), and tricyclohexylphosphine (1.0 g, 3.5 mmol) were added to dioxane (300 ml) and refluxed for 12 hours. After the reaction was completed, the reaction mixture was cooled to room temperature and distilled under reduced pressure was used to remove the solvent. This was dissolved in chloroform and washed three times with water. The organic layer was separated and dried with magnesium sulfate. This was distilled under reduced pressure to obtain Compound A-5 (25.0 g, yield: 77%).

MS: $[M+H]^+=447$

EXAMPLES

Example 1: Preparation of Compound 1

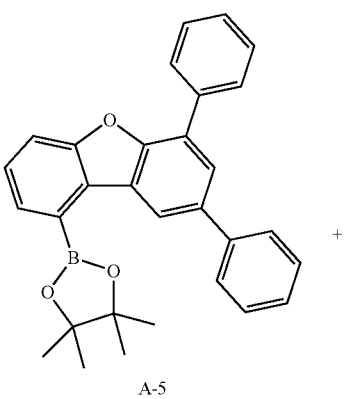

A-5

+

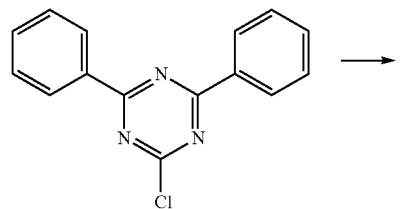

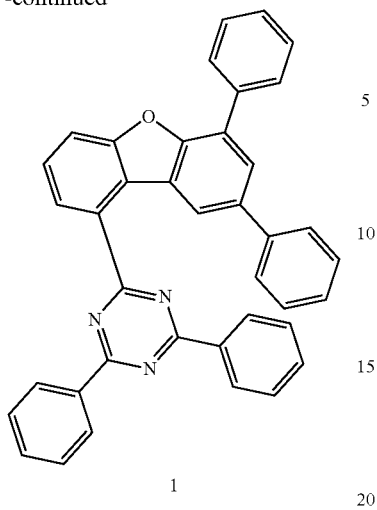

1

Compound A-5 (10 g, 22.4 mmol) and 2-chloro-4,6-diphenyl-1,3,5-triazine (6.0 g, 22.4 mmol) were added to 100 ml of tetrahydrofuran under a nitrogen atmosphere, and the mixture was stirred and refluxed. Then, potassium carbonate (9.3 g, 67 mmol) was added to and dissolved in 30 ml of water and sufficiently stirred, and to which tetrakis (triphenylphosphine)palladium(0) [Pd(PPh$_3$)$_4$] (0.5 g, 2.2 mmol) was added. After reaction for 4 hours, the reaction mixture was cooled to room temperature and filtered. The filtrate was extracted with chloroform and water, and the organic layer was dried with magnesium sulfate. Subsequently, the organic layer was distilled under reduced pressure and then recrystallized with ethyl acetate. The resulting solid was filtered then dried to prepare Compound 1 (8.7 g, 71%).

MS: [M+H]$^+$=552

Example 2: Preparation of Compound 2

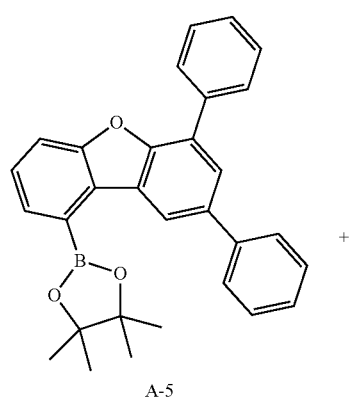

A-5

+

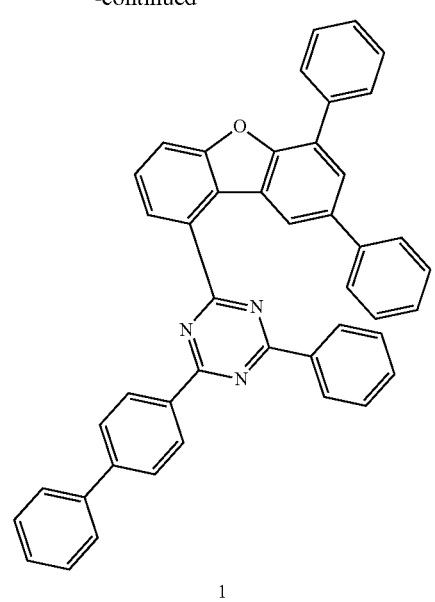

1

Compound 2 (10.8 g, 77%) was prepared in the same manner as in Example 1, except that 2-([1,1'-biphenyl]-4-yl)-4-chloro-6-phenyl-1,3,5-triazine was used instead of 2-chloro-4,6-diphenyl-1,3,5-triazine in the reaction as shown in the reaction scheme above.

MS: [M+H]$^+$=628

Example 3: Preparation of Compound 3

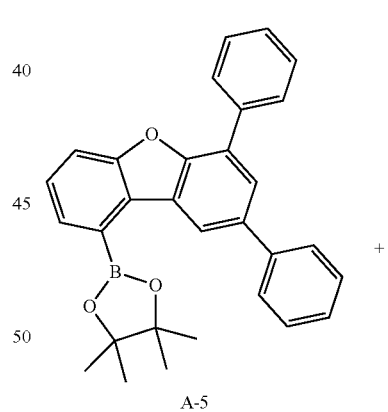

A-5

+

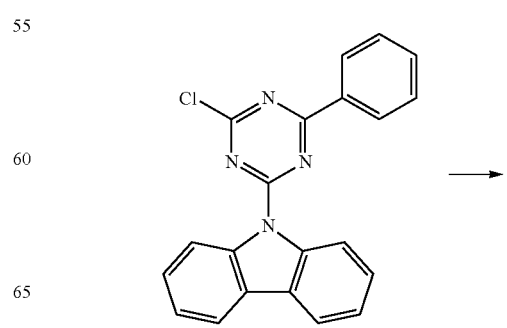

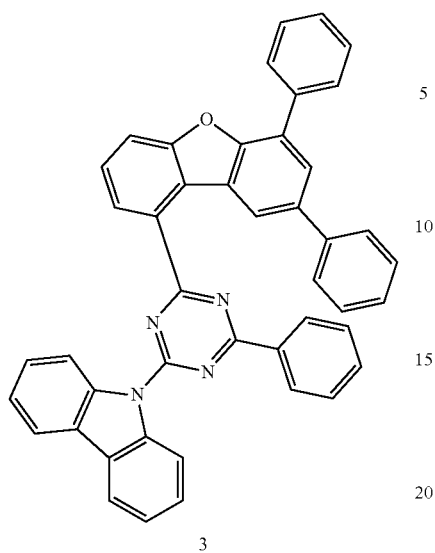

3

Compound 3 (9.5 g, 66%) was prepared in the same manner as in Example 1, except that 9-(4-chloro-6-phenyl-1,3,5-triazin-2-yl)-9H-carbazole was used instead of 2-chloro-4,6-diphenyl-1,3,5-triazine in the reaction as shown in the reaction scheme above.

MS: [M+H]$^+$=628

Example 4: Preparation of Compound 4

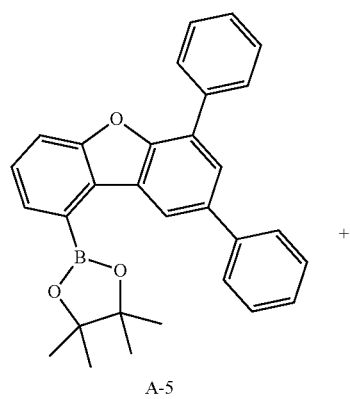

A-5

+

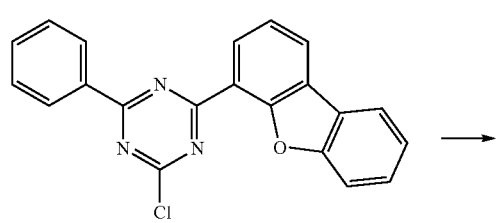

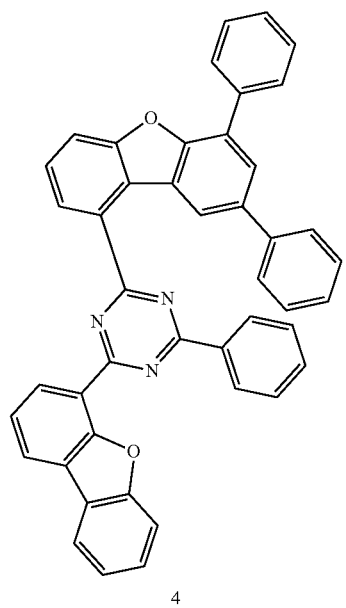

4

Compound 4 (7.4 g, 51%) was prepared in the same manner as in Example 1, except that 2-chloro-4-(dibenzo[b,d]furan-4-yl)-6-phenyl-1,3,5-triazine was used instead of 2-chloro-4,6-diphenyl-1,3,5-triazine in the reaction as shown in the reaction scheme above.

MS: [M+H]$^+$=642

Example 5: Preparation of Compound 5

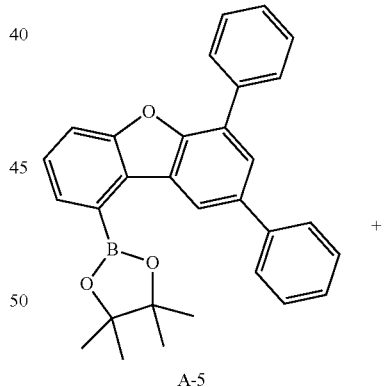

A-5

+

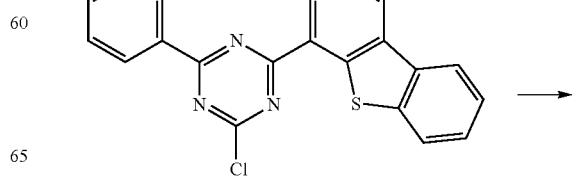

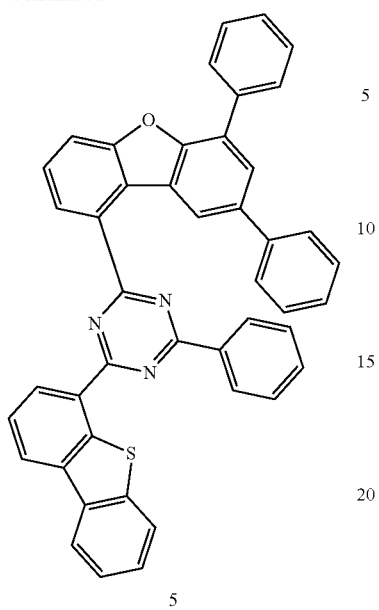

5

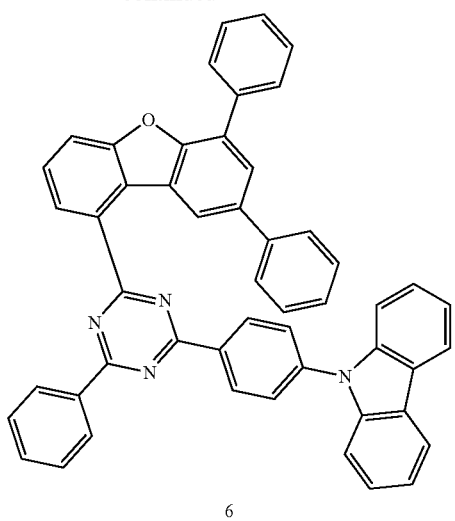

6

Compound 5 (9.3 g, 63%) was prepared in the same manner as in Example 1, except that 2-chloro-4-(dibenzo[b,d]thiophen-4-yl)-6-phenyl-1,3,5-triazine was used instead of 2-chloro-4,6-diphenyl-1,3,5-triazine in the reaction as shown in the reaction scheme above.

MS: [M+H]$^+$=658

Example 6: Preparation of Compound 6

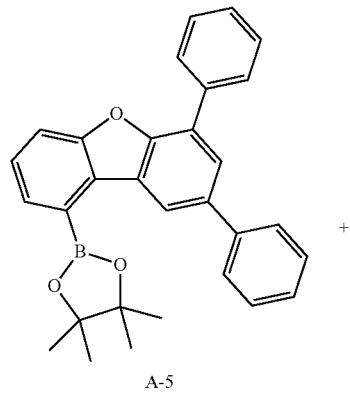

A-5

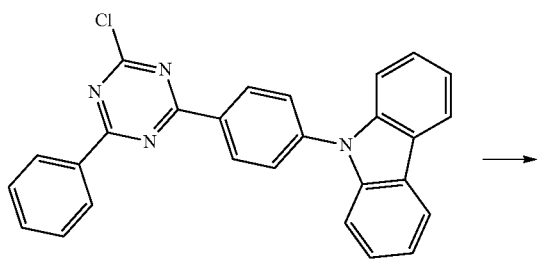

Compound 6 (13.0 g, 81%) was prepared in the same manner as in Example 1, except that 9-(4-(4-chloro-6-phenyl-1,3,5-triazine-2-yl)phenyl)-9H-carbazole was used instead of 2-chloro-4,6-diphenyl-1,3,5-triazine in the reaction as shown in the reaction scheme above.

MS: [M+H]$^+$=717

Example 7: Preparation of Compound 7

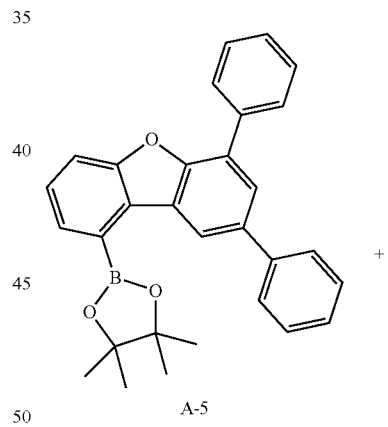

A-5

+

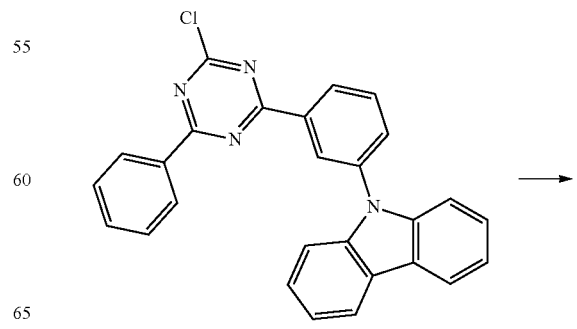

-continued

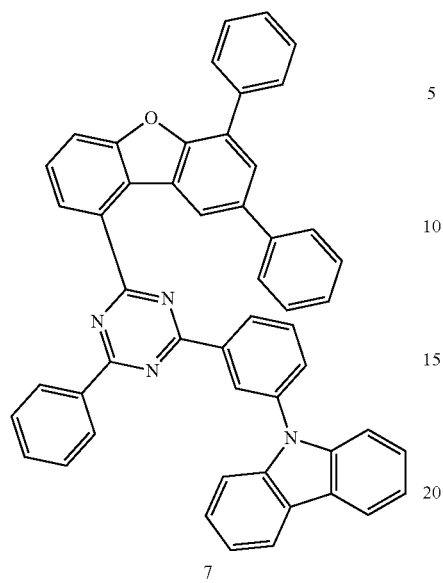

7

Compound 7 (8.5 g, 53%) was prepared in the same manner as in Example 1, except that 9-(3-(4-chloro-6-phenyl-1,3,5-triazine-2-yl)phenyl)-9H-carbazole was used instead of 2-chloro-4,6-diphenyl-1,3,5-triazine in the reaction as shown in the reaction scheme above.

MS: [M+H]⁺=717

Example 8: Preparation of Compound 8

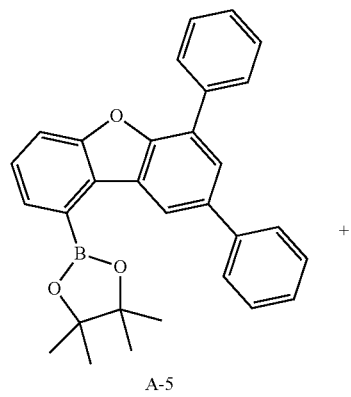

A-5

+

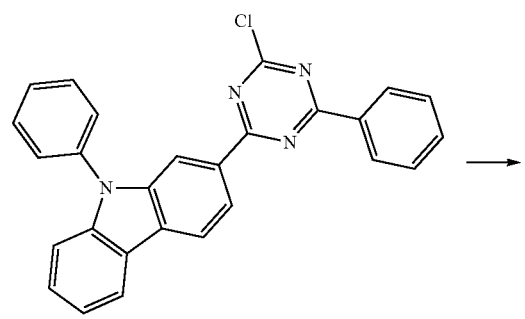

-continued

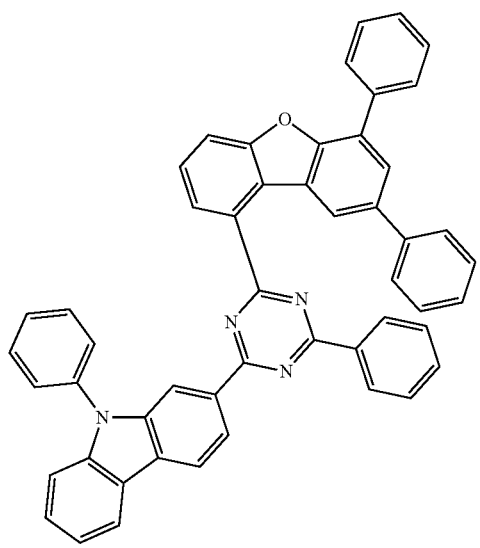

8

Compound 8 (9.5 g, 59%) was prepared in the same manner as in Example 1, except that 2-(4-chloro-6-phenyl-1,3,5-triazine-2-yl)-9-phenyl-9H-carbazole was used instead of 2-chloro-4,6-diphenyl-1,3,5-triazine in the reaction as shown in the reaction scheme above.

MS: [M+H]⁺=717

Example 9: Preparation of Compound 9

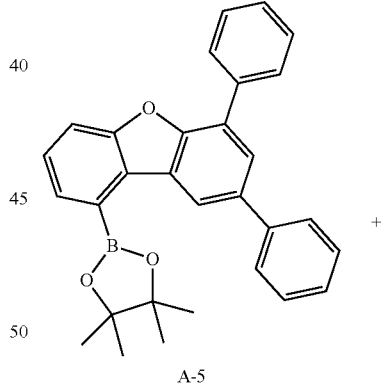

A-5

+

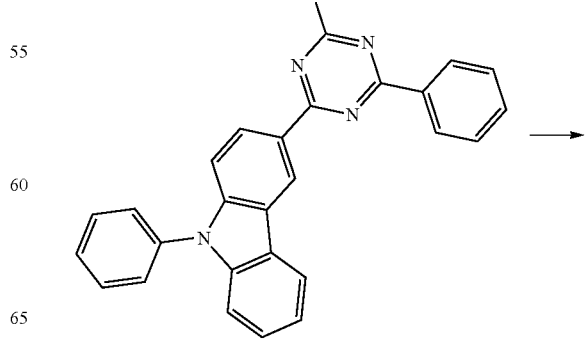

-continued

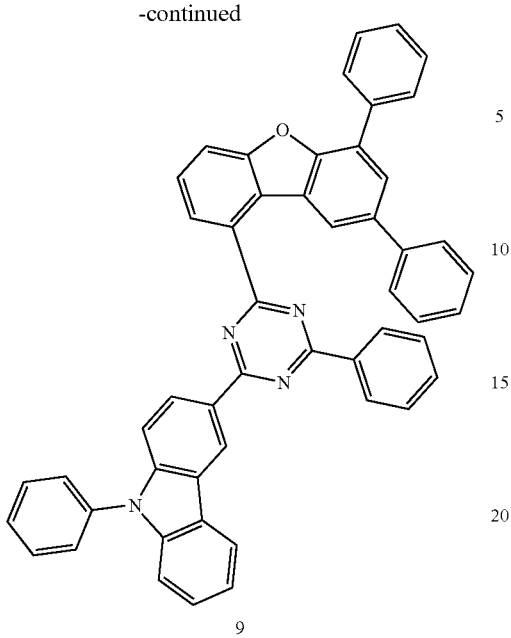

9

Compound 9 (11.9 g, 74%) was prepared in the same manner as in Example 1, except that 3-(4-chloro-6-phenyl-1,3,5-triazine-2-yl)-9-phenyl-9H-carbazole was used instead of 2-chloro-4,6-diphenyl-1,3,5-triazine in the reaction as shown in the reaction scheme above.

MS: [M+H]$^+$=717

EXPERIMENTAL EXAMPLES

Experimental Example 1

A glass substrate on which ITO (indium tin oxide) was coated as a thin film to a thickness of 1300 Å was put into distilled water in which a detergent was dissolved, and ultrasonically cleaned. In this case, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, then dried, and then transferred to a plasma cleaner. The substrate was cleaned for 5 minutes using oxygen plasma, and then transferred to a vacuum depositor.

On the ITO transparent electrode thus prepared, the following compound HI-1 was thermally vacuum deposited to a thickness of 50 Å to form a hole injection layer. The following compound HT-1 was vacuum deposited on the hole injection layer to a thickness of 250 Å to form a hole transport layer, and the following compound HT-2 was vacuum deposited on the hole transport layer to a thickness of 50 Å to form an electron blocking layer. Then, the compound 1 prepared in the previous Example 1, the following compound YGH-1, and phosphorescent dopant YGD-1 were co-deposited at a weight ratio of 44:44:12 on the electron blocking layer to form a light emitting layer with a thickness of 400 Å. The following compound ET-1 was vacuum deposited on the light emitting layer to a thickness of 250 Å to form an electron transport layer, and the following compound ET-2 and Li were vacuum deposited at a weight ratio of 98:2 to form an electron injection layer with a thickness of 100 Å. Aluminum was deposited on the electron injection layer to a thickness of 1000 Å to form a cathode.

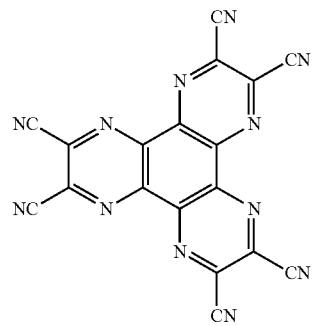

HI-1

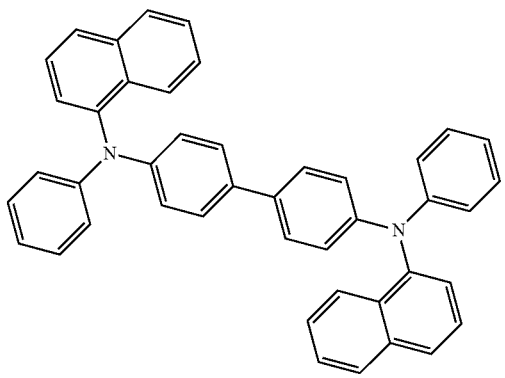

HT-1

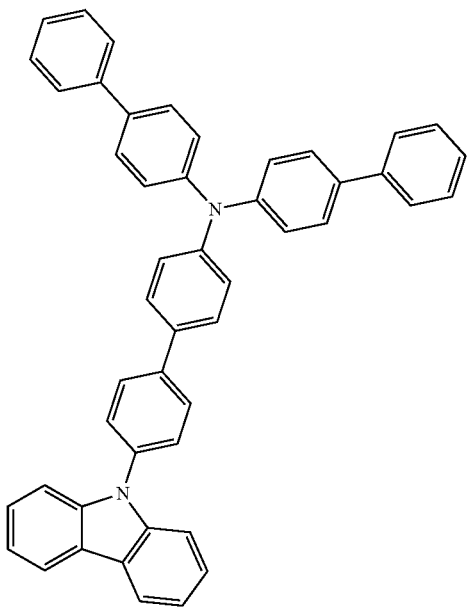

HT-2

YGH-1

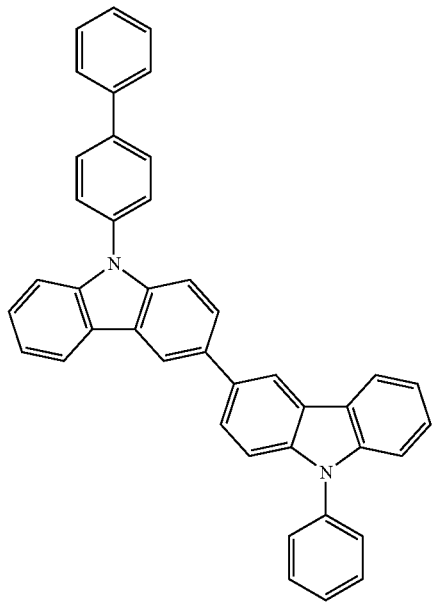

ET-2

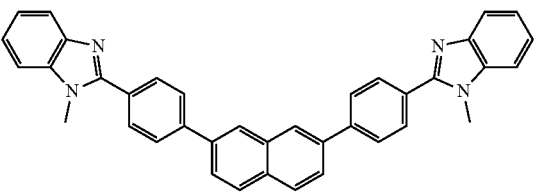

In the above-mentioned process, the vapor deposition rate of the organic material was maintained at 0.4 to 0.7 Å/s, the deposition rate of aluminum was maintained at 2 Å/s, and the degree of vacuum during the deposition was maintained at $1 \times 10^{-7}$ to $5 \times 10^{-8}$ torr.

Experimental Examples 2 to 9 and Comparative Experimental Examples 1 to 3

The organic light emitting device was manufactured in the same manner as in Experimental Example 1, except that the compounds shown in Table 1 below were used instead of the compound 1 prepared in Example 1.

The compounds of CE1, CE2, and CE3 in Table 1 below are as follows:

YGD-1

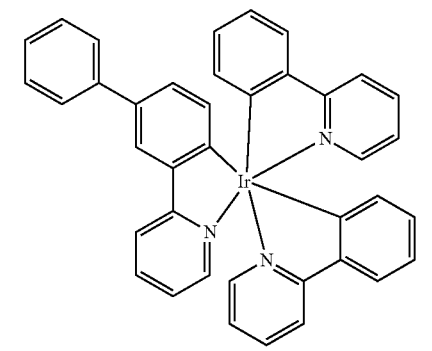

CE1

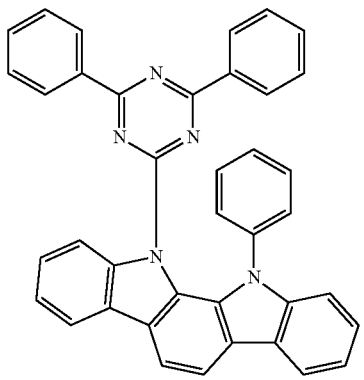

ET-1

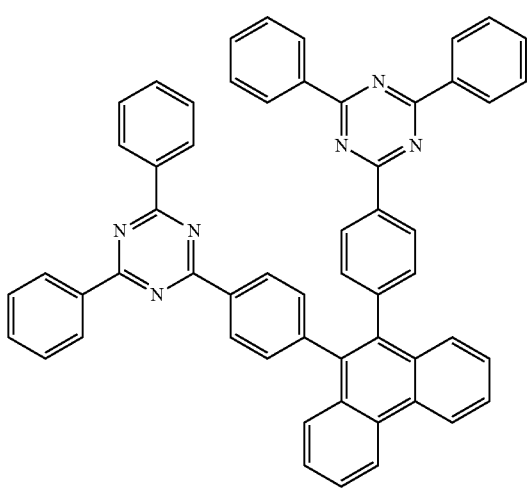

CE2

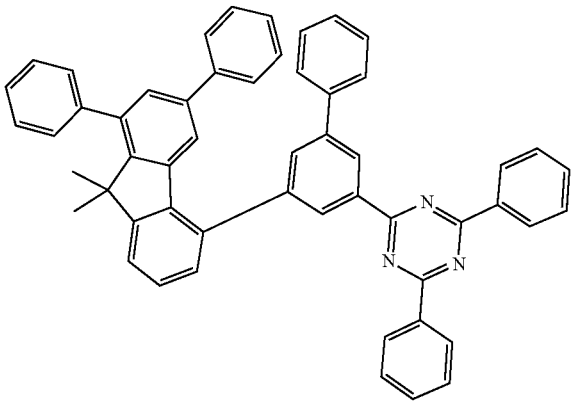

-continued

CE3

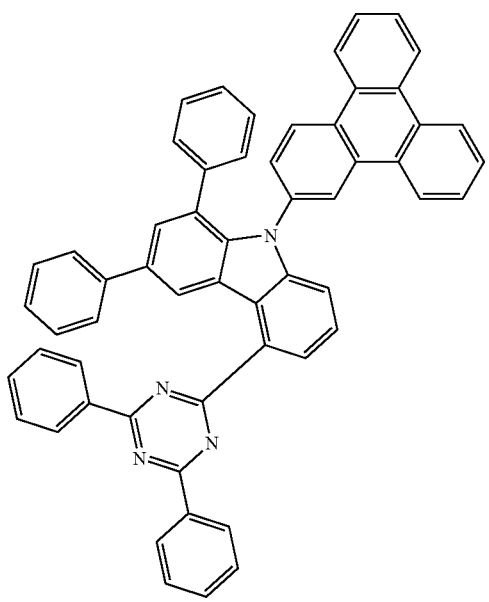

The voltage and efficiency were measured at a current density of 10 mA/cm² for the organic light emitting devices manufactured in the experimental examples and comparative experimental examples above, and the lifetime was measured at a current density of 50 mA/cm². The results are shown in Table 1 below. At this time, $LT_{95}$ means the time required for the luminance to be reduced to 95% of the initial luminance.

TABLE 1

| | Compound | Voltage (V) (@10 mA/cm²) | Efficiency (Cd/A) (@10 mA/cm²) | Color coordinate (x, y) | Lifetime (h) ($LT_{95}$ at 50 mA/cm²) |
|---|---|---|---|---|---|
| Experimental Example 1 | Compound 1 | 3.8 | 84 | 0.45, 0.54 | 100 |
| Experimental Example 2 | Compound 2 | 3.8 | 83 | 0.46, 0.53 | 110 |
| Experimental Example 3 | Compound 3 | 4.2 | 80 | 0.45, 0.53 | 190 |
| Experimental Example 4 | Compound 4 | 3.8 | 84 | 0.45, 0.54 | 140 |
| Experimental Example 5 | Compound 5 | 3.9 | 83 | 0.45, 0.54 | 170 |
| Experimental Example 6 | Compound 6 | 3.9 | 82 | 0.45, 0.54 | 150 |
| Experimental Example 7 | Compound 7 | 3.9 | 81 | 0.46, 0.53 | 160 |
| Experimental Example 8 | Compound 8 | 4.1 | 85 | 0.45, 0.54 | 160 |
| Experimental Example 9 | Compound 9 | 4.3 | 84 | 0.45, 0.54 | 150 |
| Comparative Experimental Example 1 | CE1 | 4.5 | 70 | 0.46, 0.54 | 80 |
| Comparative Experimental Example 2 | CE2 | 4.7 | 71 | 0.47, 0.53 | 15 |
| Comparative Experimental Example 3 | CE3 | 6.5 | 70 | 0.43, 0.53 | 5 |

Referring to Table 1 above, it was confirmed that the experimental examples in which the compound of the present invention was used as the light emitting layer material had remarkably lower voltage and superior efficiency and lifetime characteristics as compared with the comparative experimental examples. Specifically, the compounds 1 to 9 prepared in Examples 1 to 9 have the structure in which positions 2 and 4 of dibenzofuran substituents are substituted with phenyl, and thus, when used as a host of an organic light emitting device, it is predicted to be excellent in the electronic stability of the organic light emitting devices.

| EXPLANATION OF SIGNS | |
|---|---|
| 1: substrate | 2: anode |
| 3: light emitting layer | 4: cathode |
| 5: hole injection layer | 6: hole transport layer |
| 7: electron blocking layer | 8: electron transport layer |
| 9: electron injection layer | |

What is claimed is:

1. A compound of Chemical Formula 1:

Chemical Formula 1

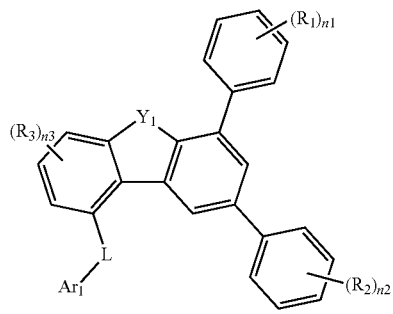

wherein, in Chemical Formula 1:

$Y_1$ is O or S;

$Ar_1$ is any one selected from the group consisting of the following:

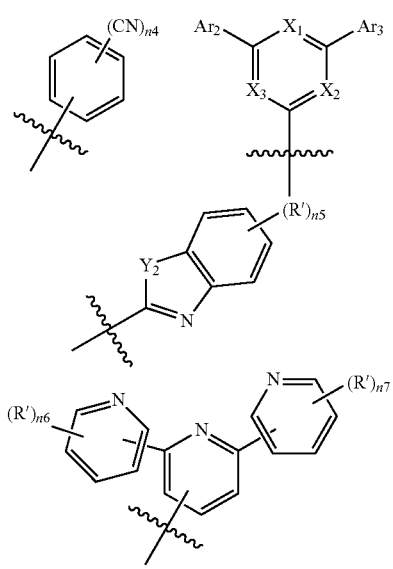

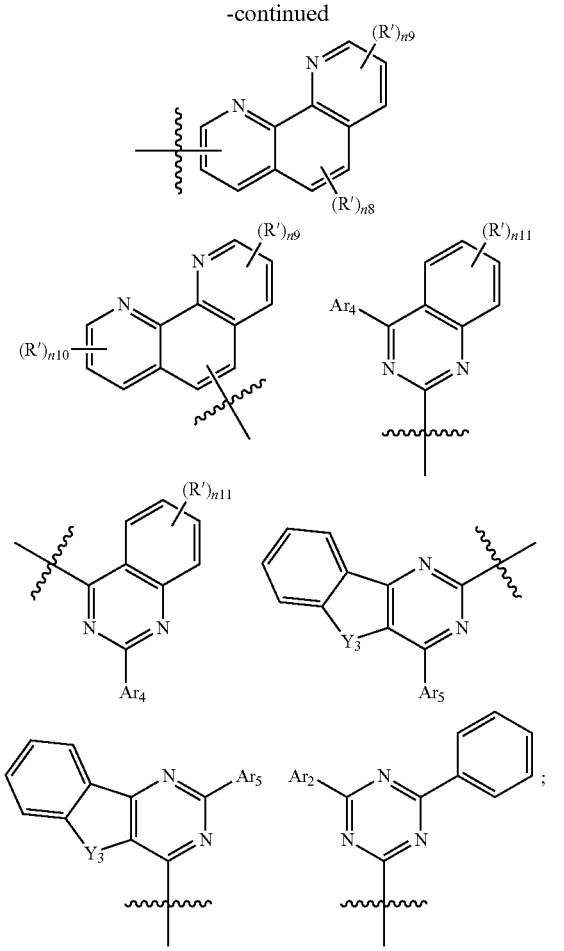

L is a single bond, a substituted or unsubstituted $C_{6-60}$ arylene, or a substituted or unsubstituted $C_{1-60}$ heteroarylene containing one or more heteroatoms selected from the group consisting of O, N, Si, and S;

$R_1$ to $R_3$ are each independently hydrogen, deuterium, a halogen, cyano, nitro, amino, a substituted or unsubstituted $C_{1-60}$ alkyl, a substituted or unsubstituted $C_{1-60}$ haloalkyl, a substituted or unsubstituted $C_{1-60}$ alkoxy, a substituted or unsubstituted $C_{1-60}$ haloalkoxy, a substituted or unsubstituted $C_{3-60}$ cycloalkyl, a substituted or unsubstituted $C_{2-60}$ alkenyl, a substituted or unsubstituted $C_{6-60}$ aryl, a substituted or unsubstituted $C_{6-60}$ aryloxy, or a substituted or unsubstituted $C_{1-60}$ heteroaryl containing one or more heteroatoms selected from the group consisting of N, O, and S; and n1 to n3 are each independently an integer of 1 to 5;

two of $X_1$ to $X_3$ are N and the remaining one is $CR'_3$;

$Y_2$ and $Y_3$ are each independently O, S, or NR';

$Ar_2$ is a $C_{6-60}$ aryl containing no heteroatoms that is unsubstituted or substituted with a group selected from the group consisting of deuterium, a halogen group, a cyano group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aralkyl group, an aralkenyl group, an alkylaryl group, an alkylamine group, an aralkylamine group, a heteroarylamine group, an arylamine group, an arylphosphine group, a heteroaryl containing at least one N atom, and an aryl group selected from among a phenyl group, a biphenyl group, a terphenyl group, a naphthyl group, an anthracenyl group, a phenanthryl group, a pyrenyl group, a perylenyl group, and a chrysenyl group; or a substituted or unsubstituted $C_{1-60}$ heteroaryl containing one or more heteroatoms selected from the group consisting of N and Si;

$Ar_3$ to $Ar_5$ are each independently a substituted or unsubstituted $C_{6-60}$ aryl or a substituted or unsubstituted $C_{1-60}$ heteroaryl containing one or more heteroatoms selected from the group consisting of O, N, Si, and S;

each R' is independently hydrogen, deuterium, a halogen, cyano, nitro, amino, a substituted or unsubstituted $C_{1-60}$ alkyl, a substituted or unsubstituted $C_{1-60}$ haloalkyl, a substituted or unsubstituted $C_{1-60}$ alkoxy, a substituted or unsubstituted $C_{1-60}$ haloalkoxy, a substituted or unsubstituted $C_{3-60}$ cycloalkyl, a substituted or unsubstituted $C_{2-60}$ alkenyl, a substituted or unsubstituted $C_{6-60}$ aryl, a substituted or unsubstituted $C_{6-60}$ aryloxy, or a substituted or unsubstituted $C_{1-60}$ heteroaryl containing one or more heteroatoms selected from the group consisting of N, O, and S; and n4 to n11 are each independently be an integer of 1 to 5.

2. The compound according to claim 1, wherein $Ar_1$ is any one selected from the group consisting of the following:

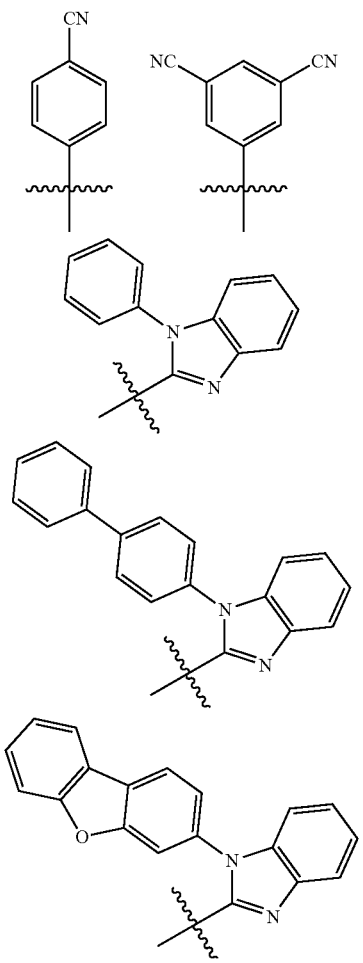

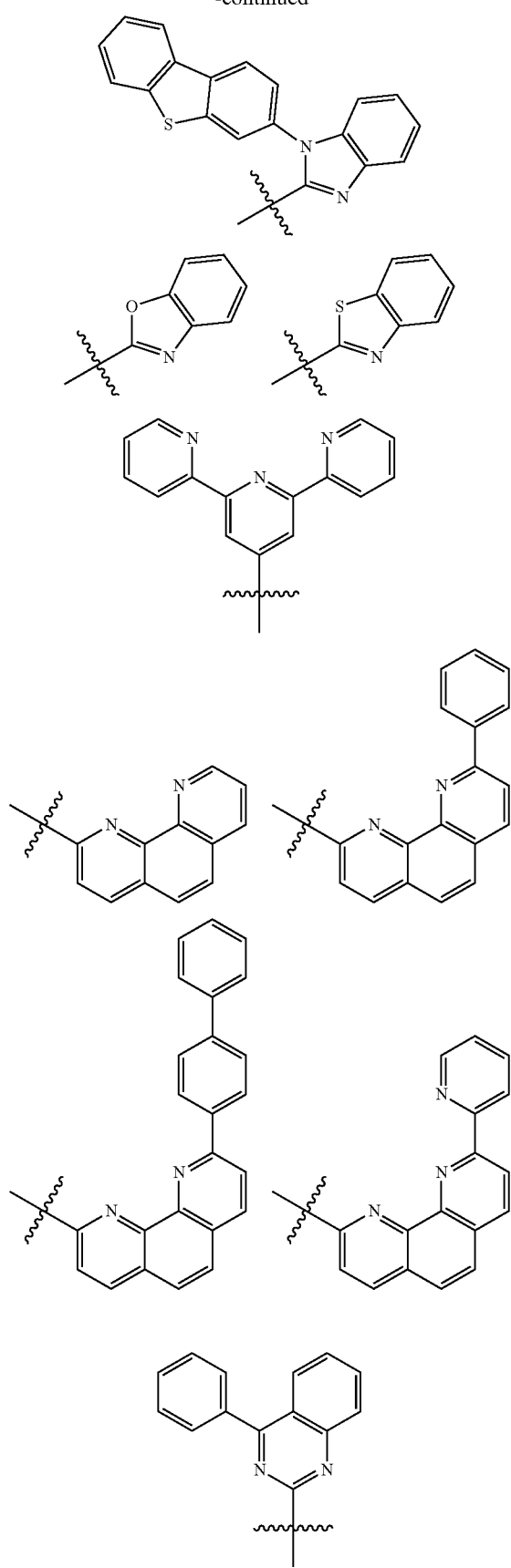
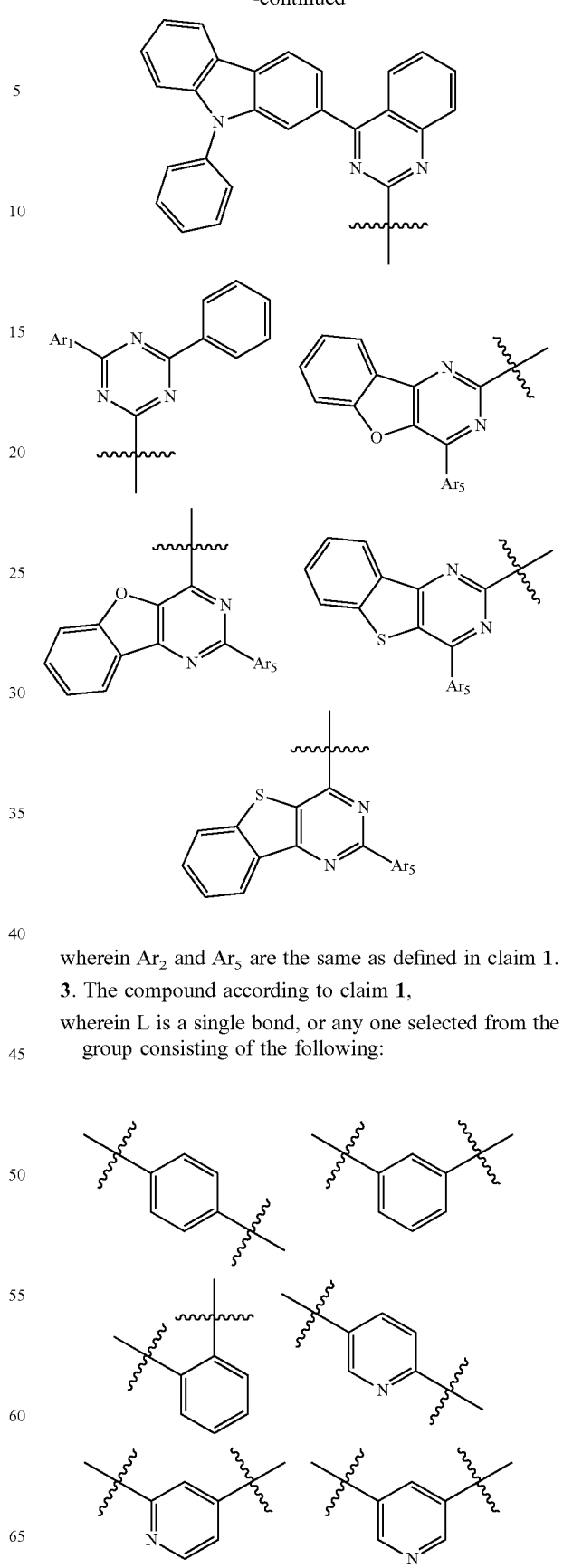
wherein $Ar_2$ and $Ar_5$ are the same as defined in claim 1.
3. The compound according to claim 1,
wherein L is a single bond, or any one selected from the group consisting of the following:
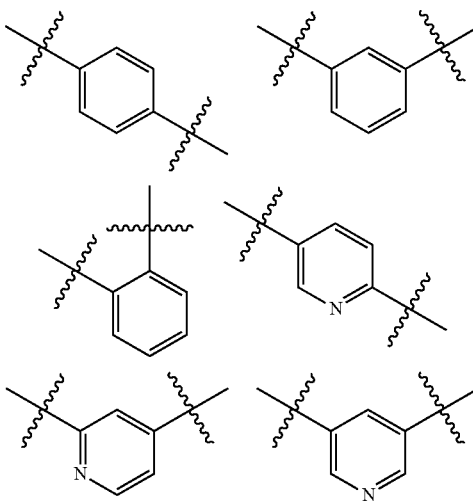

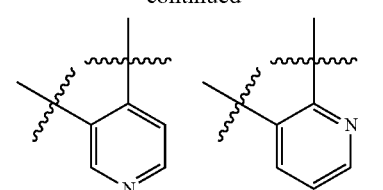
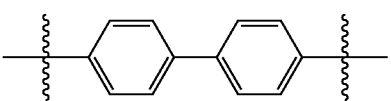
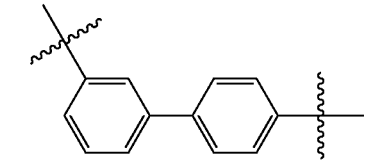
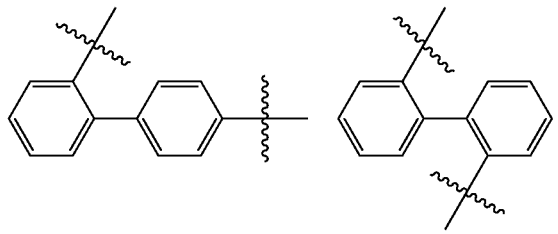
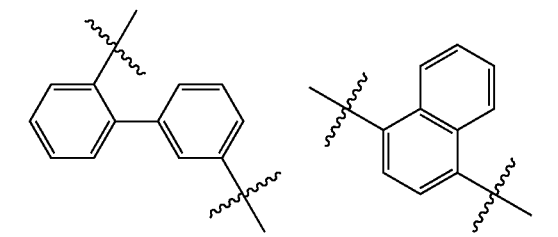
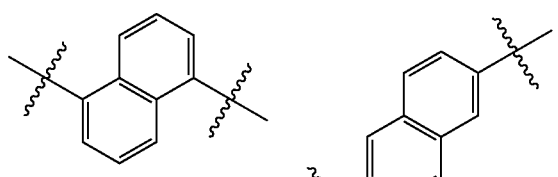
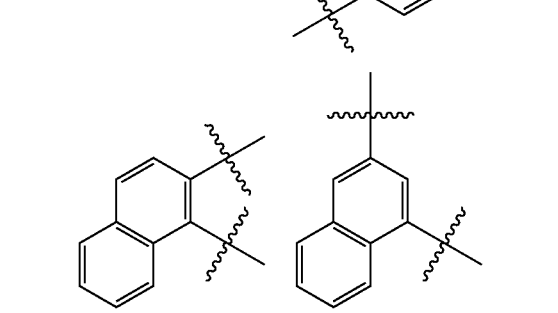
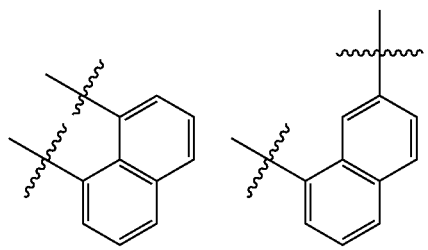
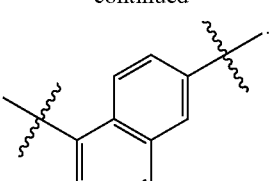
4. The compound according to claim 1,
wherein $R_1$ to $R_3$ are each independently hydrogen, deuterium, cyano, or a substituted or unsubstituted $C_{1-10}$ alkyl.
5. A compound selected from the group consisting of the following compounds:
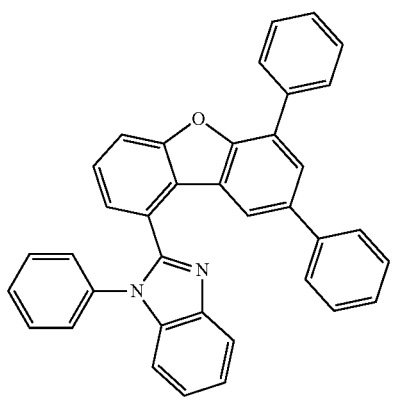
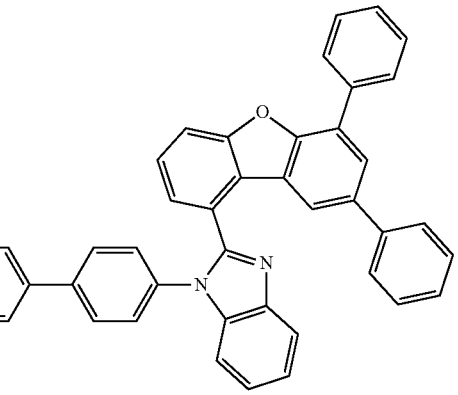
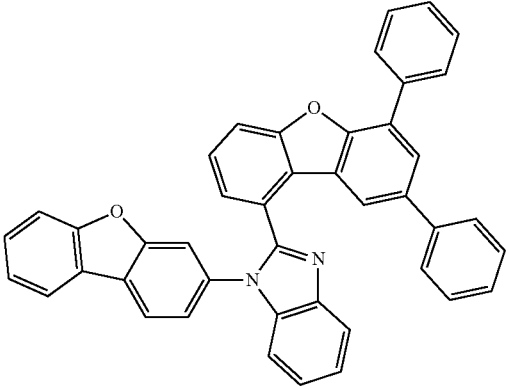

77
-continued
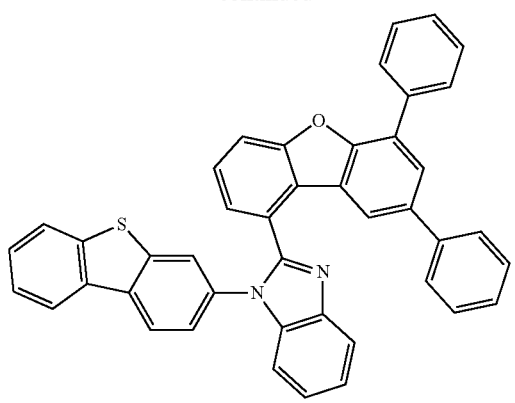
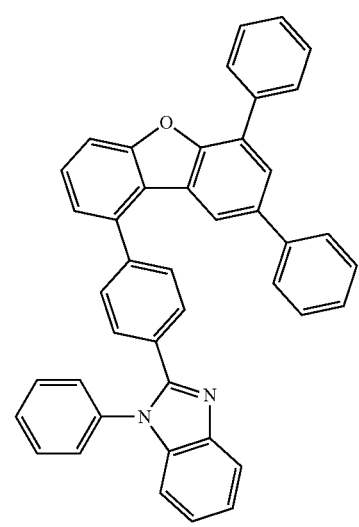
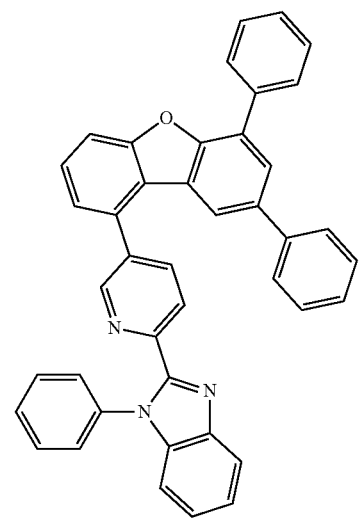
78
-continued
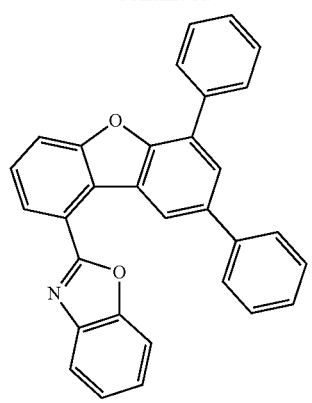
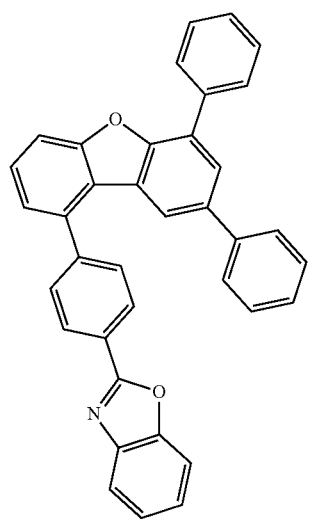
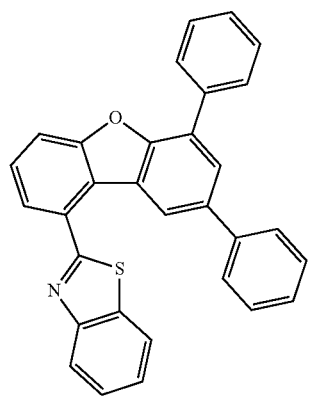

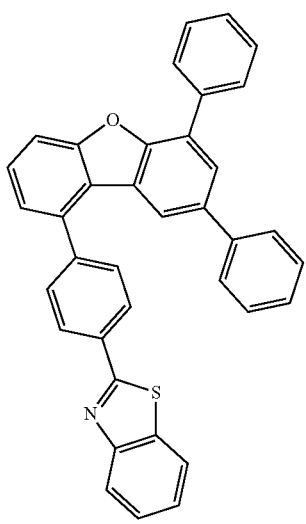
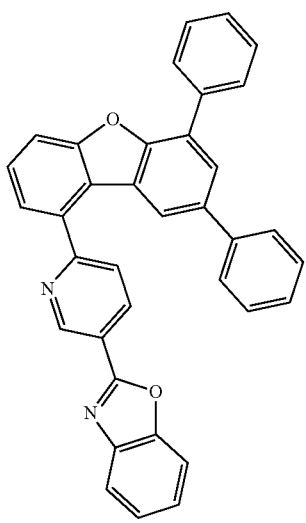
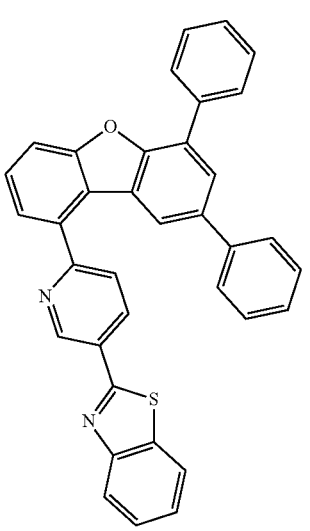
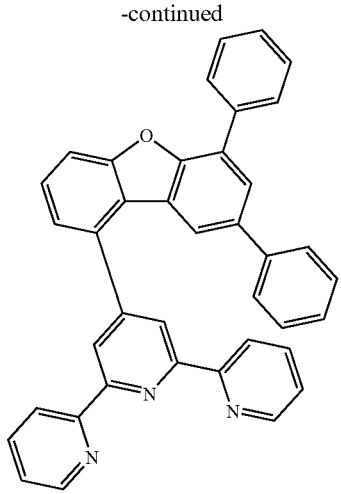
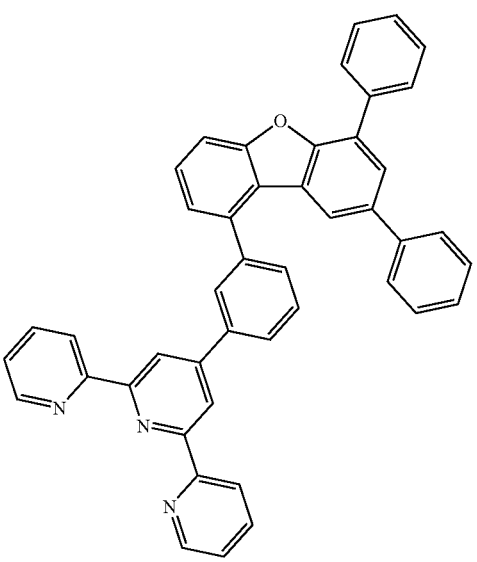
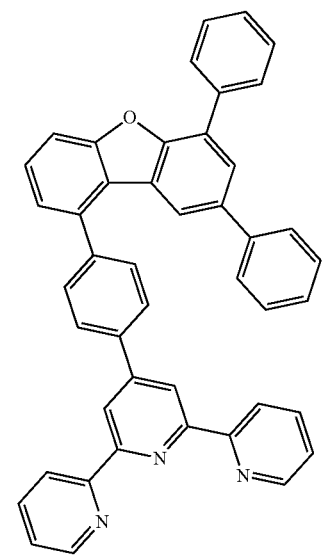

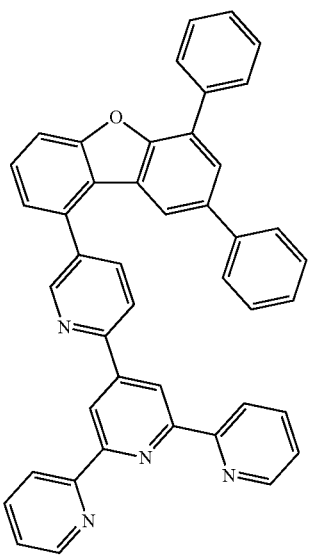
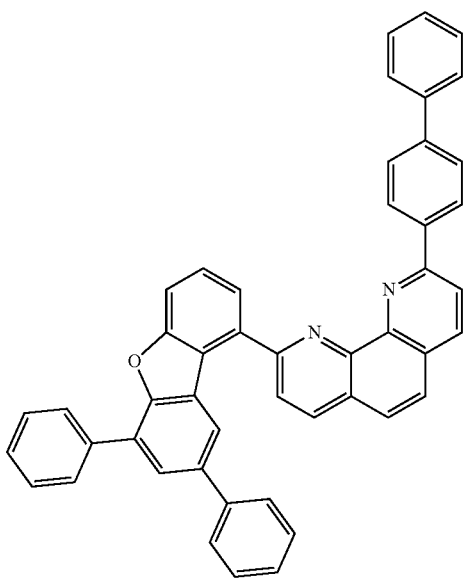
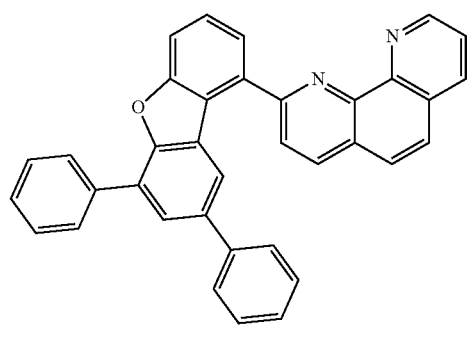
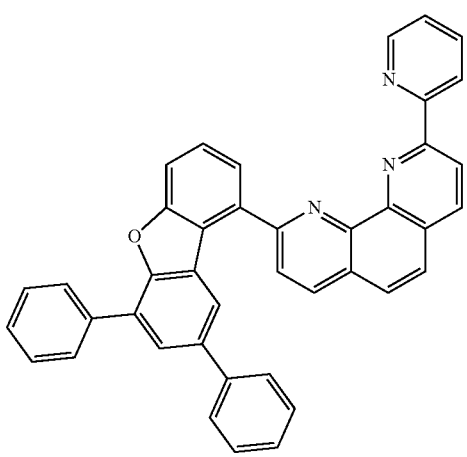
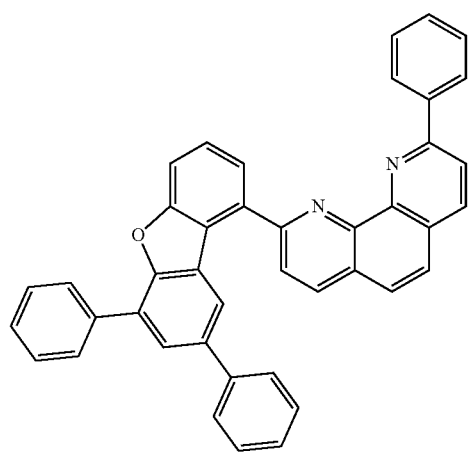
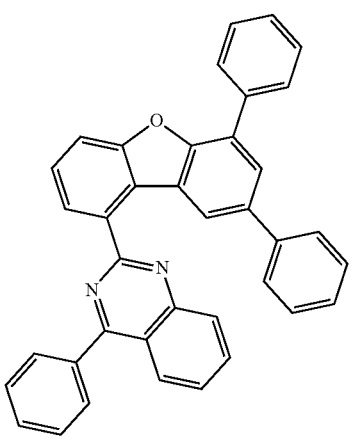

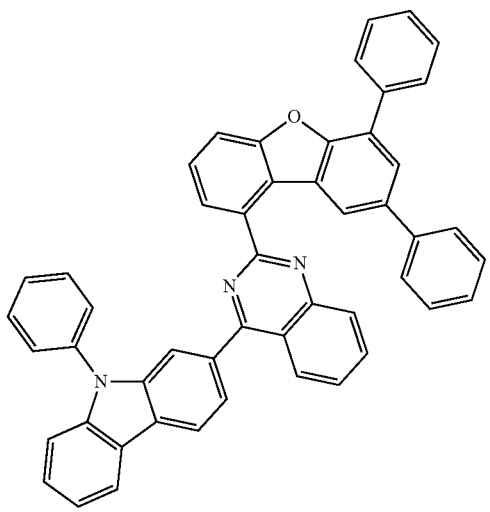
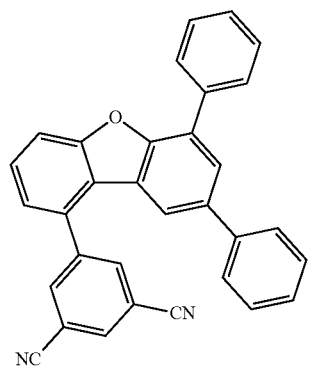
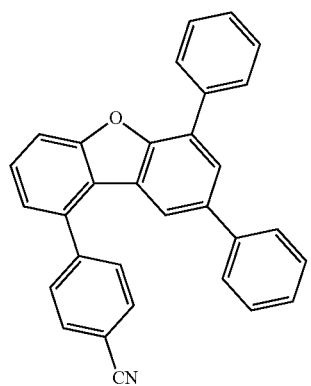
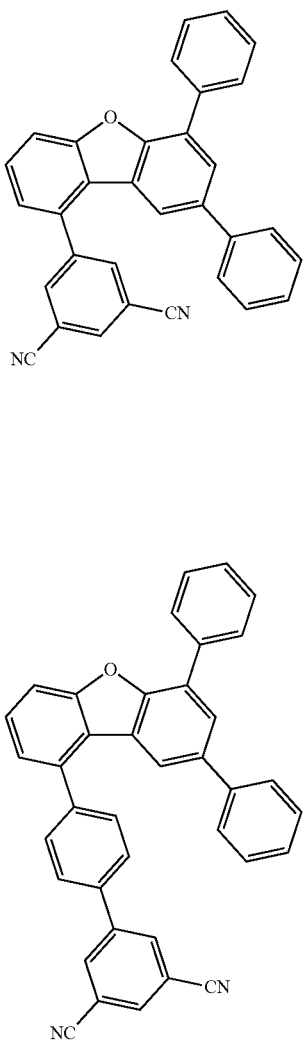
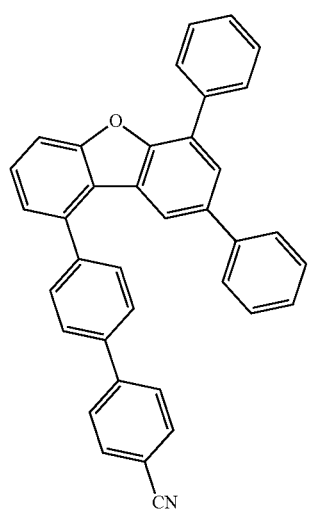
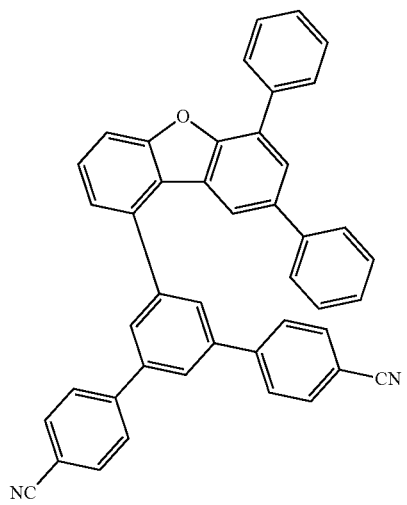

85
-continued
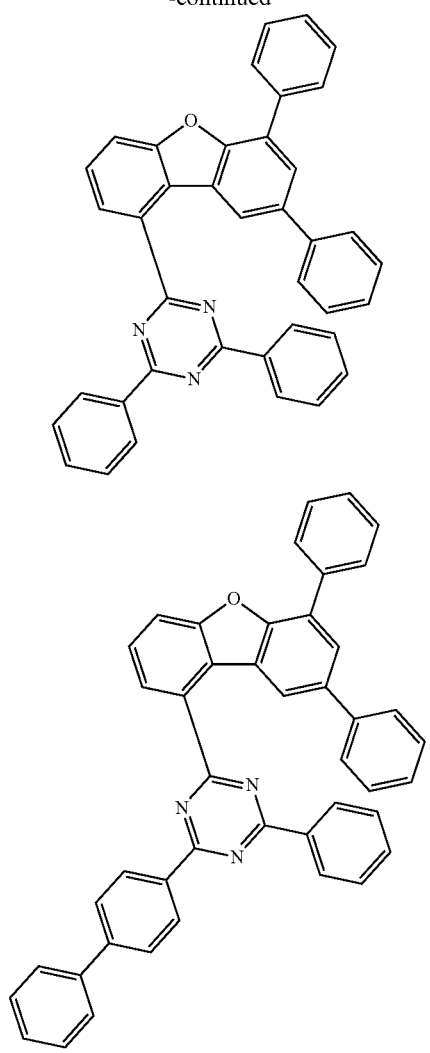
86
-continued
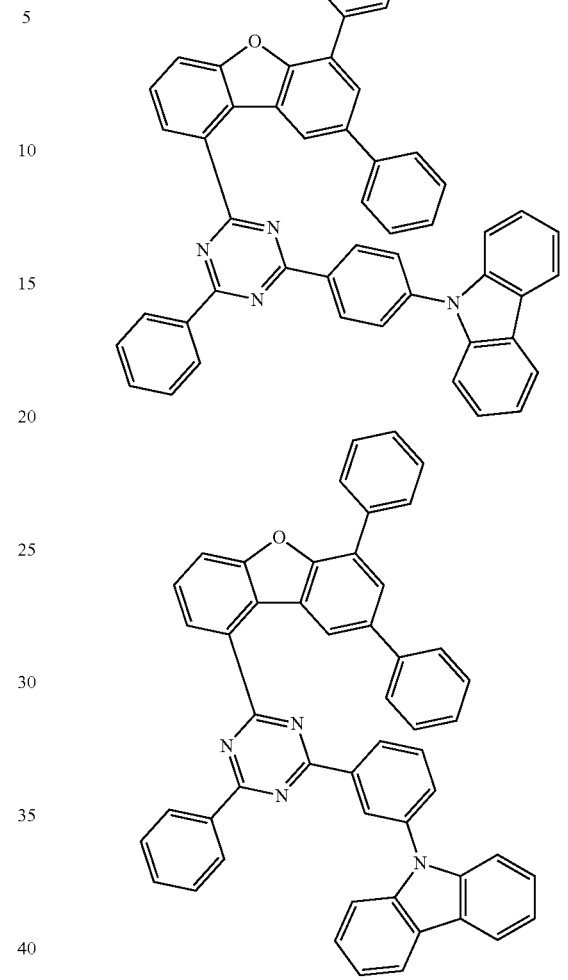
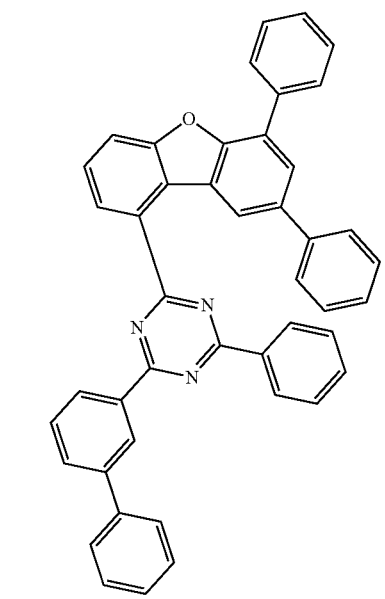
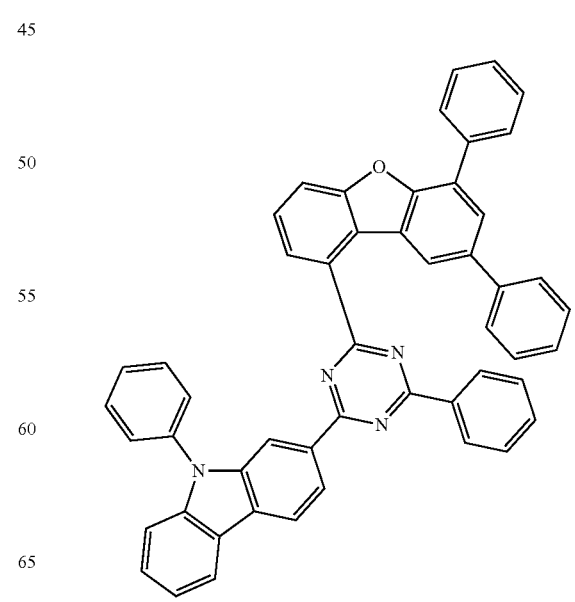

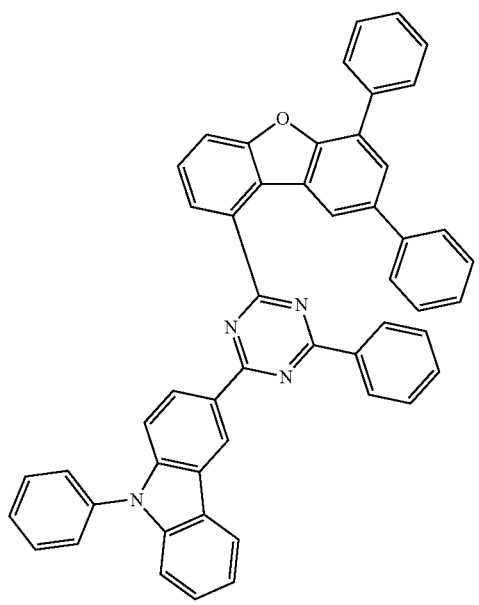
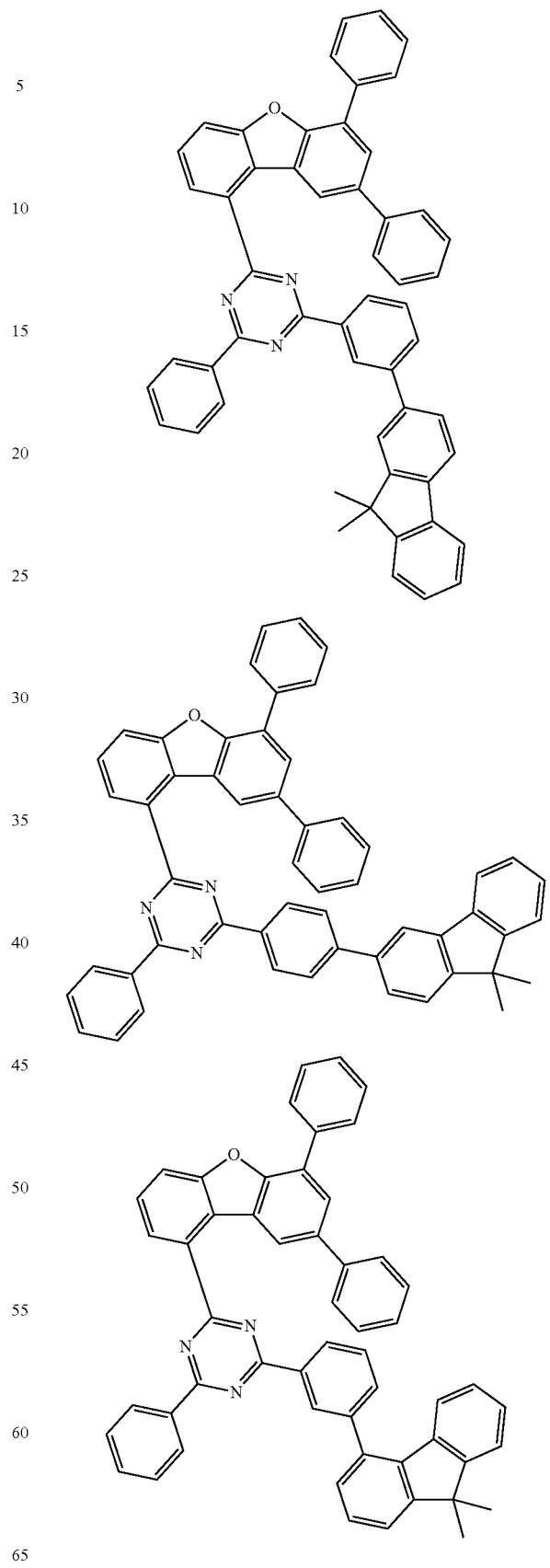

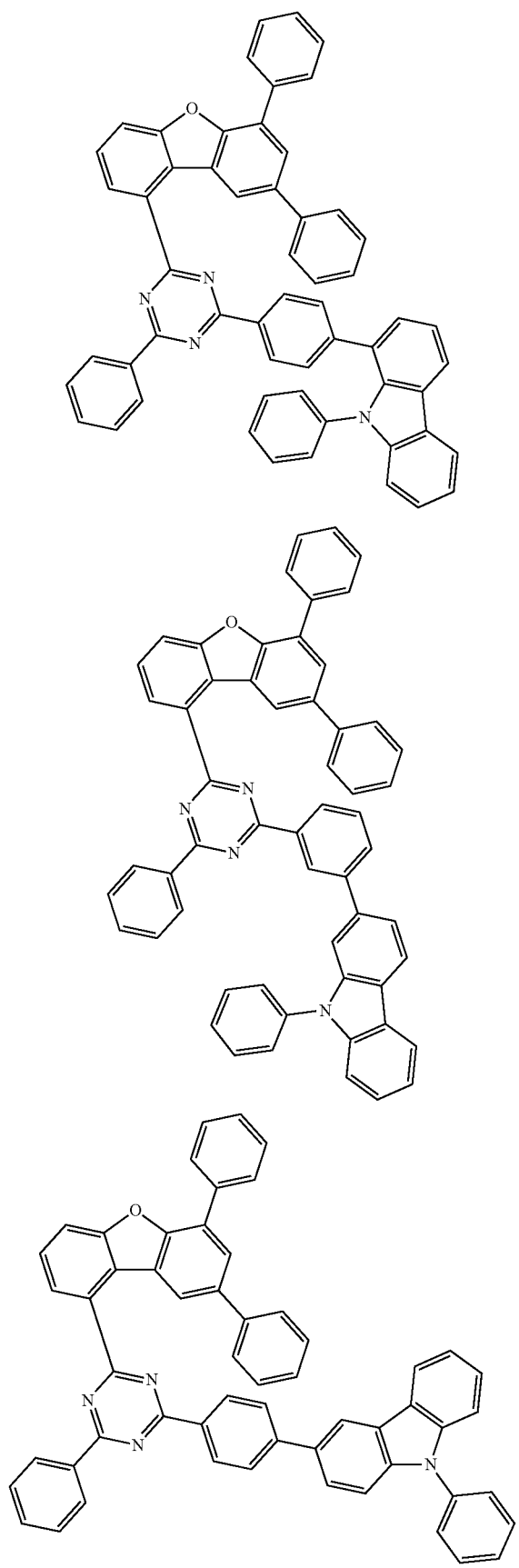
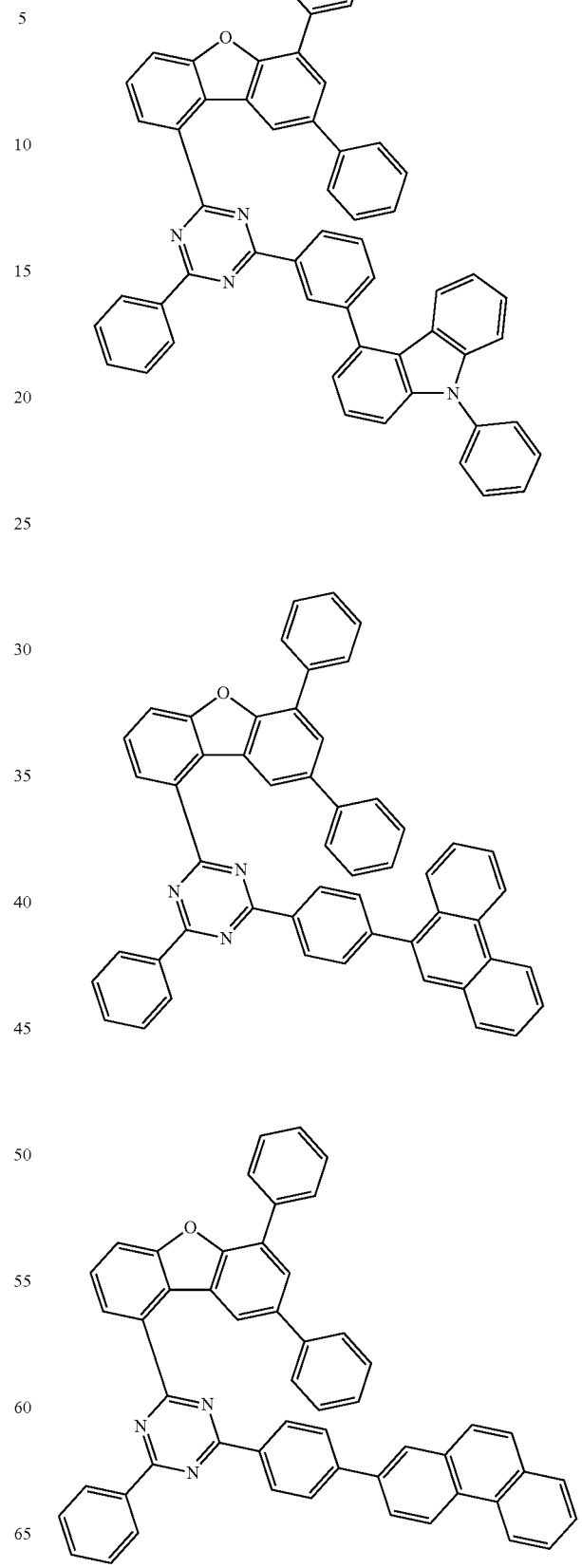

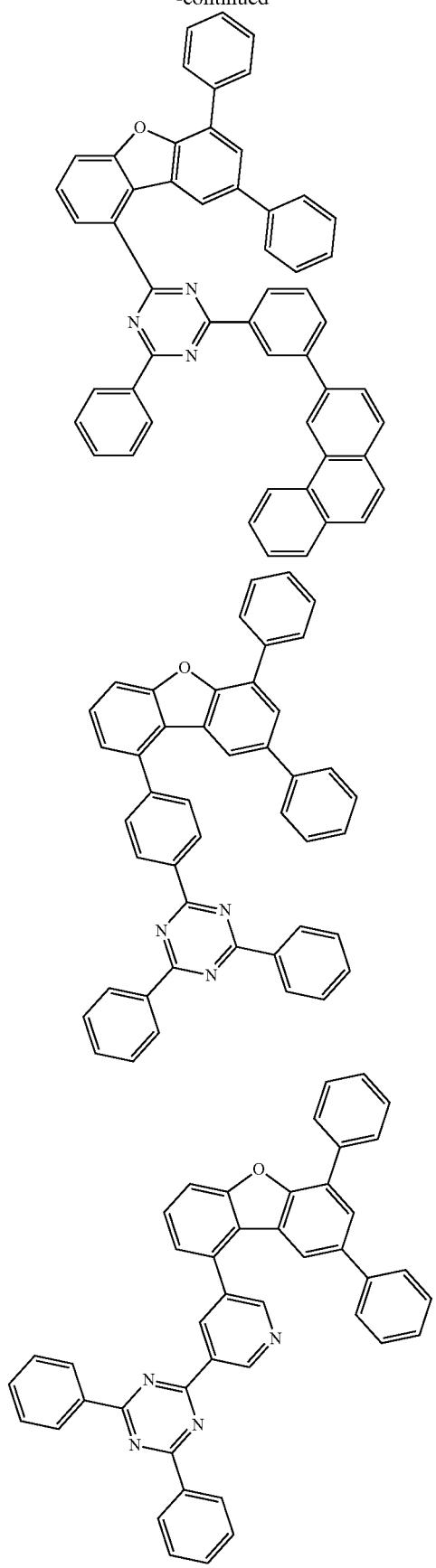
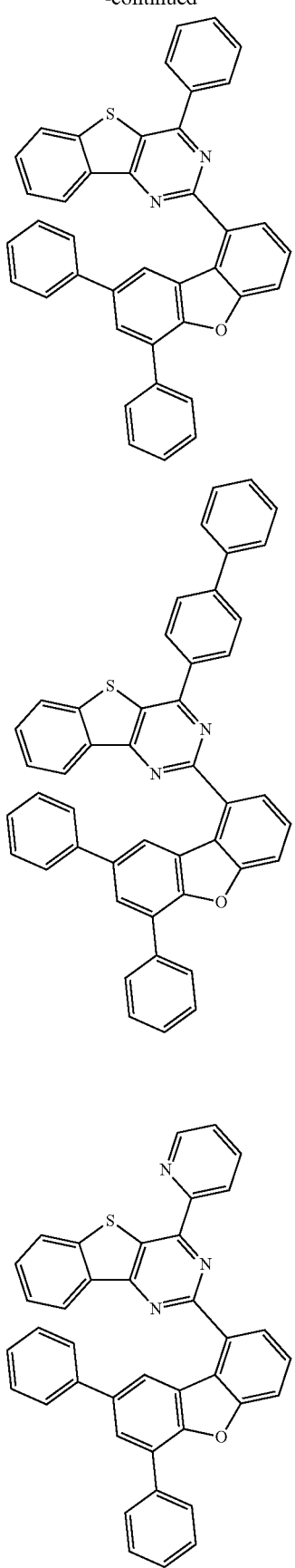

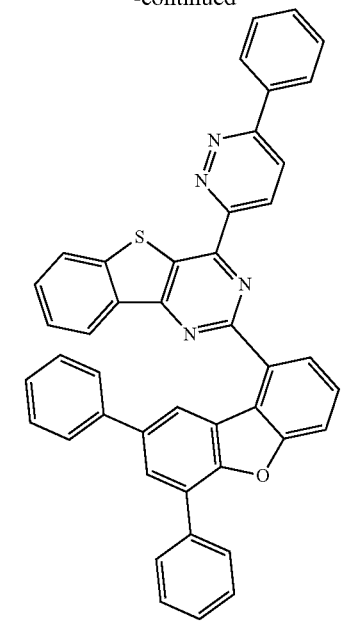
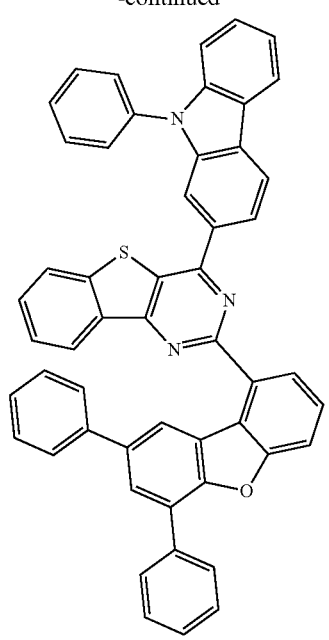
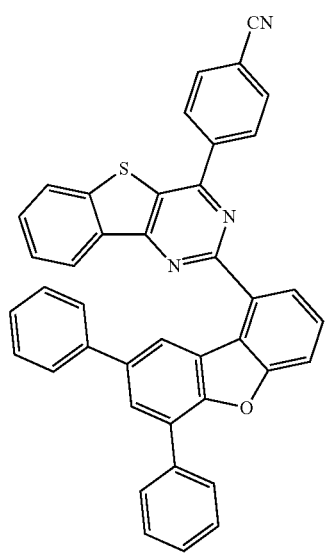
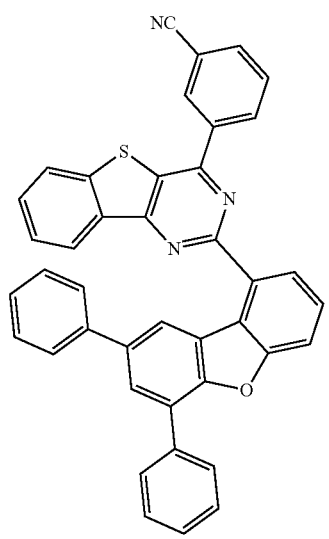

95
-continued
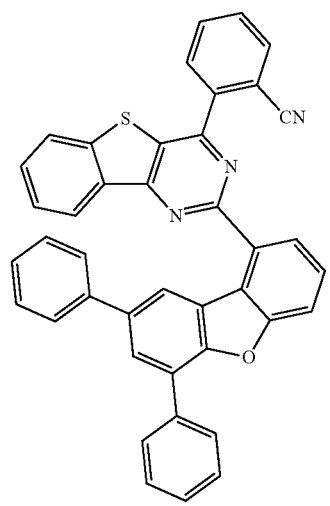
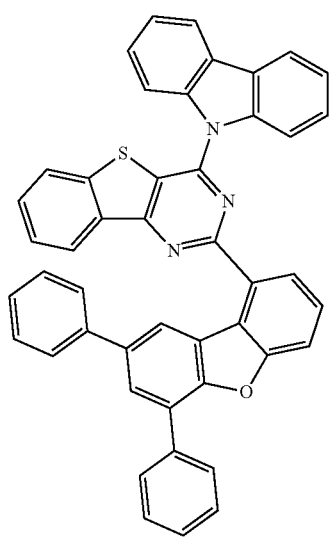
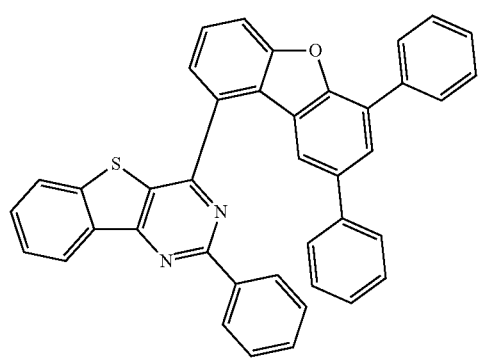
96
-continued
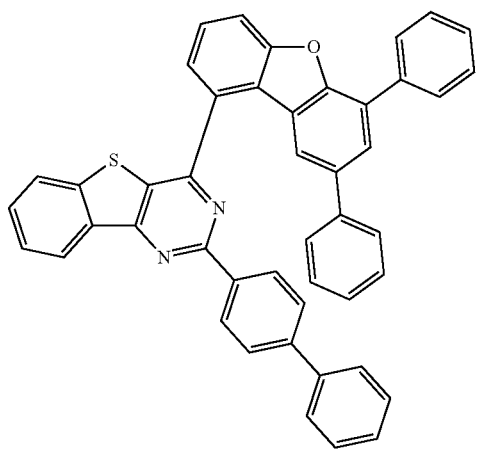
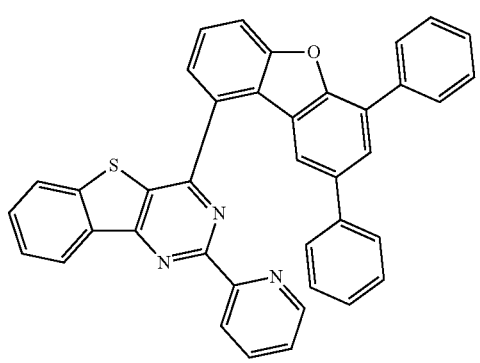
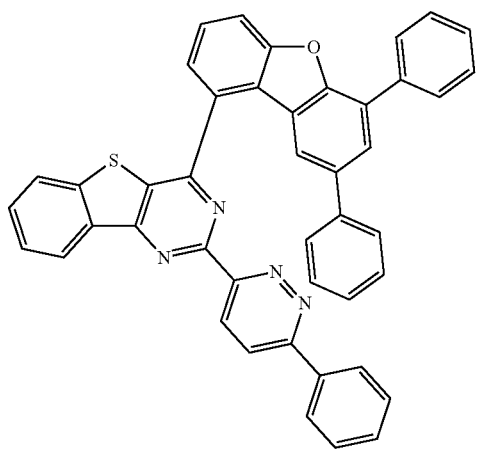

97
-continued
98
-continued
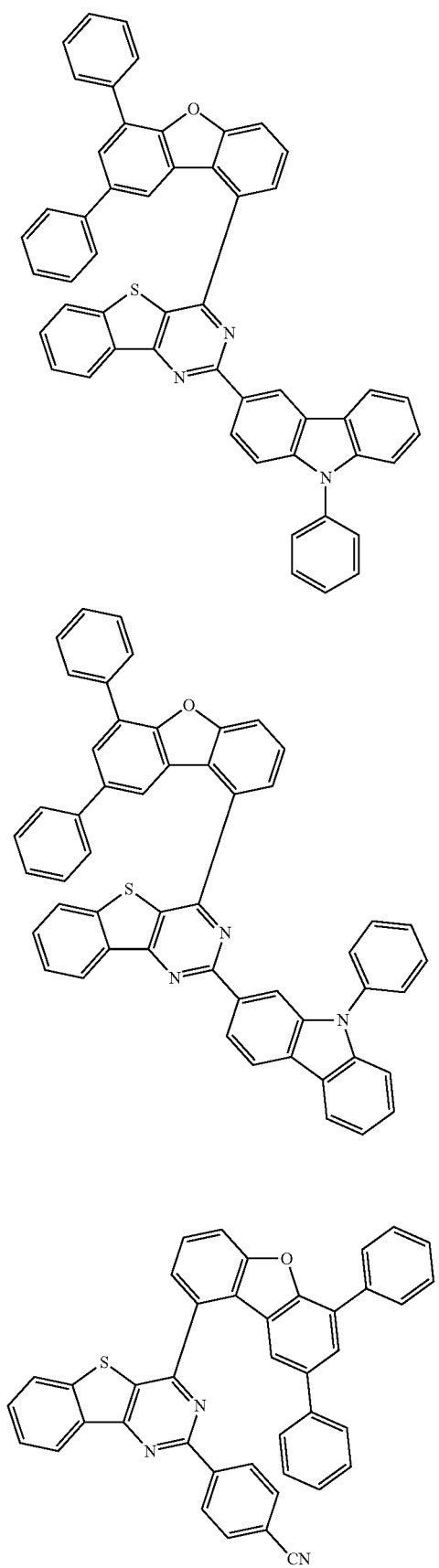
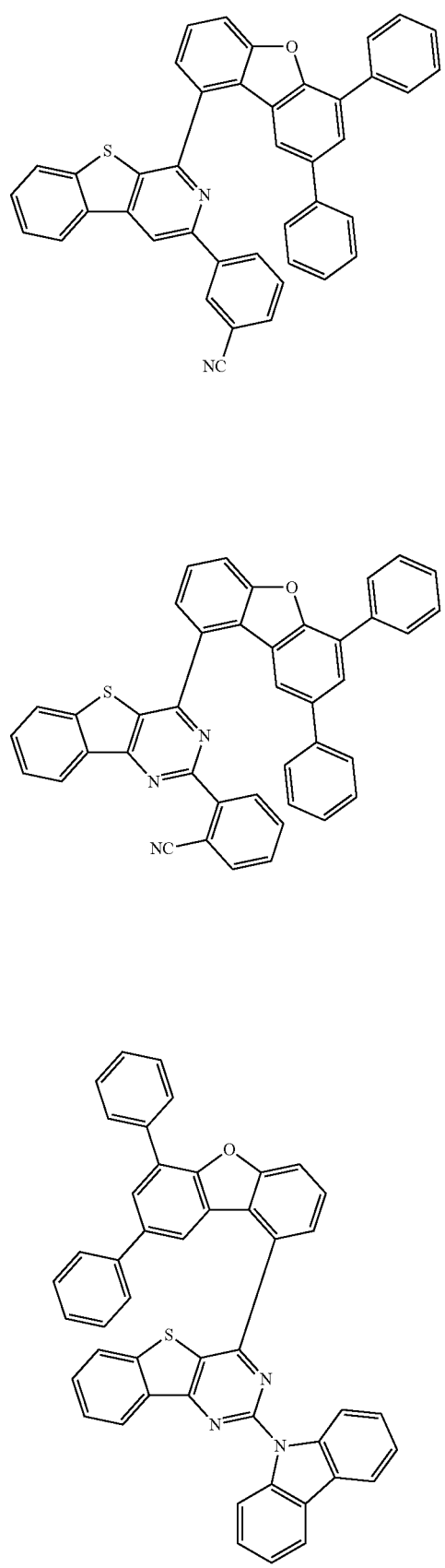

99
100
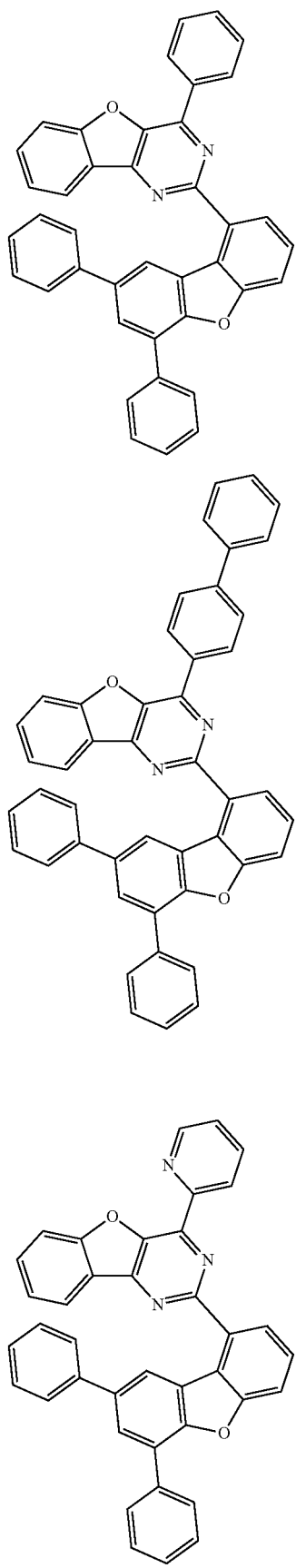

101
-continued
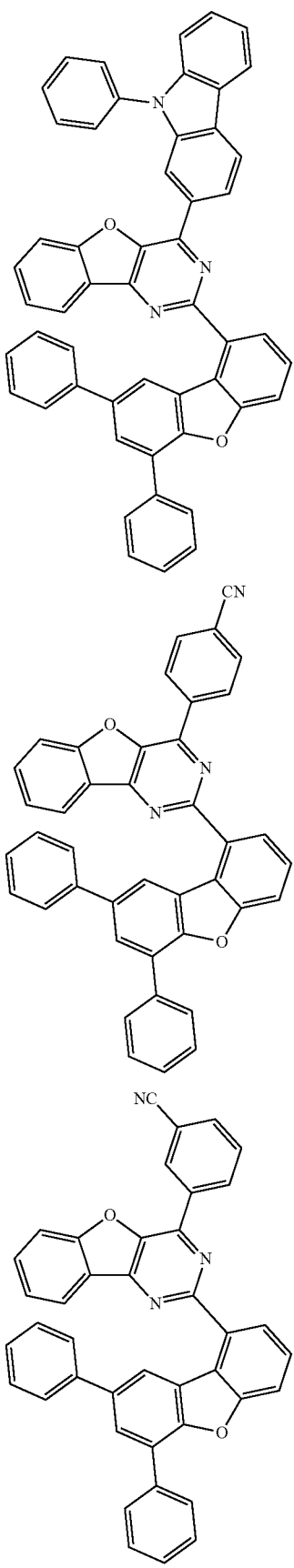
102
-continued
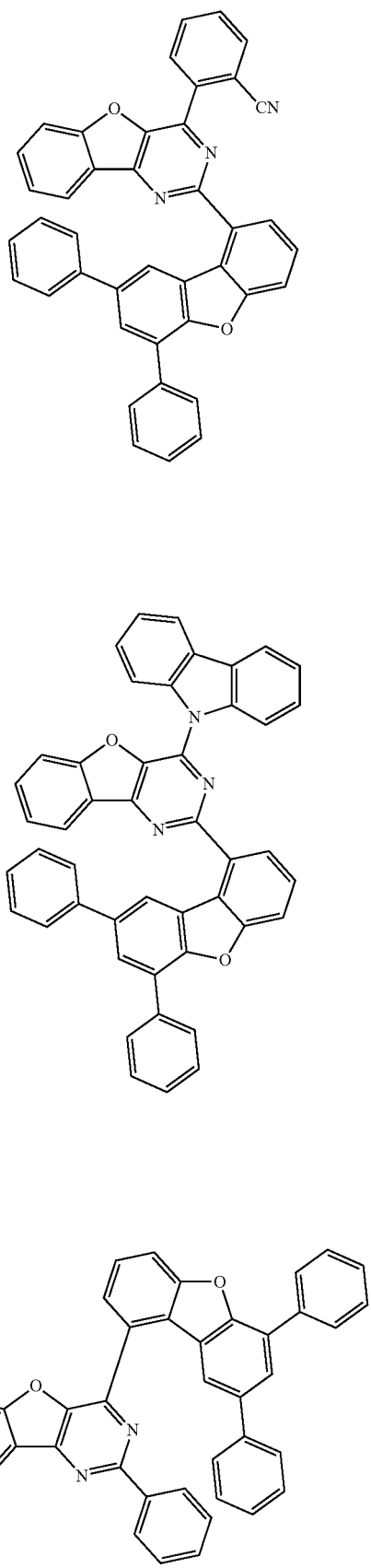

103
-continued
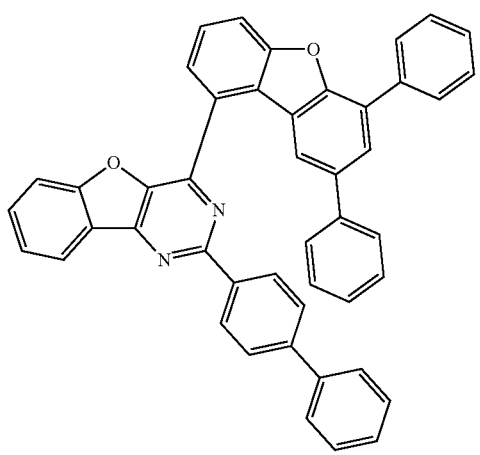
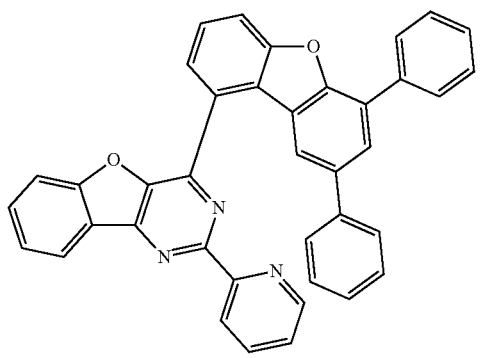
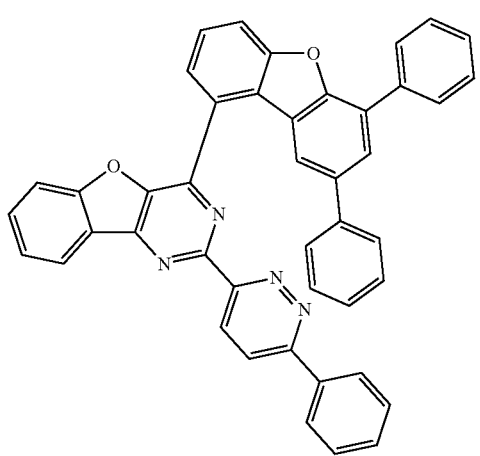
104
-continued
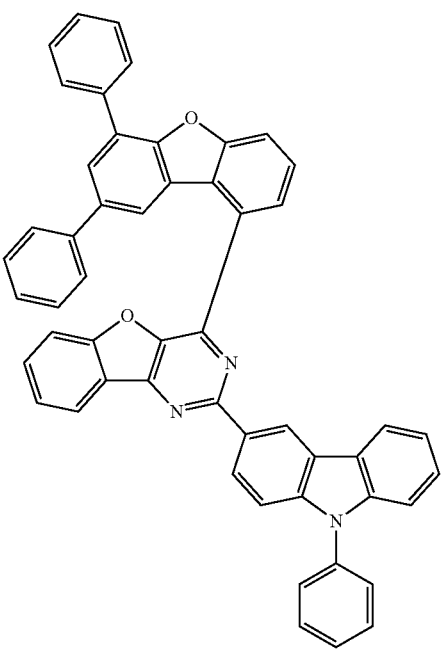
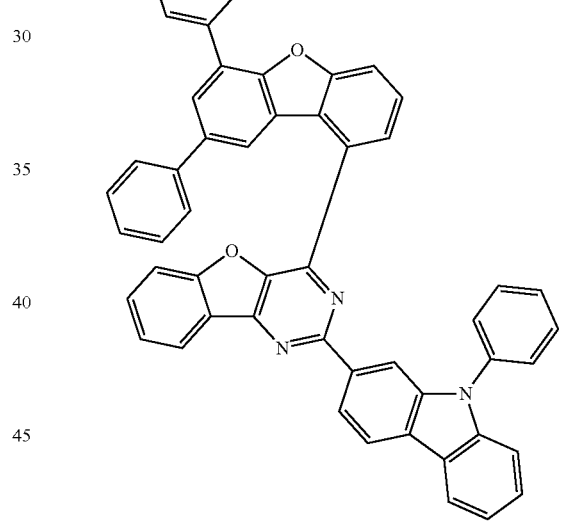
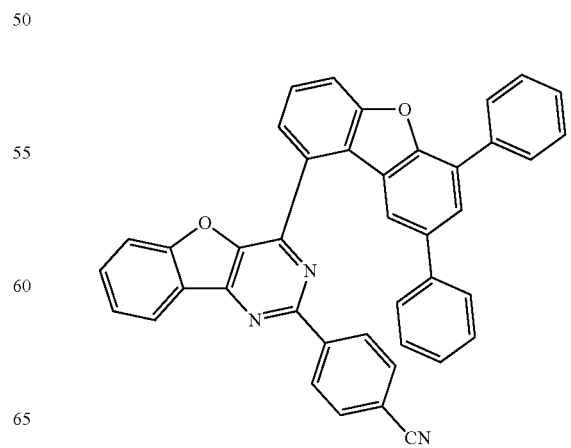

105
-continued
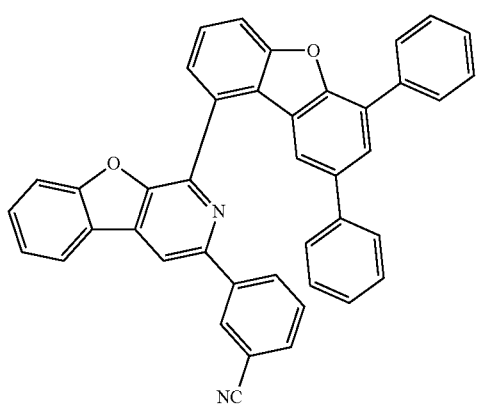
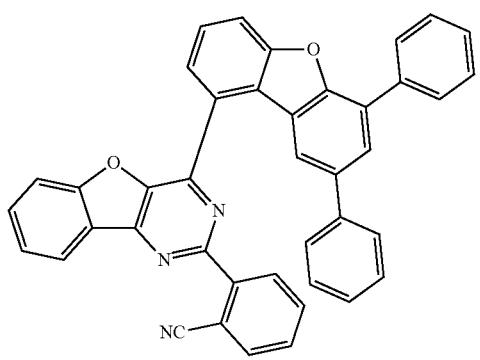
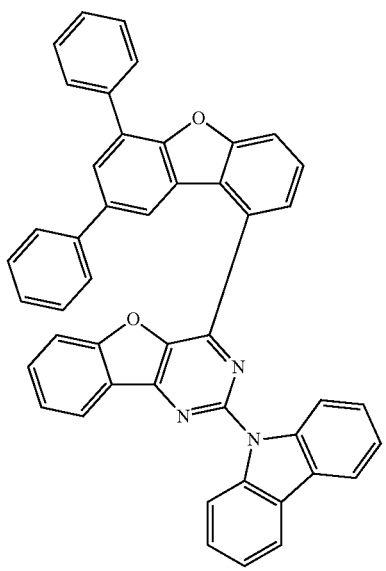
106
-continued
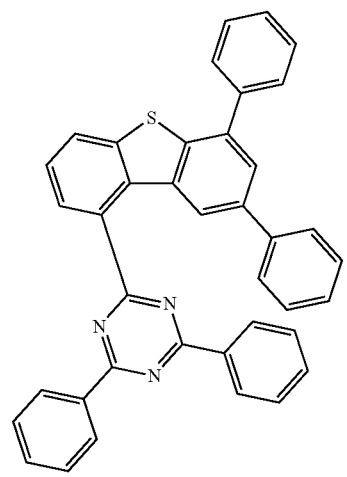
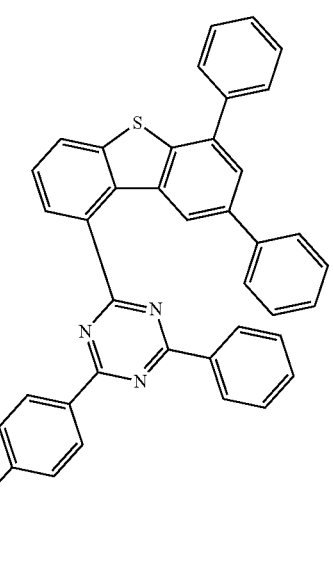
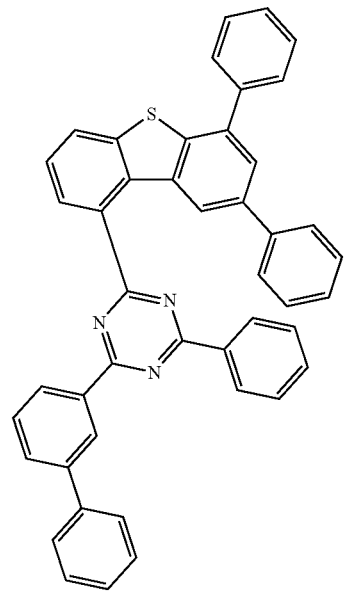

107
-continued

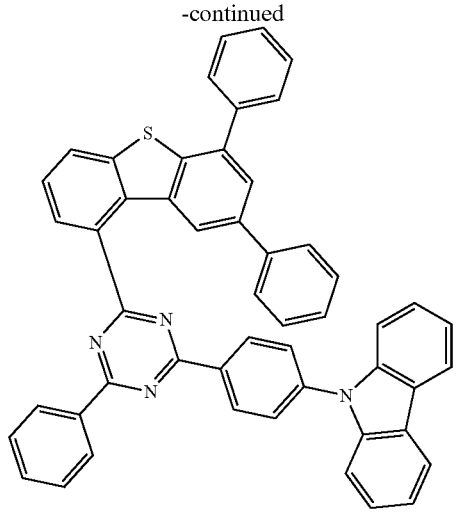

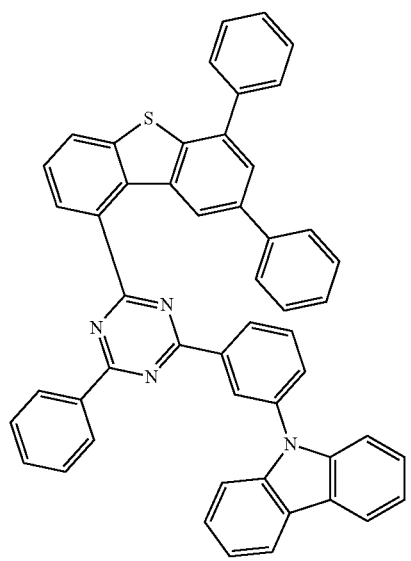

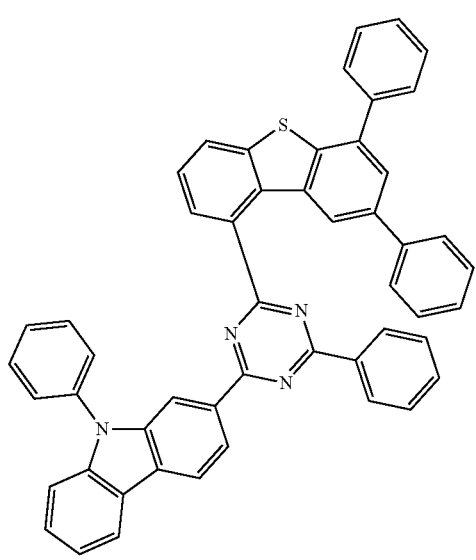

108
-continued

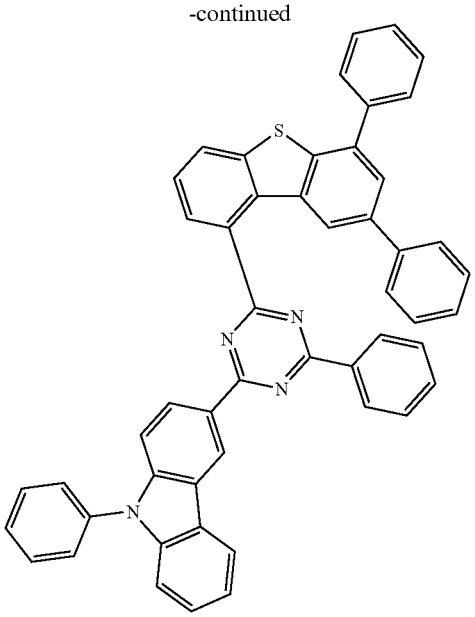

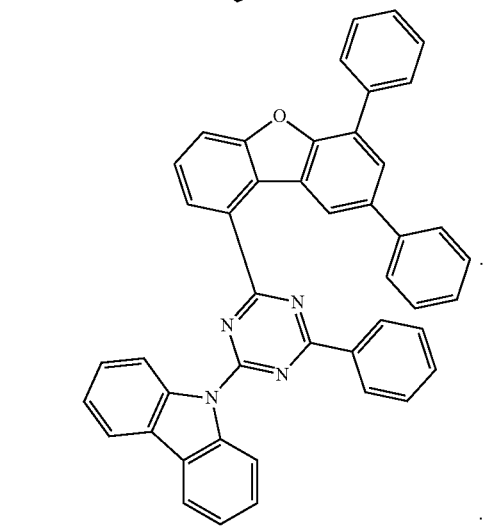

6. An organic light emitting device comprising a first electrode; a second electrode provided opposite to the first electrode; and one or more organic material layers provided between the first electrode and the second electrode, wherein one or more layers of the organic material layers comprise the compound of claim 1.

7. The organic light emitting device according to claim 6, wherein the organic material layer containing the compound includes a hole injection layer, a hole transport layer, an electron blocking layer, a light emitting layer, an electron transport layer, or an electron injection layer.

8. The organic light emitting device according to claim 6, wherein the light emitting layer includes two or more kinds of hosts, and one of the hosts is the compound.

9. An organic light emitting device comprising a first electrode; a second electrode provided opposite to the first electrode; and one or more organic material layers provided between the first electrode and the second electrode, wherein one or more layers of the organic material layers comprise the compound of claim 5.

10. The organic light emitting device according to claim 9, wherein the organic material layer containing the compound includes a hole injection layer, a hole transport layer, an electron blocking layer, a light emitting layer, an electron transport layer, or an electron injection layer.

11. The organic light emitting device according to claim 9, wherein the light emitting layer includes two or more kinds of hosts, and one of the hosts is the compound.

* * * * *

UNITED STATES PATENT AND TRADEMARK OFFICE
CERTIFICATE OF CORRECTION

PATENT NO.         : 11,925,113 B2
APPLICATION NO.    : 16/963189
DATED              : March 5, 2024
INVENTOR(S)        : Jung et al.

Page 1 of 1

It is certified that error appears in the above-identified patent and that said Letters Patent is hereby corrected as shown below:

In the Claims

In Claim 2, at Column 74, from Line 12 to Line 22, the first compound should appear as follows:

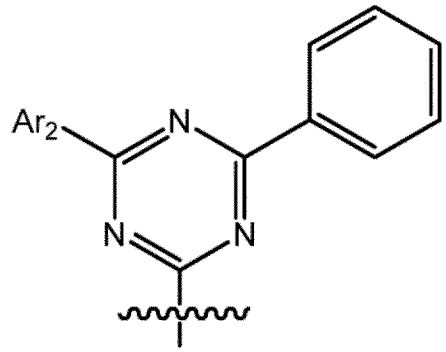

Signed and Sealed this
Ninth Day of April, 2024

Katherine Kelly Vidal
Director of the United States Patent and Trademark Office